(12) United States Patent
Fogelman et al.

(10) Patent No.: US 7,148,197 B2
(45) Date of Patent: Dec. 12, 2006

(54) ORALLY ADMINISTERED SMALL PEPTIDES SYNERGIZE STATIN ACTIVITY

(75) Inventors: Alan M Fogelman, Beverly Hills, CA (US); Gattadahalli M Anantharamaiah, Birmingham, CA (US); Mohamad Navab, Los Angeles, CA (US)

(73) Assignees: The Regents of the University of California, Oakland, CA (US); The University of Alabama Research Foundation, Birmingham, AL (US)

( * ) Notice: Subject to any disclaimer, the term of this patent is extended or adjusted under 35 U.S.C. 154(b) by 0 days.

(21) Appl. No.: 10/649,378

(22) Filed: Aug. 26, 2003

(65) Prior Publication Data

US 2004/0254120 A1 Dec. 16, 2004

Related U.S. Application Data

(60) Provisional application No. 60/494,449, filed on Aug. 11, 2003.

(51) Int. Cl.
*A61K 38/07* (2006.01)
*C07K 5/10* (2006.01)

(52) U.S. Cl. ........................................ 514/18; 530/330
(58) Field of Classification Search ................ 514/18; 530/330
See application file for complete search history.

(56) References Cited

U.S. PATENT DOCUMENTS

| | | | |
|---|---|---|---|
| 3,767,040 A | 10/1973 | Tushaus ..................... | 428/352 |
| 4,155,913 A | 5/1979 | Hellerbach et al. ......... | 540/560 |
| 4,643,988 A | 2/1987 | Segrest et al. ................ | 514/12 |
| 4,684,520 A * | 8/1987 | Bertelli ....................... | 424/94.1 |
| 5,298,490 A * | 3/1994 | Heavner et al. .............. | 514/17 |
| 5,344,822 A | 9/1994 | Levine et al. ................. | 514/13 |
| 5,595,973 A * | 1/1997 | Bogden ...................... | 514/18 |
| 5,721,138 A | 2/1998 | Lawn ......................... | 435/325 |
| 5,733,549 A | 3/1998 | Yamada et al. ............ | 424/185.1 |
| 5,733,879 A | 3/1998 | Rosseneu et al. ............. | 514/13 |
| 5,814,467 A | 9/1998 | Curtiss et al. ............... | 435/7.9 |

(Continued)

FOREIGN PATENT DOCUMENTS

IN 185761 4/2004

(Continued)

OTHER PUBLICATIONS

Tan et al. A novel highly efficient peptide-HLA class I binding assay . . . Journal of Immunological Methods. 1997, vol. 205, pp. 201-209.*

(Continued)

*Primary Examiner*—Jeffrey Edwin Russel
(74) *Attorney, Agent, or Firm*—Quine I.P. Law Group P.C.; Tom Hunter

(57) ABSTRACT

This invention provides novel peptides for the treatment of atherosclerosis. In certain embodiments the peptide is $X^1$-$X^2$-$X^3$-$X^4$ where $X^1$ and $X^4$ are independently selected from the group consisting of alanine (Ala), valine (Val), leucine (Leu), isoleucine (Ile), proline (Pro), phenylalanine (Phe), tryptophan (Trp), methionine (Met), serine (Ser) bearing a hydrophobic protecting group, beta-naphthyl alanine, alpha-naphthyl alanine, norleucine, cyclohexylalanine, threonine (Thr) bearing a hydrophobic protecting group, tyrosine (Tyr) bearing a hydrophobic protecting group, lysine (Lys) bearing a hydrophobic protecting group, arginine (Arg) bearing a hydrophobic protecting group, ornithine (Orn) bearing a hydrophobic protecting group, aspartic acid (Asp) bearing a hydrophobic protecting group, cysteine (Cys) bearing a hydrophobic protecting group, and glutamic acid (Glu) bearing a hydrophobic protecting group; $X^2$ and $X^3$ are independently selected from the group consisting of Asp, Arg, and Glu; and the peptide converts pro-inflammatory HDL to anti-inflammatory HDL or makes anti-inflammatory HDL more anti-inflammatory.

85 Claims, 22 Drawing Sheets

U.S. PATENT DOCUMENTS

| | | | | |
|---|---|---|---|---|
| 5,854,238 | A | 12/1998 | Kempen | 514/220 |
| 6,004,925 | A | 12/1999 | Dasseux et al. | 514/2 |
| 6,037,323 | A | 3/2000 | Dasseux et al. | 514/12 |
| 6,046,166 | A | 4/2000 | Dasseux et al. | 514/13 |
| 6,086,918 | A | 7/2000 | Stern et al. | 424/474 |
| 6,265,377 | B1 | 7/2001 | Dasseux et al. | 514/12 |
| 6,287,590 | B1 | 9/2001 | Dasseux et al. | 424/450 |
| 6,329,341 | B1 | 12/2001 | Dasseux et al. | 514/13 |
| 6,376,464 | B1 | 4/2002 | Dasseux et al. | 514/12 |
| 6,455,088 | B1 | 9/2002 | Dasseux et al. | 514/2 |
| 6,518,412 | B1 | 2/2003 | Dasseux et al. | 536/231 |
| 6,573,239 | B1 | 6/2003 | Dasseux et al. | 514/12 |
| 6,602,854 | B1 | 8/2003 | Dasseux et al. | 514/13 |
| 6,630,450 | B1 | 10/2003 | Dasseux et al. | 514/13 |
| 6,664,230 | B1 | 12/2003 | Fogelman et al. | 514/13 |
| 6,696,545 | B1 | 2/2004 | Buelow et al. | 530/328 |
| 6,716,816 | B1 | 4/2004 | Dasseux et al. | 514/13 |
| 6,734,169 | B1 | 5/2004 | Dasseux et al. | 514/12 |
| 6,753,313 | B1 | 6/2004 | Dasseux et al. | 514/12 |
| 2001/0005714 | A1 | 6/2001 | Boffelli et al. | 514/21 |
| 2002/0042441 | A1* | 4/2002 | Acton et al. | 514/415 |
| 2003/0027769 | A1* | 2/2003 | Scialdone et al. | 514/18 |
| 2003/0040505 | A1* | 2/2003 | Fogelman et al. | 514/78 |
| 2003/0045460 | A1 | 3/2003 | Fogelman et al. | 514/12 |
| 2003/0125260 | A1* | 7/2003 | Haviv et al. | 514/17 |

FOREIGN PATENT DOCUMENTS

| | | |
|---|---|---|
| WO | WO 96/41815 A2 * | 12/1996 |
| WO | WO 97/36927 | 10/1997 |
| WO | WO 97/36927 A1 | 10/1997 |
| WO | WO 99/16408 | 4/1999 |
| WO | WO 99/47566 A1 | 9/1999 |

OTHER PUBLICATIONS

Anantharamaiah (1986) "Synthetic Peptide Analogs of Appolipoproteins." *Methods in Enzymology* 128:627-647.

Anantharamaiah and Garber (1996) "Chromatographic Methods for Quantitation of Apolipoprotein A-I." *Meth. Enzymol.* 263: 267-282.

Anantharamaiah et al. (1985) "Studies of Synthetic Peptide of the Amphipathic Helix." *The Journal of Biological Chemistry* 260:10248-10255.

Anantharamaiah et al. (1990) "Use of Synthetic Peptide Analogues to Localize Lecithin: Cholseterol Acyltransferase Activating Domain in Apolipoprotein A-I." *Arteriosclerosis* 10:95-105.

Anantharamaiah et al. (1993) "An Atlas of the Amphipathic Helical Domains of Human Exchangeable Plasma Apolipoproteins." Chapter. 6:109-142 In: *The Amphipathic Helix* (Epand, R. M., ed), CRC Press, Boca Raton, FL.

Armstrong et al. (1993) D amino acid levels in human physiological fluids, *Chirality*, 5: 375-378.

Badimon et al. (1990) "Regression of Atherosclerotic Lesions by High Density Lipoprotein Plasma Fraction in the Cholesterol-fed Rabbit." *J. Clinical Investigation* 85:1234-1241.

Bauer et al. (1982) "SMS 201-995: A Very Potent and Selective Octapeptide Analogue of Somatostatin with Prolonged Action" *Life Sciences* 31:1133-1140.

Boffelli et al. (1997) "Reconstitution and Further Characterization of the Cholesterol Transport Activity of the Small-Intestinal Brush Border Membrane" *Biochemistry* 36:10784-10792.

Boffelli et al. (1997) "The uptake of cholesterol at the small-intestinal brush border membrane is inhibited by apolipoproteins." FEBS Letters, 411: 7-11.

Borhani et al. (1999) "Crystal structure of truncated human apolipoprotein A-I suggests a lipid-bound conformation." *Proc. Natl. Acad. Sci. USA.* 94:12291-12296.

Brouillette and Anantharamaiah (1995) "Structural models of human apolipoprotein A-I." *Biochim. Biophys. Acta* 1256: 103-129.

Brouillette et al. (2001) "Structural Models of Human Apolipoprotein A-I: A Critical Analysis and Review" *Biochemica et Biophysica Acta* 55753:1-44.

Canadian Pharmacists Association, Starlix General Monograph. http://cpha.infinetcomm.com/content/hcp/tools/cps_cnp_updates/starlix.cfm, 2002.

Chung et al. (1985) "Studies of Synthetic Peptide Analogs of the Amphipathic Helix." *J. Biol. Chem.* 60(18): 10256-10262.

Datta et al. (2001) Effects of Increasing Hydrophobicity on the Physical-Chemical and Biological Properties of a Class A Amphipathic Helical Peptide. *J Lipid Research* 42:1096-1104.

Davidson et al. (1994) "The Influence of Apolipoprotein Structure on the Efflux of Celluar Free Cholesterol to High Density Lipoprotein." *J. Biol. Chem.* 269(37): 22975-22982.

Diederich et al. (2001) "Apolipoprotein Al and $HDL_3$ Inhibit Spreading of Primary Human Monocytes through a Mechanism that Involves Cholesterol Depletion and Regulation of CD42." *Atherosclerosis* 159:313-324.

Dooley et al. (1994) "An All D-Amino Acid Opioid Peptide with Central Analgesic Activity from a Combinatorial Library" *Science* 2019-2022.

Dunlop and Neidle (1997) "The Orgion and Turnover of D-Serine in Brain." *Biochemical and Biophysical Research Communication* 235:26-30.

Ehara et al. (2001) "Elevated Levels of Oxidized Low Density Lipoprotein Show a Positive Relationship With the Severity of Acute Coronary Syndromes." *Circulation* 103:1955-1960.

Epand et al. (1987) "Studies Synthetic Peptide Analog of the Amphipathic Helix" *J. Biol. Chem.* 262(19): 9389-9396.

Field et al. (2001) "Gene expression of sterol regulatory element-binding proteins in hamster small intestine." *Journal of Lipid Research* 42:1-9.

Fielding and Fielding (1995) "Molecular physiology of reverse cholesterol transport." *J. Lipid Res.* 36: 211-228.

Fielding et al. (1972) "A Protein of Lecithin: Cholester Acyltransferase." *Biochem. Biophys. Res. Comm.* 46(2):1493-1498.

Fricker et al. (1995) "Enteral Absorption of Octreotide: Modulation of Intestinal Permeability by Distinct Carbohydrates" *The Journal of Pharmacology and Experimental Therapeutics* 274:826-832.

Fuessl et al. (1987) "Oral Absroption of the Somatostatin Analogue SMS 201-995: Theoretical and Practial Implications" *Clinical Science* 72: 255-257.

Garber et al. (1992) "Turnover of synthetic class A amphipathic peptide analogues of exchangeable apolipoproteins in rats. Correlation with physical properties." *Arteriosclerosis and Thrombosis*, 12(8): 886-894.

Garber et al. (1997) *Circulation* 96-I-490.

Garber et al. (1999) "Protection against Atherosclerosis in Mice by a Synthetic Class A Amphipathic Peptide Analog of Apolipoprotein A-I." *Circulation* 100: 2838.

Garber et al. (2001) "A new synthetic class A amphipathic peptide analogue protects mice from diet-induced atherosclerosis." *Journal of Lipid Research* 42:-545-552.

Glomset (1968) "The Plasma lecithin: cholesterol acytransferase reaction." *J. Lipid Res.* 9:155-167.

Gong et al. (1994) "Structural and functional properties of human and mouse apolipoprotein A-I." *Biochim. Biophys. Acta* 1213:335-342.

Gurfinkel et al. (2002) "Influenza Vaccine Pilot Study in Acute Coronary Syndromes and Planned Percutaneous Coronary Interventions. The FLU Vaccination Acute Coronary Syndromes (FLUVACS) Study" *Circulation* 105:2143-2147.

Hamase et al. (2001) "Determination of Free D-Proline and D-Leucine in the Brains of Mutant Mice Lacking D-Amino Acid Oxidase Activity" *Analytical Biochemistry* 298:253-258.

Hardy et al. (2001) "An Automated High-Performance Liquid Chromatography Procedure for the Quantitation of L- and D-Amino Acids by Means of Stepwise Precolumn Derivatization" Analytical Biochemistry 291:297-299.

Hashimoto et al. (2000) "Improvement of intestinal absorption of peptides: absorption of B1-Phe monoglucosylated insulin to rat intestinal brush-border membrane vesicles." *J. Pharmaceutics & Therapeutics* 50(2):197-204.

Hauser et al. (1998) "Identification of a Receptor Mediating Absorption of Dietary Cholesterol in the Intestine" *Biochemistry* 178423-17850.

Hayry et al. "Stabile D-peptide analog of insulin-like growth factor-1 inhibits smooth muscle cell proliferation after carotid ballooning injury in the rat." *FASEB J.* 9(13):1336-1344, 1995.

Hyka et al. (2001) "Apolipoprotein A-I Inhibits the Production of Interleukin-1beta and Tumor Necrosis Factor-alpha by Blocking Contact-Mediated Activation of Monocytes by T Lymphocytes." *Blood* 97:2381-2389.

Johnson et al. (1991) "Cholesterol transport between cells and high-density lipoproteins." *Biochim. Biophys. Acta.* 1085:273-298.

Jonas (1991) "Lecithin-cholesterol acyltransferase in the metabolism of high-density lipoproteins." *Biochim. Biophys. Acta* 1084: 205-220.

Jonas (2000) Lecithin cholesterol acyltransferase. *Biochim. Biophys. Acta* 1529: 245-256.

Jones et al. (1992) "Computer Programs to Identify and Classify Amphipathic alpha Helical Domains" *Journal of Lipid Research* 33:287-296.

Kigasawa et al. (1995) "Inhibition of corneal ulceration by tetrapeptidyl hydroxamic acid." *Jap. J. Ophthamology* 39(1):35-42.

Kreiger (1999) "Charting The Fate of the "Good Cholesterol": Identifcation and Characterization of the High-Density Lipoprotein Receptor Sr-Bi." *Ann. Rev. Biochem.* 68: 523-558.

Kullman etal. (1999) "Evaluation of the Enantiomeric Composition of Amino Acids in Tobacco" *Chirality* 11:669-673.

Senior (1999) "New options developed for needle-free drug delivery" *Lancet* Sep. 25, 1999.

Levi et al. (2000) "A retro-inverso minantibody with anti-HIV activity." *Aids Res. & Human Retruvirus* 16(1):59-65.

Lundin et al. (1986) "Absorption of Intragastrically Administered DDAVP in Conscious Dogs" *Life Sciences* 38:703-709.

Man et al. (1987) D-aspartate in human brain. *J Neurochem* 48:510-515.

Merrifield et al. (1995) "Retro and Retroenantio Analogs of Cecropin-Melittin Hybrids" *Proc Natl Acad Sci USA* 92: 3449-3453.

Mishra et al. (1994) "Interaction of Synthetic Peptide Analogs of the Class A" *J. Biol. Chem.* 269: 7185-7191.

Mishra et al. (1995) "Effect of the Arrangement of Tandem Repeating Units of Class A Amphipathic alpha-Helixes on Lipid Interaction." *J. Biol. Chem.* 270: 1602-1611.

Mishra et al. (1998) Studies of Synthetic Peptides of Human Apolipoprotein A-I Containing Tandem Amphipathic alpha-Helixes *Biochemistry* 37: 10313-10324.

Mor et al. (1992) Enter a new post-translational modification: D-amino acids in gene-encoded peptides, *TIBS*, 17: 481-485.

Nagata et al. (1994) "Distribution of free D-serine in vertebrate brains", *Brain Res.*, 634: 291-295.

Nagata et al. (1995) "Free D-serine concentration in normal and Alzheimer human brain", *Brain Res. Bull.*, 38(2): 181-183.

Navab et al. (2000) "Normal high-density lipoprotein inhibits three steps in the formation of midly oxidized low density lipoprotein: step 1." *J. Lipid Res.* 41: 1481-1494.

Navab et al. (2000) "Normal high-density lipoprotein inhibits three steps in the formation of mildly oxidized low density lipoprotein: steps 2 and 3." *J. Lipid Res.* 41: 1495-1508.

Navab et al. (2002) "Oral Administration of an Apo A-I Mimetic Peptide Synthesized from D-Amino Acids Dramatically Reduces Atherosclerosis in Mice Independent of Plasma Cholesterol" *Circulation* 105: 290-292.

Nomoto et al. (1998) "Improved of intestinal absorbtion of peptide drugs by Gyycosylation: Transport of Tetrapeptide by the Sodium Ion-Dependent D-Glucose Transporter." *J. Pharmaceutics Science* 87(3):326-332.

Ohtani et al. (1995) Age-related changes in D-aspartic acid of rat teeth, *Growth Develop. & Aging*, 59: 55-61.

Oram and Yokoyama (1996) "Apolipoprotein-mediated removal of cellular cholesterol and phospholipids." *J. Lipid Res.* 37: 2473-2491.

Owens et al. (1990) "Apolipoprotein A-I and its Amphipathic Helix Peptide Analogues Inhibit Human Immunodeficiency Virus-Induced Syncytium Formation" *J Clin Invest* 86: 1142-1150.

Paigen et al. (1990) "Atherosclerosis Susceptibility Differences among Progenitors of Recombinant Inbred Strains of Mice." *Arteriosclerosis* 10: 316-323.

Palgunachari et al. (1996) "Only the Two End Xelises of Eight Tandem Amphipathic Helical Domaine of Human Apo A-I Have Significant Lipid Affinity." *Arteriosclerosis, Thrombosis, & Vascular Biology* 16: 328-338.

Panizzutti et al. (2001) "A New Strategy to Decrease N-methyl-D-aspartate (NMDA) Receptor Coactivation: Inhibition of D-serine Synthesis by Converting Serine Racemase into an Eliminase" *PNAS* 98:5294-5299.

Pappenheimer et al. (1994) "Intestinal Absorption and Excretion of Octapeptides Composed of D Amino Acids" *Proc Natl Acad Sci USA* 91: 1942-1945.

Pappenheimer et al. (1997) "Absorption and Excretion of Undegradable Peptides: Roles of Lipid Solubility and Net Charge." *J. Pharmacology & Experimental Therapeutics* 280(1):292-300.

Patszty et al. (1994) "Apolipoprotein AI Transgene Corrects Apolipoprotein E Deficiency-induced Atherosclerosis in Mice." *J. Clinical Investigation* 94:899-903.

Peng et al. (2001) "Effects of L-glutamate, D-aspartate, and Monensin on Glycolytic and Oxidative Glucose Metabolism in Mouse Astrocyte Cultures: Further Evidence that Glutamate Uptake is Metabolically Driven by Oxidative Metabolism" *Neurochemistry International* 38:437-443.

Pharmalicensing (Jan. 27, 2001) Esperion Builds a Novel Peptides Program (2 pages).

Pharmalicensing (Jan. 28, 2001) Multiple Peptide Systems Forms Joint Venture With Elan.

Pharmalicensing (Jan. 28, 2001) Unigene to Receive Patent for Delivery of Peptide Pharmaceuticals (2 pages).

Philips et al. (1993) "Plasma Lipoproteins and Progression of Coronary Artery Disease Evaluated by Angiography and Clinical Events." *Circulation* 88: 2762-2770.

Pilone (2000) D-amino acid oxidase: new findings. *CMLS, Cell. Mol. Life Sci.*, 57: 1732-1747.

Plump et al. (1994) "Human apolipoprotein A-I gene expression increases high density lipoprotein and suppresses stherosclerosis in the apolipoprotein E-deficient mouse." *Proc. Natl. Acad. Sci.* USA 91:9607-9611.

Purdue News (Oct. 2000) 'Microspheres' Offer Promise for Oral Drug Delivery (3 pages.).

Purdue News (Sep. 12, 1997) New Oral Insulin Delivery System Shows Promise (3 pages).

Reubsaet et al. (1999) "Qualitative and quantitative aspects of the degradation of several tripeptides derived from the antitumour peptide antagonist [Arg$^6$, D-Trp$^{7,9}$, MePhe$^8$] substance P{6-11}." *J. Pharmaceut. & Biomed Analysis* 19(3-4):277-284.

Rubin et al. (1991) "Inhibition of early atherogenesis in transgenic mice by human apolipoprotein AI." *Nature* 353:265-267.

Segrest et al. (1974) "A Molecular Theory of Lipid-Protein Interaction in the Plasma Lipoproteins." *FEBS Lett.* 38: 247-253.

Segrest et al. (1990) "Amphipathic Helix Motif: Classes and Properties." *Proteins: Structure, Function and Genetics* 8: 103-117.

Segrest et al. (1992) "The Amphipathic Helix in the Exchangeable Apolipoproteins: A Review of Secondary Structure and Function" *J Lipid Research* 33:141-166.

Segrest et al. (1994) "The Amphipathic alpha Helix: A Multifunctional Structural Motif in Plasma Apolipoproteins." *Adv. Prot. Chem.* 45: 303-369.

Segrest et al. (2000) "Structure and function of apolipoprotein A-I and high-density lipoprotein." *Current Opin. Lipidol.* 11:105-115.

Shah et al. (1998) "Effect of Recombinant Apolipoprotein A-I$_{Milano}$ on Aortic Atherosclerosis in Apolipoprptein E-Deficient Mice." *Circulation* 97:780-785.

Singh et al. (2000) "Innate Defences Against Viraemia" *Rev Med Virol* 10:395-403.

Sprecher et al. (1993) "The Low HDL Cholesterol/ High Triglyceride Trait." *Arterioscler. Thromb.* 13: 495-504.

Srinivas et al. (1990) "Antivrial Effects of Apolipoprotein A-I and Its Synthetic Amphipathic Peptide Analogs" *Virology* 176:48-57.

Starlix MC—Amino Acid Fact Sheet. http://www.starlix.com/media_center/content/pages/amino.htm, 2002.

Su and Amidon (1995) Investigation into the intestinal metabolism of [D-Ala] peptide T amide: implication for oral drug delivery, *Biochim et Biophys.*, 1245: 62-68.

The Wall Street Journal (Jan. 13, 2000) "Emisphere technologies develops oral Heparin".

Tsai et al. (1998) D-serine added to antipsychotics for the treatment of schizophrenia. *Biol. Psychiatry*, 44: 1081-1089.

Tsao et al. (2001) "Hibernation-induction Peptide and Cell Death: [D-Ala$^2$, D-Leu$^5$]enkephalin Blocks Bax-related Apoptotic Processes" *European Journal of Pharmacology* 428:149-151.

Tsimikas et al. (2001) "Measuring Circulating Oxidized Low-Density Lipoprotein to Evaluate Coronary Risk." *Circulation* 103:1930-1932.

Van Lenten et al. (2001) *Circulation* 103:2283-2288.

Venkatachalapathi et al. (1993) "Effect of End Group Blockage on the Properties of a Class A Amphipathic Helical Peptied." *Proteins-:Structure, Function, and Genetics* 15:349-359.

Wilson et al. (1988) "High Density Lipoprotein Cholesterol and mortality: The Framingham Heart Study." *Arteriosclerosis* 8: 737-741.

Yancey et al. (1995) "Efflux of Cellular Cholesterol and Phospholipid to Lipid-free Apolipoproteins and Class A Amphipathic Peptides." *Biochemistry*, 34: 7955-7965.

Gorski,A et al. Cyclolinopeptide: a novel immunosuppressive agent with potential anti-lipemic activity. Arch. Immunol. Ther Exp. 1999; 47(3): 143-153.

Kluczyk, A. Siemion, TH:ca, Szewczuk, Z., and Wieczorek, Z. The immunosuppressive activity of peptide fragments of viccinia virus C10L protein and a hypothesis on the role of this protein in the viral invasion. Peptides 2002; 23: 823-834.

Mathison, R., Lo, P., Moore, G., Scott, B. and Davison, J. Attenuation of Intestinal and Cardiovascular Anaphylaxis by the Salivary Gland Tripeptide FEG and Its D-isometric Analog feG. Peptides 1998; 19 (6) 1037-1042.

Mathison, R., Woodman, R. and Davison, J. Regulation of leukocyte adhesion to heart by the tripeptides feG and feG(NH2) Can. J. Physiol. Pharm. 2001; 79: 785-792.

Mathison, R., Befus, A., Davison, J. and Woodman, R. Modulation of neutrophil function by the tripeptide feG. BMC Immunology 2003; 4: 1471-2172.

Mathison, R., Lo, P., Tan, R. and Davison, J. The tripeptide feG reduces endotoxin-provoked perturbation of intestinal motility and inflammation. Neurogastrointerol 2001; 13: 599-603.

Mathison, R. Davison, J. and Metwally, E. Identification of a binding site for the anti-inflammatory tripeptide feG. Peptides 2003; 24: 1221-1230.

Metwally, E., Befus, A., Davison, J. and Mathison, R. Probing for submandibular gland peptide-t receptors on leukocytes with biotinylated-Lys [Gly]6-AGP-T. Biochimica et Biophysica Acta 1593 2002; 37-44.

Metwally, E., Davison, J. and Mathison, R. Tyrosine is detrimental to the biological activity of submandibular gland peptide-T (SGP-T) Proc. West Pharmacol. Soc. 1999; 42: 65-66.

Metwally, E., Pires, J., Moore, G., Befus, D., Davison, J. and Mathison, R. Submandibular gland tripeptide FEG (Phe-Glu-Gly) and analogues: keys to structure determination. Peptides 2002; 23: 193-199.

Metwally, E., Ismail, A., Davison, J. and Mathison, R. A tree based algorithm for determining the effects of solvation on the structure of salivary gland tripeptide NH3+-D-PHE-D-GLU-GLY-COO. Biophysical Journal 2003; 65: 1503-1511.

Siemion, I. And Wieczorek, Z. Antiadhesive peptides as the inhibitors of mycobacterium kansasii phagocytosis. Peptides 2003; 24: 623-628.

Seimion, I. Et al. Analogs of RGDVY and GRGD peptides inhibit mycobacterium kansaii phagocysis. Peptides 2003; 24: 1109-1115.

Sundal, E. Thymopentin prophylactic treatment in patients with recurrent respirator infections. Br. J Clin Pract. 1993;47: 198-204.

Szewczuk, Z. Immunosuppressory activity of the cyclodimetric peptide with RGD-sequences. Acta. Biochimica Polonica 2001; 48: 121-130.

Tan et al. The carboxamine feG(NH2) inhibits endotoxin perturbation of intestinal motility. Eurp. Jol. Of Pharm. 2000; 203-205.

Turesin, F. et al. The tripeptide feG ameliorates systemic inflammatory responses to rat intestinal anaphylaxis. BMC Physiology 2002; 2(13) 1472-6793.

Aravinda, S., Shamala, N., Das, C. , Sriranjini, A. , Karle, I. And Balaram, P. Aromatic—Aromatic Interactions in Crystal Structures of Helical Peptide Scaffolds Containing Projecting Phenylalinine Residues, J.Am Chem Soc. 2003; 125:5308-5315.

Ashby D, Gamble J, Vadas M, Fidge N, Siggins S, Rye K, Barter PJ. Lack of effect of serum amyloid A (SAA) on the ability of high-density lipoproteins to inhibit endothelial cell adhesion molecule expression. *Atherosclerosis*. 2001;154:113-121.

Ashby DT, Rye K-A, Clay MA., Vadas MA, Gamble J, Barter PJ. Factors influencing the ability of HDL to inhibit expression of vascular cell adhesion molecule-1 in endothelial cells. *Arteriosclerosis, Thrombosis and Vascular Biology*, 1998,18:1450-1455.

Baker PW, Rye K-A, Gamble JR, Vadas MA, Barter PJ. Ability of reconstituted high density lipoproteins to inhibit cytokine-induced expression of vascular cell adhesion molecule-1 in human umbilical cell endothelial cells. *Journal of Lipid Research*, 1999, 40:345-353.

Baker PW, Rye KA, Gamble JR, Vadas MA, Barter PJ. Phospholipid composition of reconstituted high density lipoproteins influences their ability to inhibit endothelial cell adhesion molecule expression. *J. Lipid Res* 2000;41:1261-1267.

Barter PJ, Baker PW, Rye K-A.. Effect of high-density lipoproteins on the expression of adhesion molecules in endothelial cells. *Current Opinion in Lipidology*, 2002, 13:285-288.

Barter PJ, Rye K-A. High density lipoproteins and coronary heart disease. *Atherosclerosis*, 1996, 121:1-12.

Bauer et al. "SMS 201-995: A Very Potent and Selective Octapeptide Analogue of Somatostatin with Prolonged Action" *Life Sciences* 31:1133-1140, 1982.

Blankenberg S, Rupprecht HJ, Bickel C, Peetz D, Hafner G, Tiret L, Meyer J. Circulating cell adhesion molecules and death in patients with coronary artery disease. *Circulation* 2001;104:1336-1342.

Boffelli et al. "Reconstitution and Further Characterization of the Cholesterol Transport Activity of the Small-Intestinal Brush Border Membrane" *Biochemistry* 36;10784-10792, 1997.

Bourdillon MC, Poston RN, Covacho C, Chignier E, Bricca G, McGregor JL. ICAM-1 deficiency reduces atherosclerotic lesions in double-knockout mice (ApoE(-/-)/ICAM-1(-/-)) fed a fat or a chow diet. *Arterioscler Thromb Vasc Biol* 2000;20:2630-2635.

Bowry VW, Stanley KK, Stocker R. High density lipoprotein is the major carrier of lipid hydroperoxides in human blood plasma from fasting donors. *Proc Natl Acad Sci U S A*. 1992;89:10316-10320.

Brouillette et al. "Structural Models of Human Apolipoprotein A-I: A Critical Analysis and Review" *Biochemica et Biophysica Acta* 55753:1-44, 2001.

Burger D, Dayer J-M. High-density lipoprotein-associated apolipoprotein A-I: the missing link between infection and chronic inflammation? *Autoimmunity Reviews* 2002;1:111-117.

Calabresi L, Franceschini G, Sirtori CR, De Palma A, Saresella M, Ferrante P, Taramelli D. Inhibition of VCAM-1 expression in endothelial cells by reconstituted high density lipoproteins. *Biochem Biophys Res Commun*. 1997;238:61-65.

Calabresi L, Gomaraschi M, Villa B, Omoboni L, Dmitrieff C, Franceschini G. Elevated cellular adhesion molecules in subjects with low HDL-cholesterol. *Arterioscler Thromb Vasc Biol* 2002;22:656-661.

Carlos TM, Schwartz BR, Kovach NL, Yee E, Rosa M, Osborn L, Chi-Rosso G, Newman B, Lobb R, Rosso M, et al. Vascular cell adhesion molecule-1 mediates lymphocyte adherence to cytokine-activated cultured human endothelial cells. *Blood* 1990;76:965-970.

Carr AC, McCall MR, Frei B. Oxidation of LDL by myeloperoxidase and reactive nitrogen species oxidation of LDL by myeloperoxidase and reactive nitrogen species. *Arterioscler Thromb Vasc Biol*. 2000;20:1716-1723.

Castelli WP, Garrison RJ, Wilson PW, Abbott RD, Kalousdian S, Kannel WB. Incidence of coronary heart disease and lipoprotein cholesterol levels. The Framingham study. *JAMA* 1986;256:2835-2838.

Chiesa G, Monteggia E, Marchesi M, Lorenzon P, Laucello M, Lorusso V, Di Mario C, Karvouni E, Newton RS, Bisgaier CL, Franceschini G, Sirtori CR. Recombinant apolipoprotein A-I(Milano) infusion into rabbit carotid artery rapidly removes lipid from fatty streaks. *Circ Res.* 2002;90:974-980.

Christison J, Karjalainen A, Brauman J, Bygrave F, Stocker R. Rapid reduction and removal of HDL- but not LDL-associated cholesteryl ester hydroperoxidse by rat liver perfused in situ. *Biochem J.* 1996;314:739-742.

Clay MA, Pyle DH, Rye K-A, Vadas MA, Gamble JR, Barter PJ. Time sequence of the inhibition of endothelial adhesion molecule expression by reconstituted high density lipoproteins. *Atherosclerosis*, 2002,157:23-29.

Cockerill GW, Huehns TY, Weerasinghe A, Stocker C, Lerch PG, Miller NE, Haskard DO. Elevation of plasma high-density lipoprotein concentration reduces interleukin-1-induced expression of E-selectin in an in vivo model of acute inflammation. *rculation* 2001;103:108-112.

Cockerill GW, Rye KA, Gamble JR, Vadas MA, Barter PJ. High-density lipoproteins inhibit cytokine-induced expression of endothelial cell adhesion molecules. *Arterioscler Thromb Vasc Biol.* 1995;15:1987-1994.

Cockerill GW, Saklatvala J, Ridley SH, Yarwood H, Miller NE, Oral B, Nithyanathan S, Taylor G, Haskard DO. High-density lipoproteins differentially modulate cytokine-induced expression of E-selectin and cyclooxygenase-2. *Arterioscler Thromb Vasc Biol.* 1999;19:910-917.

Cybulsky MI, Iiyama K, Li H, et al. A major role for VCAM-1, but not ICAM-1, in early atherosclerosis. *Journal of Clinical Investigation* 2001;107:1255-1262.

Cyrus T, Pratico D, Zhao L, Witztum JL, Rader DJ, Rokach J, FitzGerald GA, Funk CD. Absence of 12/15-lipoxygenase expression decreases lipid peroxidation and atherogenesis in apolipoprotein E-deficient mice. *Circulation.* 2001;103:2277-2282.

Dansky HM, Barlow CB, Lominska C, Sikes JL, Kao C, Weinsaft J, Cybulsky MI, Smith JD. Adhesion of monocytes to arterial endothelium and initiation of atherosclerosis are critically dependent on vascular cell adhesion molecule-1 gene dosage. *Arterioscler Thromb Vasc Biol* 2001;21:1662-1667.

Dansky HM, Charlton SA, Barlow CB, Tamminen M, Smith JD, Frank JS, Breslow JL. Apo A-I inhibits foam cell formation in Apo E-deficient mice after monocyte adherence to endothelium. *J Clin Invest.* 1999;104:31-39.

Datta et al. Effects of Increasing Hydrophobicity on the Physical-Chemical and Biological Properties of a Class A Amphipathic Helical Peptide. *J Lipid Research* 42:1096-1104, 2001.

Davenport P, Tipping PG. The role of interleukin-4 and interleukin-12 in the progression of atherosclerosis in apolipoprotein E-deficient mice. *Am J Pathol* 2003;163:1117-1125.

Davies MJ, Gordon JL, Gearing AJ, Pigott R, Woolf N, Katz D, Kyriakopoulos A. The expression of the adhesion molecules ICAM-1, VCAM-1, PECAM, and Eselectin in human atherosclerosis. *J Pathol* 1993;171:223-229.

De Caterina R, Bernini W, Carluccio MA, Liao JK, Libby P. Structural requirements for inhibition of cytokine-induced endothelial activation by unsaturated fatty acids. *J. Lipid Res.* 1998;39:1062-1070.

Diederich et al. "Apolipoprotein AI and $HDL_3$ Inhibit Spreading of Primary Human Monocytes through a Mechanism that Involves Cholesterol Depletion and Regulation of CD42" *Atherosclerosis* 159:313-324, 2001.

Dimayuga P, Zhu J, Oguchi S, Chyu KY, Xu XO, Yano J, Shah PK, Nilsson J, Cercek B. Reconstituted HDL containing human apolipoprotein A-1 reduces VCAM-1 expression and neointima formation following periadventitial cuffinduced carotid injury in apoE null mice. *Biochem Biophys Res Commun.* 1999;264:465-468.

Dooley et al. "An All D-Amino Acid Opioid Peptide with Central Analgesic Activity from a Combinatorial Library" *Science* 2019-2022, 1994.

Epand RM, Stafford A, Leon B, Lock PE, Tytler EM, Segrest JP, Anantharamaiah GM. HDL and apolipoprotein A-I protect erythrocytes against the generation of procoagulant activity. *Arterioscler. Thromb.* 1994;14:1775-1783.

Fleisher LN, Tall AR, Witte LD, Miller RW, Cannon PJ. Stimulation of arterial endothelial cell prostacyclin synthesis by high density lipoproteins. *J. Biol. Chem.* 1982;257:6653-6655.

Fogelman AM, Shechter I, Seager J, Hokom M, Child JS, Edwards PA. Malondialdehyde alteration of low density lipoproteins leads to cholesteryl ester accumulation in human monocyte-macrophages. *Proc Natl Acad Sci U S A.* 1980;77:2214-2218.

Fogelman AM. When good cholesterol goes bad. Nat Med 2004;10:902-903.

Forte TM, Subbanagounder G, Berliner JA, Blanche PJ, Clermont AO, Jia Z, Oda MN, Krauss RM, Bielicki JK. Altered activities of anti-atherogenic enzymes LCAT, paraoxonase, and platelet-activating factor acetylhydrolase in atherosclerosis-susceptible mice. *J. Lipid Res.* 2002;43:477-485.

Fricker et al. "Enteral Absorption of Octreotide: Modulation of Intestinal Permeability by Distinct Carbohydrates" *The Journal of Pharmacology and Experimental Therapeutics* 274:826-832, 1995.

Fuessl et al. "Oral Absorption of the Somatostatin Analogue SMS 201-995: Theoretical and Practial Implications" *Clinical Science* 72: 255-257, 1987.

Gabay C, Kushner I. Acute-phase proteins and other systemic responses to inflammation. *N. Engl. J. Med.* 1999; 340: 448-454.

Garner B, Waldeck AR, Witting PK, Rye KA, Stocker R. Oxidation of high density lipoproteins. II. Evidence for direct reduction of lipid hydroperoxides by methionine residures of apolipoproteins AI and AII. *J Biol Chem* 1998;273:6088-6095.

Garner B, Witting PK, Waldeck AR, Christison JK, Raftery M, Stocker R. Oxidation of high density lipoproteins. I. Formation of methionine sulfoxide in apolipoproteins AI and AII is an early event that accompanies lipid peroxidation and can be enhanced by alpha-tocopherol. *J Biol Chem* 1998;273:6080-6087.

Gaut JP, Byun J, Tran HD, Lauber WM, Carroll JA, Hotchkiss RS, Belaaouaj A, Heinecke JW. Myeloperoxidase produces nitrating oxidants in vivo. *J Clin Invest* 2002;109:1311-1319.

George J, Afek A, Shaish A, Levkovitz H, Bloom N, Cyrus T, Zhao L, Funk CD, Sigal E, Harats D. 12/15-lipoxygenase gene disruption attenuates atherogenesis in LDL receptor-deficient mice. *Circulation.* 2001;104:1646-1650.

Gordon T, Castelli WP, Hjortland MC, et al. High density lipoprotein as a protective factor against coronary heart disease. *Am. J. Med.*1977;62: 707-714.

Gurfinkel et al. "Influenza Vaccine Pilot Study in Acute Coronary Syndromes and Planned Percutaneous Coronary Interventions. The FLU Vaccination Acute Coronary Syndromes (FLUVACS) Study" *Circulation* 105:2143-2147, 2002.

Hamase et al. "Determination of Free D-Proline and D-Leucine in the Brains of Mutant Mice Lacking D-Amino Acid Oxidase Activity" *Analytical Biochemistry* 298:253-258, 2001.

Harats D, Shaish A, George J, Mulkins M, Kurihara H, Levkovitz H, Sigal E. Overexpression of 15-lipoxygenase in vascular endothelium accelerates early atherosclerosis in LDL receptor-deficient mice. *Arterioscler Thromb Vasc Biol.* 2000;20:2100-2105.

Hardy et al. "An Automated High-Performance Liquid Chromatography Procedure for the Quantitation of L- and D-Amino Acids by Means of Stepwise Precolumn Derivatization" Analytical Biochemistry 291:297-299, 2001.

Hauser et al. "Identification of a Receptor Mediating Absorption of Dietary Cholesterol in the Intestine" *Biochemistry* 178423-17850, 1998.

Henricksen T, Mahoney EM, Steinberg D. Enhanced macrophage degradation of low density lipoprotein previously incubated with cultured endothelial cells: recognition by receptor for acetylated low density lipoproteins. *Proc Natl Acad Sci* U S A. 1981;78-6499-6503.

Hessler JR, Robertson AL, Chisolm GM. LDL-induced cytotoxicity and its inhibition by HDL in human vascular smooth muscle and endothelial cells in culture. *Atherosclerosis* 1979; 32:213-229.

Hwang SJ, Ballantyne CM, Sharrett AR, Smith LC, Davis CE, Gotto AM Jr, Boerwinkle E. Circulating adhesion molecules VCAM-1, ICAM-1, and E-selectin in carotid atherosclerosis and incident coronary heart disease cases. The atherosclerosis risk in communities (ARIC) study. *Circulation* 1997;96:4219-4225.

Hyka et al. "Apolipoprotein A-I Inhibits the Production of Interleukin-1β and Tumor Necrosis Factor-α by Blocking Contact-Mediated Activation of Monocytes by T Lymphocytes" Blood 97:2381-2389, 2001.

Jin W, Millar JS, Broedl U, et al. Inhibition of endothelial lipase causes increased HDL cholesterol levels in vivo. J Clin Invest 2003;111:357-362.

Jones et al. "Computer Programs to Identify and Classify Amphipathic α Helical Domains" Journal of Lipid Research 33:287-296, 1992.

Karle, I., Gopi, H., and Balaram, P. Crystal structure of hydrophobic 19-residue peptide helix containing three centrally located D amino acids PNAS 2003;100:24:13946-13951.

Karle, I, Prasad, S. and Balaram, P. A combined extented and helical backbone for Boc-(Ala-Leu-Ac7C)2-OME, Peptides Res. 2004; 63:174-180.

Ko Y, Haring R, Stiebler H, Wieczorek AJ, Vetter H, Sachinidis A. Highdensity lipoprotein reduces epidermal growth factor-induced DNA synthesis in vascular smooth muscle cells. Atherosclerosis 1993;99: 253-259.

Kullman et al.) "Evaluation of the Enantiomeric Composition of Amino Acids in Tobacco" Chirality 11:669-673, 1999.

Kume N, Cybulsky MI, Gimbrone Jr MA. Lysophosphatidylcholine, a component of atherogenic lipoproteins, induces mononuclear leukocyte adhesion molecules in cultured human and rabbit arterial endothelial cells. Journal of Clincial Investigation 1992;90:1138-1144.

Lawrence MB, Springer TA. Leukocytes roll on a selectin at physiologic flow rates: distinction from and prerequisite for adhesion through integrins. Cell 1991;65:859-873.

Lee SH, Oe T, Blair IA. Vitamin C-induced decomposition of lipid hydroperoxides to endogenous genotoxins. Science 2001;292:2083-2086.

Levine DM, Parker TS, Donnelly TM, Walsh A, Rubin AL. In vivo protection against endotoxin by plasma high density lipoprotein. Proc. Natl. Acad. Sci. USA 1993:90 : 12040-12044.

Li H, Cybulsky MI, Gimbrone MA, Jr., Libby P. An atherogenic diet rapidly induces VCAM-1, a cytokine-regulatable mononuclear leukocyte adhesion molecule, in rabbit aortic endothelium. Arteriosclerosis and Thrombosis 1993;13:197-204.

Libby P, Ridker PM, Maseri A. Inflammation and atherosclerosis. Circulation 2002;105:1135-1143.

Lundin et al. "Absorption of Intragastrically Administered DDAVP in Conscious Dogs" Life Sciences 38:703-709, 1986.

Mehrabian M, Allayee H, Wong J, Shi W, Wang XP, Shaposhnik Z, Funk CD, Lusis AJ, Shih W. Identification of 5-lipoxygenase as a major gene contributing to atherosclerosis susceptibility in mice. Circ Res. 2002;91:120-126.

Merrifield et al. "Retro and Retroenantio Analogs of Cecropin-Melittin Hybrids" Proc Natl Acad Sci USA 92: 3449-3453, 1995.

Murugesan G, Sa G, Fox PL. High-density lipoprotein stimulates endothelial cell movement by a mechanism distinct from basic fibroblast growth factor. Circ. Res. 1994;74 : 1149-1156.

Nanjee MN, Doran JE, Lerch PG, Miller NE. Acute effects of intravenous infusion of apoA-I/phosphosphatidycholine discs on plasma lipoproteins in humans.. Arterioscler Thromb Vasc Biol. 1999;19:979-989.

Nanjee MN, Cooke CJ, Garvin R, et al. Intravenous apoA-I/lecithin discs increase pre-b-HDL concentration in tissue fluid and stimulate reverse cholesterol transport in humans. J Lipid Res 2001;42:1586-1593.

Navab et al. "Oral Administration of an Apo A-I Mimetic Peptide Synthesized from D-Amino Acids Dramatically Reduces Atherosclerosis in Mice Independent of Plasma Cholesterol" Circulation 105: 290-292, 2002.

Navab M, Anantharamaiah GM, Reddy ST, et al. The oxidation hypothesis of atherogenesis: the role of oxidized phospholipids and HDL. J. Lipid Res. 2004; 45: 993-1007.

Navab M, Anantharamaiah GM, Reddy ST, et al. Oral D-4F causes formation of pre-□ high-density lipoprotein and improves high-density lipoprotein-mediated cholesterol efflux and reverse cholesterol transport from macrophages in apoE-null mice. Circulation 2004;109:r120-r125.

Navab M, Berliner JA, Subbanagounder G, Hama S, Lusis AJ, Castellani LW, Reddy S, Shih D, Shi W, Watson AD, Van Lenten BJ, Vora D, Fogelman AM. HDL and the inflammatory response induced by LDL-derived oxidized phospholipids. Arterioscler Thromb Vasc Biol 2001;21:481-488.

Navab M, Hama S, Hough G et al. Oral synthetic phospholipids (DMPC) raises high-density lipoprotein cholesterol levels, improves high-density lipoprotein function, and markedly reduces atherosclerosis in apolipoprotein E-null mice. Circulation 2003;108:1735-1739.

Navab M, Hama SY, Hough GP, et al. A cell-free assay for detecting HDL that is dysfunctional in preventing the formation of or inactivating oxidized phospholipids. J Lipid Res 2001;42:1308-1317.

Navab M, Hama-Levy, S, Van Lenten BJ, et al. Mildly oxidized LDL induces an increased apolipoprotein J/paraoxonase ratio. J. Clin. Invest. 1997; 99: 2005-2019.

Navab M, Imes SS, Hama SY, Hough GP, Ross LA, Bork RW, Valente AJ, Berliner JA, Drinkwater DC, Laks H,, et al. Monocyte transmigration induced by modification of low density lipoprotein in cocultures of human aortic wall cells is due to induction of monocyte chemotactic protein 1 synthesis and is abolished by high density lipoprotein. Journal of Clinical Investigation 1991;88:2039-2046.

Nievelstein PF, Fogelman AM, Mottino G, Frank JS. Lipid accumulation in rabbit aortic intima two hours after bolus infusion of low density lipoprotein: A deep-etch and immuno-localization study of ultra-rapidly frozen tissue. Arteriosclerosis and Thrombosis 1991;11:1795-1805.

Lumsden AB, Chen C, Hughes JD, Kelly AB, Hanson SR, Harker LA. Anti- VLA-4 antibody reduces intimal hyperplasia in the endarterectomized carotid artery in nonhuman primates. J Vasc Surg 1997;26:87-93.

Mach F, Schonbeck U, Sukhova GK, Atkinson E, Libby P. Reduction of atherosclerosis in mice by inhibition of CD40 signalling. Nature 1998;394:200-203.

O'Brien KD, McDonald TO, Chait A, Allen MD, Alpers CE. Neovascular expression of E-selectin, intercellular adhesion molecule-1, and vascular cell adhesion molecule-1 in human atherosclerosis and their relation to intimal leukocyte content. Circulation 1996;93:672-82.

O'Connell BJ, Genest J Jr. High-density lipoproteins and endothelial function. Circulation 2001;104:1978-1983.

Oguchi S, Dimayuga P, Zhu J, Chyu KY, Yano J, Shah PK, Nilsson J, Cercek B. Monoclonal antibody against vascular cell adhesion molecule-1 inhibits neointimal formation after periadventitial carotid artery injury in genetically hypercholesterolemic mice. Arterioscler Thromb Vasc Biol 2000;20:1729-1736.

Owens et al. "Apolipoprotein A-I and its Amphipathic Helix Peptide Analogues Inhibit Human Immunodeficiency Virus-Induced Syncytium Formation" J Clin Invest 86: 1142-1150, 1990.

Panizzutti et al. "A New Strategy to Decrease N-methyl-D-aspartate (NMDA) Receptor Coactivation: Inhibition of D-serine Synthesis by Converting Serine Racemase into an Eliminase" PNAS 98:5294-5299, 2001.

Papo N, Oren Z, Pag U, et al. The consequence of sequence alteration of an amphipathic □-helical antimicrobial peptide and its diastereomers. J. Biol. Chem. 2002;277(37): 33913-33921.

Pappenheimer et al. "Intestinal Absorption and Excretion of Octapeptides Composed of D Amino Acids" Proc Natl Acad Sci USA 91: 1942-1945, 1999.

Parthasarathy S, Santanam N. Mechanisms of oxidation antioxidants, and atherosclerosis. Curr Opin Lipidol 1994;5:371-375.

Pasceri V, Cheng JS, Willerson JT, Yeh ET, Chang J. Modulation of Creactive protein-mediated monocyte chemoattractant protein-1 induction in human endothelial cells by anti-atherosclerosis drugs. Circulation. 2001;103:2531-2534.

Pasceri V, Willerson JT, Yeh ET. Direct proinflammatory effect of C-reactive protein on human endothelial cells. Circulation. 2000;102:2165-2168.

Peng et al. "Effects of L-glutamate, D-aspartate, and Monensin on Glycolytic and Oxidative Glucose Metabolism in Mouse Astrocyte Cultures: Further Evidence that Glutamate Uptake is Metabolically Driven by Oxidative Metabolism" *Neurochemistry International* 38:437-443, 2001.

Ou J, Geiger T, Zhijun O, et al. AP-4F, antennapedia peptide linked to an amphipathic □ helical peptide, increases the efficiency of lipofectamine-mediated gene transfection in endothelial cells. *Biochem Biophys Res Commun* 2003;305:605-610.

Ou J, Ou Z, Jones DW, et al. L-4F, an apolipoprotein A-I mimetic, dramatically improves vasodilation in hypercholesterolemic and sickle cell disease. *Circulation* 2003;107:2337-2341.

Ou Z, Ou J, Ackerman AW et al. L-4F, an apolipoprotein A-I mimetic, restores nitric oxide and superoxide anion balance in low-density lipoprotein-treated endothelial cells. *Circulation* 2003;107:1520-1524.

Ranganathan, D, Kurur, S, Kunwar, A, Sarma, A, Vairamani, M, Karle, I. Channel-forming, self-assembling, bishelical amphiphilic peptides: design, synthesis and crystal structure of Py(Aibn)21 n=2, 3, 4. J. Peptide Res. 2000 56:416-426.

Reape TJ, Groot PH. Chemokines and atherosclerosis. *Atherosclerosis* 1999;147:213-225.

Reddy ST, Wadleigh DJ, Grijalva V, Ng C, Hama S, Gangopadhyay A, Shih DM, Lusis AJ, Navab M, Fogelman AM. Human paraoxonase-3 is an HDLassociated enzyme with biological activity similar to paraoxonase-1 protein but is not regulated by oxidized lipids. *Arterioscler Thromb Vasc Biol* 2001;21:542-547.

Reddy ST, Nguyen JT, Grijalva V, et al. Potential role for mitogen-activated protein kinase phosphatase-1 in the development of atherosclerotic lesions in mouse models. *Arterioscler Thromb Vasc Biol* 2004;24:1676-1681.

Ridker PM. On evolutionary biology, inflammation, infection, and the causes of atherosclerosis. *Circulation* 2002;105:2-4.

Rong JX, Li J, Reis ED, Choudhury RP, Dansky HM, Elmalem VI, Fallon JT, Breslow JL, Fisher EA. Elevating high-density lipoprotein cholesterol in apolipoprotein E-deficient mice remodels advanced atherosclerotic lesions by decreasing macrophage and increasing smooth muscle cell content. *Circulation* 2001;104:2447-2452.

Sattler W, Stocker R. Greater selective uptake by Hep G2 cells of highdensity lipoprotein cholesteryl ester hydroperoxides than of unoxidized cholesteryl esters. *Biochem J.* 1993;294:771-778.

Segrest et al. "The Amphipathic Helix in the Exchangeable Apolipoproteins: A Review of Secondary Structure and Function" *J Lipid Research* 33:141-166, 1992.

Shah PK, Nilsson J, Kaul S. Effects of recombinant apolipoprotein A-I(Milano) on aortic atherosclerosis in apolipoprotein E-deficient mice. *Circulation*, 1998:97(8): 780-785, 1998.

Shah PK, Yano J, Reyes O, Chyu KY, Kaul S, Bisgaier CL, Drake S, Cercek B. High-dose recombinant apolipoproteins A-IMilano mobilizes tissue cholesterol and rapidly reduces plaque lipid and macrophage content in apolipoprotein Edeficient mice: potential implications for acute plaque stabilization. *Circulation.* 2001;103:3047-3050.

Shih D.M., Xia Y-R., Wang X-P., Miller E., Castellani L.W., Subbanagounder G., Cheroutre H., Faull K., Berliner J.A., Witztum J. L., Lusis A.J. Combined serum paraoxonase/apolipoprotein E knockout mice exhibit increased lipoprotein oxidation and atherosclerosis. *J. Biol. Chem.*, 2000;275:17527-17535.

Shih PT, Elices MJ, Fang ZT, Ugarova TP, Strahl D, Territo MC, Frank JS, Kovach NL, Cabanas C, Berliner JA, Vora DK. Minimally modified low-density lipoprotein induces monocyte adhesion to endothelial connecting segment-1 by activating beta integrin. *J Clin Invest* 1999;103:613-625.

Shishehbor MH, Aviles RJ, Brennan ML, Fu X, Goormastic M, Pearce GL, Gokce N, Keaney JF Jr. Penn MS, Sprecher DL, Vita JA, Hazen SL. Association of nitrotyrosine levels with cardiovascular disease and modulation by statin therapy. *JAMA* 2003:289:1675-1680.

Sing et al. "Innate Defences Against Viraemia" *Rev Med Virol* 10:395-403, 2000.

Singh IP, Baron S. Innate defences against viremia. *Rev Med Virol* 2000;10:395-403.

Sorescu D, Szocs K, Griendling KK. NAD(P)H oxidases and their relevance to atherosclerosis. *Trends Cardiovas Med* 2001;11:124-131.

Spieker LE, Sudano I, Hurlimann D, Lerch PG, Lang MG, Binggeli C, Corti R, Ruschitzka F, Luscher TF, Noll G. High-density lipoprotein restores endothelial function in hypercholesterolemic men. *Circulation.* 2002;105:1399-1402.

Springer TA. Adhesion receptors of the immune system. *Nature* 1990;346:425-434.

Srinivas et al. "Antivrial Effects of Apolipoprotein A-I and Its Synthetic Amphipathic Peptide Analogs" *Virology* 176:48-57, 1990.

Stannard AK, Khan S, Graham A, Owen JS, Allen SP. Inability of plasma high-density lipoproteins to inhibit cell adhesion molecule expression in human coronary artery endothelial cells. *Atherosclerosis* 2001;154:31-38.

Sugatani J, Miwa M, Komiyama Y, Ito S. High-density lipoprotein inhibits the synthesis of platelet-activating factor in human vascular endothelial cells. *J. Lipid Mediators Cell Signal.* 1996:13:73-88.

Tsao et al.) "Hibernation-induction Peptide and Cell Death: [D-Ala$^2$, D-Leu$^5$]enkephalin Blocks Bax-related Apoptotic Processes" *European Journal of Pharmacology* 428:149-151, 2001.

Tward A, Xia YR, Wang XP, Shi YS, Park C, Castellani LW, Lusis AJ, Shih DM. Decreased atherosclerotic lesion formation in human serum paraoxonase transgenic mice. *Circulation* 2002;106:484-490.

Van Lenten et al. "Acute Influenza A Infection Promotes Increased Macrophage Infiltration into the Artery Wall that is Prevented by Apolipoprotein A-I" *Circulation* 104(suppl II):II-470. Abstract, not dated.

Van Lenten BJ, Hama SY, de Beer FC, Stafforini DM, McIntyre TM, Prescott SM, La Du BN, Fogelman AM, Navab M. Anti-inflammatory HDL becomes proinflammatory during the acute phase response. Loss of protective effect of HDL against LDL oxidation in aortic wall cell cocultures. *J Clin Invest* 1995;96:2758-2767.

Van Lenten BJ, Wagner AC, Nayak DP, Hama S, Navab M, Fogelman AM. High-density lipoprotein loses its anti-inflammatory properties during acute influenza A infection. Circulation 2001;103:2283-2288.

Van Lenten BJ, Wagner AC, Anantharamaiah GM, Garber DW, Fishbein MC, Adhikary L, Nayak DP, Hama S, Navab M, Fogelman AM. Influenza infection promotes macrophage traffic into arteries of mice that is prevented by D-4F, an apolipoprotein A-I mimetic peptide. *Circulation* 2002; 106:1127-1132.

Venugopal SK, Devaraj S, Yuhanna I, Shaul P, Jialal I. Demonstration that C-reactive protein decreases eNOS expression and bioactivity in human aortic endothelial cells. *Circulation.* 2002;106:1439-1441.

Walpola PL, Gotlieb AI, Cybulsky MI, Langille BL. Expression of ICAM-1 and VCAM-1 and monocyte adherence in arteries exposed to altered shear stress. *Arterioscler Thromb Vasc Biol* 1995;15:2-10.

Watson AD, Navab M, Hama SY, Sevanian A, Prescott SM, Stafforini DM, McIntyre TM, Du BN, Fogelman AM, Berliner JA. Effect of platelet activating factor-acetylhydrolase on the formation and action of minimally oxidized-low density lipoprotein. *J Clin Invest* 1995;95:774-782.

Watson AD, Berliner JA, Hama SY, et al. Protective effect of high density lipoprotein associated paraoxonase. Inhibition of the biological activity of minimally oxidized low density lipoprotein. *J Clin Invest* 1995;96:2882-2891.

Xia P, Vadas MA, Rye KA, Barter PJ, Gamble JR High density lipoproteins (HDL) interrupt the sphingosine kinase signaling pathway. A possible mechanism for protection against atherosclerosis by HDL. *J Biol Chem.* 1999;274:33143-33147.

Yamashita S, Maruyama T, Hirano K, et al. Molecular mechanisms, lipoprotein abnormalities and atherogenicity of hyperalphalipoproteinemia. *Atherosclerosis* 2000;152:271-285.

Yan D, Navab M, Bruce C et al. PLTP deficiency improves the anti-inflammatory properties of HDL and reduces the ability of LDL to induce monocyte chemotactic activity. *J Lipid Res* 2004;45:1852-1858.

Yui Y, Aoyama T, Morishita H, Takahashi M, Takatsu Y, Kawai C. Serum prostacyclin stabilizing factor is identical to apolipoprotein A-I (Apo A-I). A novel function of Apo A-I. *J. Clin. Invest*. 1988;82: 803-807.

Zeiher AM, Schachinger V. Hohnloser SH, et al. Coronary atherosclerotic wall thickening and vascular reactivity in humans. Elevated high-density lipoprotein levels ameliorate abnormal vasoconstriction in early atherosclerosis. *Circulation* 1994;89:2525-2532.

Zhang R, Brennan ML, Shen Z, MacPherson JC, Schmitt D, Molenda CE, Hazen SL. Myeloperoxidase functions as a major enzymatic catalyst for initiation of lipid peroxidation at sites of inflammation. *J Biol Chem* 2002;277:46116-46122.

Zhang WJ, Stocker R, McCall MR, Forte TM, Frei B. Lack of inhibitory effect of HDL on TNFalpha-induced adhesion molecule expression in human aortic endothelial cells. *Atherosclerosis* 2002;165:241-249.

Zhao L, Cuff CA, Moss e, Willie U, Cyrus T, Klein EA, Pratico D, Radar DJ, Hunter CA, Pure E, Funk CD. Selective interleukin-12 synthesis defect in 12/15-lipoxygenase deficient macrophages associated with reduced atherosclerosis in a ouse model of familial hypercholesterolemia. *J Biol Chem* 2002;277:35350-35356.

* cited by examiner

US 7,148,197 B2

ORALLY ADMINISTERED SMALL PEPTIDES SYNERGIZE STATIN ACTIVITY

CROSS-REFERENCE TO RELATED APPLICATIONS

This application claims benefit of and priority to U.S. Ser. No. 60/494,449, filed on Aug. 11, 2003, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported by United States Public Health Service and National Heart, Lung, and Blood Institute Grants HL30568 and HL34343. The Government of the United States of America may have certain rights in this invention.

FIELD OF THE INVENTION

This invention relates to the field of atherosclerosis. In particular, this invention pertains to the identification of a class of peptides that are orally administrable and that ameliorate one or more symptoms of atherosclerosis.

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

Epidemiological studies show an inverse correlation of high density lipoprotein (HDL) and apolipoprotein (apo) A-I levels with the occurrence of atherosclerotic events (Wilson et al. (1988) *Arteriosclerosis* 8: 737–741). Injection of HDL into rabbits fed an atherogenic diet has been shown to inhibit atherosclerotic lesion formation (Badimon et al. (1990) *J. Clin. Invest.* 85: 1234–1241).

Human apo A-I has been a subject of intense study because of its anti-atherogenic properties. Exchangeable apolipoproteins, including apo A-I, possess lipid-associating domains (Brouillette and Anantharamaiah (1995) *Biochim. Biophys. Acta* 1256:103–129; Segrest et al. (1974) *FEBS Lett.* 38: :247–253). Apo A-I has been postulated to possess eight tandem repeating 22mer sequences, most of which have the potential to form class A amphipathic helical structures (Segrest et al. (1974) *FEBS Lett.* 38: :247–253). Characteristics of the class A amphipathic helix include the presence of positively charged residues at the polar-nonpolar interface and negatively charged residues at the center of the polar face (Segrest et al. (1974) FEBS Lett. 38: 247–253; Segrest et al. (1990) *Proteins: Structure, Function, and Genetics* 8: 103–117). Apo A-I has been shown to strongly associate with phospholipids to form complexes and to promote cholesterol efflux from cholesterol-enriched cells. The delivery and maintenance of serum levels of apo A-I to effectively mitigate one or more symptoms of atherosclerosis has heretofore proven elusive.

SUMMARY OF THE INVENTION

This invention provides novel peptides administration of which mitigates one or more symptoms of atherosclerosis and other inflammatory conditions such as rheumatoid arthritis, lupus erythematous, polyarteritis nodosa, osteoporosis, Alzheimer's disease, congestive heart failure, endothelial dysfunction, viral illnesses such as influenza A, and diseases such as multiple sclerosis. In particular, it was a discovery of this invention that peptides comprising a class A amphipathic helix when formulated with "D" amino acid residue(s) and/or having protected amino and carboxyl termini can be orally administered to an organism, are readily taken up and delivered to the serum, and are effective to mitigate one or more symptoms of atherosclerosis. In certain embodiments, the peptides can be formulated with all "L" amino acid residues and are still effective, particular when administered by routes other than oral administration.

It was also a discovery that "small" peptides (e.g. ranging in length from three amino acides to about 11 amino acids) having hydrophobic terminal amino acids or terminal amino acids rendered hydrophobic by one or more hydrophobic blocking goups and having internal acidic and/or basic, and/or aliphatic, and/or aromatic amino acids as described herin are also capable of mitigating one or more symptoms of atherosclerosis or other pathologies characterized by an inflammatory response.

The peptides of this invention are typically effective to stimulate the formation and cycling of pre-beta high density lipoprotein-like particles and/or to promote lipid transport and detoxification.

The peptides described herein are also effective for preventing the onset or inhibiting or eliminating one or more symptoms of osteoporosis.

It was also a surprising discovery that the peptides can be used to enhance (e.g. synergically enhance) the activity of statins and/or Ezetimibe or other cholesterol uptake inhibitors, thereby permitting the effective use of statins or cholesterol uptake inhibitors at lower dosages and/or cause the statins or cholesterol uptake inhibitors to be significantly more anti-inflammatory at any given dose.

In certain embodiments, this invention provides peptides or a combination of peptides that ameliorates one or more symptoms of an inflammatory condition (e.g. atherosclerosis atherosclerosis, rheumatoid arthritis, lupus erythematous, polyarteritis nodosa, osteoporosis, Altzheimer's disease, a viral illnesses, etc.). Certain preferred peptides are characterized by the formula: $X^1-X^2-X^3_n-X^4$ where n is 0 or 1; $X^1$ is a hydrophobic amino acid and/or bears a hydrophobic protecting group; $X^4$ is a hydrophobic amino acid and/or bears a hydrophobic protecting group; and, when n is 0, $X^2$ is an amino acid selected from the group consisting of an acidic amino acid, a basic amino acid, and a histidine; and, when when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid. Certain preferred peptides convert pro-inflammatory HDL to anti-inflammatory HDL or make anti-inflammatory HDL more anti-inflammatory. In certain embodiments, the peptide does not have the amino acid sequence Lys-Arg-Asp-Ser (SEQ ID NO:238) in which Lys, Arg, Asp, and Ser are all L amino acids. Peptides of this invention include peptides according to the formula above, and/or peptides comprising a peptide of the formula above and/or concatamers of such peptides.

In certain embodiments, $X^1$ and $X^4$ are independently selected from the group consisting of alanine (Ala), valine (Val), leucine (Leu), isoleucine (Ile), proline (Pro), phenylalanine (Phe), tryptophan (Trp), methionine (Met), serine (Ser) bearing a hydrophobic protecting group, beta-naphthyl alanine, alpha-naphthyl alanine, norleucine, cyclohexylalanine, threonine (Thr) bearing a hydrophobic protecting group, tyrosine (Tyr) bearing a hydrophobic protecting group, lysine (Lys) bearing a hydrophobic protecting group, arginine (Arg) bearing a hydrophobic protecting group, ornithine (Orn) bearing a hydrophobic protecting group, aspartic acid (Asp) bearing a hydrophobic protecting group, cysteine (Cys) bearing a hydrophobic protecting group, and glutamic acid (Glu) bearing a hydrophobic protecting group.

In certain embodiments, the peptide is a tri-mer (i.e., n is 0). In certain trimers, $X^1$ is Glu, Leu, Lys, Orn, Phe, Trp, or norLeu; $X^2$ is acidic (e.g. aspartic acid, glutamic acid, etc.), or basic (e.g. lysine, arginine, histidine, etc.) and $X^4$ is Ser, Thr, Ile, Leu, Trp, Tyr, Phe, or norleu. In certain embodiments, the peptide comprises the amino acid sequence of a peptide listed in Table 3. In certain embodiments, the peptide is a protected trimer as shown in Table 3.

In certain embodiments, n is 1 and the peptide is or comprises a tetramer in which $X^2$ and $X^3$ are independently an acidic amino acid or a basic amino acid such that when $X^2$ is an acidic amino acid, $X^3$ is a basic amino acid and when $X^2$ is a basic amino acid, $X^3$ is an acidic amino acid. $X^1$ and $X^4$ can include independently selected amino acids, e.g., as indicated above. In certain embodiments, $X^2$ and $X^3$ are independently selected from Asp, Glu, Lys, Arg, and His. In certain embodiments, the peptide comprises the amino acid sequence of a peptide listed in Table 4. In certain embodiments, the peptide is a protected tetramer as show in Table 4.

In still another embodiment, n is 1 and the peptide is or comprises a tetramer in which $X^2$ and $X^3$ are independently an acidic, a basic, or a aliphatic amino acid with one of $X^2$ or $X^3$ being an acidic or a basic amino acid such that when $X^2$ is an acidic or a basic amino acid, $X^3$ is an aliphatic amino acid; and when $X^3$ is an acid or a basic amino acid, $X^2$ is an aliphatic amino acid. $X^1$ and $X^4$ can include independently selected amino acids, e.g., as indicated above. In certain embodiments, $X^2$ and $X^3$ are independently selected from the group consisting of Asp, Glu, Lys, Arg, His, and Ile, more preferably from the group consisting of Asp, Arg, Leu, and Glu. In certain embodiments, the peptide comprises the amino acid sequence of a peptide listed in Table 5. In certain embodiments, the peptide is a protected tetramer as show in Table 5.

In another embodiment, n is 1 and the peptide is or comprises a tetramer in which $X^2$, $X^3$ are independently an acidic, a basic, or an aromatic amino acid with one of $X^2$ or $X^3$ being an acidic or a basic amino acid such that when $X^2$ is an acidic or a basic amino acid, $X^3$ is an aromatic amino acid; and when $X^3$ is an acid or a basic amino acid, $X^2$ is an aromatic amino acid. $X^1$ and $X^4$ can include independently selected amino acids, e.g., as indicated above. In certain embodiments, $X^2$ and $X^3$ are independently selected from the group consisting of Asp, Arg, Glu, Trp, Tyr, Phe, and Lys. In certain embodiments, the peptide comprises the amino acid sequence of a peptide listed in Table 6. In certain embodiments, the peptide is a protected tetramer as show in Table 6.

This invention also provides for peptides that are or comprise a pentamer (5-mer) characterized by the formula: $X^1-X^2-X^3-X^4-X^5$, where $X^1$ is a hydrophobic amino acid and/or bears a hydrophobic protecting group; $X^5$ is a hydrophobic amino acid and/or bears a hydrophobic protecting group; and $X^2$, $X^3$, and $X^4$ are independently selected aromatic amino acids or histidine; and the peptide converts pro-inflammatory HDL to anti-inflammatory HDL or makes anti-inflammatory HDL more anti-inflammatory. In certain embodiments, $X^1$ and $X^5$ are independently selected from the group consisting of alanine (Ala), valine (Val), leucine (Leu), isoleucine (Ile), proline (Pro), phenylalanine (Phe), tryptophan (Trp), methionine (Met), phenylalanine (Phe), tryptophan (Trp), methionine (Met), serine (Ser) bearing a hydrophobic protecting group, beta-naphthyl alanine, alpha-naphthyl alanine, norleucine, cyclohexylalanine, threonine (Thr) bearing a hydrophobic protecting group, tyrosine (Tyr) bearing a hydrophobic protecting group, lysine (Lys) bearing a hydrophobic protecting group, arginine (Arg) bearing a hydrophobic protecting group, ornithine (Orn) bearing a hydrophobic protecting group, aspartic acid (Asp) bearing a hydrophobic protecting group, cysteine (Cys) bearing a hydrophobic protecting group, and glutamic acid (Glu) bearing a hydrophobic protecting group. In certain embodiments $X^2$, $X^3$, and $X^4$ are independently is selected from the group consisting of Phe, Val, Trp, Tyr, and His. In certain embodiments, the peptide comprises the amino acid sequence of a peptide listed in Table 7. In certain embodiments, the peptide is a protected tetramer as show in Table 7.

This invention also provides for larger peptides that ameliorate one or more symptoms of an inflammatory condition. In certain embodiments, the peptide ranges in length from 5 to 11 amino acids; the terminal amino acids are hydrophobic amino acids and/or bear hydrophobic protecting groups; the non-terminal amino acids form at least one acidic domain and at least one basic domain; and the peptide converts pro-inflammatory HDL to anti-inflammatory HDL or makes anti-inflammatory HDL more anti-inflammatory.

In certain embodiments, the peptide ranges in length from 5 to 11 amino acids; the terminal amino acids are hydrophobic amino acids and/or bear hydrophobic protecting groups; the non-terminal amino acids form at least one acidic domain or one basic domain and at least one aliphatic domain; and the peptide converts pro-inflammatory HDL to anti-inflammatory HDL or makes anti-inflammatory HDL more anti-inflammatory.

In other embodiments, the peptide ranges in length from 5 to 11 amino acids; the terminal amino acids are hydrophobic amino acids and/or bear hydrophobic protecting groups; the non-terminal amino acids form at least one acidic domain or one basic domain and at least one aromatic domain; and the peptide converts pro-inflammatory HDL to anti-inflammatory HDL or makes anti-inflammatory HDL more anti-inflammatory.

In still other embodiments, the peptide ranges in length from 6 to 11 amino acids; the terminal amino acids are hydrophobic amino acids and/or bear hydrophobic protecting groups; the non-terminal amino acids form at least one aromatic domain or two or more aromatic domains separated by one or more histidines; and the peptide converts pro-inflammatory HDL to anti-inflammatory HDL or makes anti-inflammatory HDL more anti-inflammatory.

This invention also provides for peptides that ameliorate one or more symptoms of an inflammatory condition and that comprise one or more amphipathic helices. Thus, this invention includes a peptide or a concatamer of a peptide that ranges in length from about 10 to about 30 amino acids; that comprises at least one class A amphipathic helix; that comprises one or more aliphatic or aromatic amino acids at the center of the non-polar face of said amphipathic helix; that protects a phospholipid against oxidation by an oxidizing agent; and that is not the D-18A peptide. In certain embodiments, the peptide comprises the amino acid sequence of a peptide listed in Table 2 or Table 10. In certain embodiments, the peptide is a protected tetramer as show in Table 2 or Table 10.

In certain embodiments, the peptides of this invention protect a phospholipid (e.g., 1-palmitoyl-2-arachidonoyl-sn-glycero-3-phosphorylcholine (PAPC), 1-stearoyl-2-arachidonoyl-sn-glycero-3-phosphorylcholine (SAPC)), 1-stearoyl-2-arachidonyl-sn-glycero-3-phosphorylethanolamine (SAPE)) against oxidation by an oxidizing agent (e.g. 13(S)-HPODE, 15(S)-HPETE, HPODE, HPETE, HODE, HETE, etc.).

Any of the peptides described herein can bear one or more hydrophobic protecting groups on the amino terminal amino acid (e.g., $X^1$) and/or the carboxyl terminal amino acid (e.g. $X^4$, $X^5$, etc.). The protecting group(s) can be attached to the amino or carboxyl terminus and/or to a side chain (R group) of the amino acid. The protecting group(s) can be directly coupled (e.g. through a covalent bond) or indirectly coupled (e.g. through a linker). Preferred hydrophobic protecting groups include, but are not limited to t-butoxycarbonyl (Boc), Fmoc, nicotinyl, OtBu, a benzoyl group, an acetyl (Ac), a carbobenzoxy, methyl, ethyl, a propyl, a butyl, a pentyl a hexyl ester, an N-methyl anthranilyl, and a 3 to 20 carbon alkyl, amide, a 3 to 20 carbon alkyl group, 9-fluoreneacetyl group, 1-fluorenecarboxylic group, 9-fluorenecarboxylic group, 9-fluorenone-1-carboxylic group, benzyloxycarbonyl (is also called carbobenzoxy mentioned above), Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO),t-butoxymethyl (Bum), t-butoxy (tBuO), t-Butyl (tBu), trifluoroacetyl (TFA), 4[N-{1-(4,4-dimethyl-2,6-dioxocyclohexylidene)-3-methyldibutyl)-amino}benzyl ester (ODmab), α-allyl ester (OAll), 2-phenylisopropyl ester (2-PhiPr), 1-[4,4-dimethyl-2,6-dioxycyclohex-1-yl-idene) ethyl (Dde), and the like. In certain embodiments, the said hydrophobic protecting group is selected from the group consisting of Boc, Fmoc, nicotinyl, and OtBu. In certain embodiments, the N-terminus of the peptide is blocked with a protecting group selected from the group consisting of Boc-, Fmoc-, and Nicotinyl- and/or the C-terminus of the peptide is blocked with a protecting group selected from the group consisting of tBu, and OtBu.

The peptides can also, optionally, include at least one D amino acid. In certain embodiments, the peptides include a plurality of D- amino acids or can even compirse all D-amino acids. In certain embodiments, the peptide comprise alternating D- and L-amino aicds. The peptides can also be all L-form amino acids. The peptides can be isolated (e.g. substanitaly pure), dry or in solution, and/or combined with a pharmacologically acceptable excipient. In certain embodiments, the peptide is mixed with a pharmacologically acceptable excipient suitable for oral administration to a mammal (e.g. a human or a non-human mammal). The peptide can be provided as a unit formulation in a pharmaceutically acceptable excipient and/or as a time release formulation.

The peptides can also be coupled to one or more biotins (e.g. directly, through a linker, and/or through the amino acid side chain). In certain embodiments, the biotin is coupled to a lysine (Lys).

This invention also provides a pharmaceutical formulation comprising one or more of the peptides described herein and a pharmaceutically acceptable excipient. Typically the peptide(s) are present in an effective dose. The peptide(s) can also be provided as a time release formulation and/or as a unit dosage formulation. In certain embodiments, the formulation is formulated for oral administration. In certain embodiments, the formulation is formulated for administration by a route selected from the group consisting of oral administration, nasal administration, rectal administration, intraperitoneal injection, intravascular injection, subcutaneous injection, transcutaneous administration, inhalation administration, and intramuscular injection.

Also provided is a kit comprising a container containing one or more of the peptides described herein and instructional materials teaching the use of the peptide(s) in the treatment of a pathology characterized by inflammation (e.g. atherosclerosis atherosclerosis, rheumatoid arthritis, lupus erythematous, polyarteritis nodosa, osteoporosis, Altzheimer's disease, a viral illnesses, etc.).

This invention also provides a method of mitigating (e.g. reducing or eliminating) one or more symptoms of atherosclerosis in a mammal (human or non-human mammal). The method typically involves administering to the mammal an effective amount of one or more of the peptides described herein. The peptide can be administered in a in a pharmaceutically acceptable excipient (e.g. for oral administration) and can, optionally be administered in conjunction (e.g. before, after, or simultaneously) with a lipid. The administering can comprise administering said peptide by a route selected from the group consisting of oral administration, nasal administration, rectal administration, intraperitoneal injection, intravascular injection, subcutaneous injection, transcutaneous administration, and intramuscular injection. In certain embodiments, the mammal is a mammal diagnosed as having one or more symptoms of atherosclerosis. In certain embodiments, the mammal is a mammal diagnosed as at risk for stroke or atherosclerosis.

In another embodiment, this invention provides method of mitigating one or more symptoms of an inflammatory pathology (e.g., atherosclerosis, rheumatoid arthritis, lupus erythematous, polyarteritis nodosa, osteoporosis, Altzheimer's disease and a viral illnesses). The method typically involves administering to the mammal an effective amount of one or more of the peptides described herein. The peptide can be administered in a in a pharmaceutically acceptable excipient (e.g. for oral administration) and can, optionally be administered in conjunction (e.g. before, after, or simultaneously) with a lipid. The administering can comprise administering said peptide by a route selected from the group consisting of oral administration, nasal administration, rectal administration, intraperitoneal injection, intravascular injection, subcutaneous injection, transcutaneous administration, and intramuscular injection. In certain embodiments, the mammal is a mammal diagnosed as having one or more symptoms of of the inflammatory pathology. In certain embodiments, the mammal is a mammal diagnosed as at risk for the inflammatory pathology.

The peptides of this invention also act synergistically with statins and/or with a selective cholesterol uptake inhibitor (e.g. Ezetimibe). The method typically involves coadministering with the statin and/or cholesterol uptake inhibitor an effective amount of one or more of the peptides described herein. In certain embodiments, the statin is selected from the group consisting of cerivastatin, atorvastatin, simvastatin, pravastatin, fluvastatin, lovastatin. rosuvastatin, and pitavastatin. The peptide can be administered before, after, or simultaneously with the statin and/or the cholesterol uptake inhibitor. The peptide and/or said statin and/or cholesterol uptake inhibitor can be administered as a unit dosage formulation. In certain embodiments, the administering comprises administering said peptide and/or said statin by a route selected from the group consisting of oral administration, nasal administration, rectal administration, intraperitoneal injection, intravascular injection, subcutaneous injection, transcutaneous administration, and intramuscular injection. The mammal includes, but is not limited to a mammal diagnosed as having one or more symptoms of atherosclerosis or diagnosed as at risk for stroke or atherosclerosis.

This invention also provides a method of mitigating one or more symptoms associated with atherosclerosis in a mammal. The method typically involves administering a statin and/or a selective cholesterol uptake inhibitor; and an effective amount of one or more peptides described herein, where the the effective amount of the statin and/or cholesterol uptake inhibitor is lower than the effective amount of a statin or a cholesterol uptake inhibitor administered without the peptide(s). In certain embodiments, the effective amount of the peptide(s) is lower than the effective amount of the peptide administered without the statin and/or cholesterol uptake inhibitor. In certain embodiments, the statin is selected from the group consisting of cerivastatin, atorvastatin, simvastatin, pravastatin, fluvastatin, lovastatin. rosuvastatin, and pitavastatin. The peptide can be administered before, after, or simultaneously with the statin and/or the cholesterol uptake inhibitor. The peptide and/or said statin and/or cholesterol uptake inhibitor can be administered as a unit dosage formulation. In certain embodiments, the administering comprises administering said peptide and/or said statin by a route selected from the group consisting of oral administration, nasal administration, rectal administration, intraperitoneal injection, intravascular injection, subcutaneous injection, transcutaneous administration, and intramuscular injection. The mammal includes, but is not limited to a mammal diagnosed as having one or more symptoms of atherosclerosis or diagnosed as at risk for stroke or atherosclerosis. The mammal includes, but is not limited to a mammal diagnosed as having one or more symptoms of atherosclerosis or diagnosed as at risk for stroke or atherosclerosis.

In still another embodiment, this invention provides a method of reducing or inhibiting one or more symptoms of osteoporosis in a mammal. The method typically involves administering to the mammal one or more peptide(s) described herein, where peptide is administered in a concentration sufficient to reduce or eliminate one or more symptoms of osteoporosis. In certain embodiments, the peptide(s) are administered in a concentration sufficient to reduce or eliminate decalcification of a bone. In certain embodiments, the peptide(s) are administered in a concentration sufficient to induce recalcification of a bone. The peptide(s) can be combined with a pharmacologically acceptable excipient (e.g., an excipient suitable for oral administration to a mammal).

In certain embodiments, the methods and/or peptides of this invention exclude any one or more peptides disclosed in WO 97/36927, and/or U.S. Pat. No. 6,037,323, and/or U.S. Pat. No. 4,643,988 and/or in Garber et al. (1992) *Arteriosclerosis and Thrombosis,* 12: 886–894. In certain embodiments this invention excludes any one or more peptides disclosed in U.S. Pat. No. 4,643,988 and/or in Garber et al (1992) that were synthesized with all enantiomeric amino acids being L amino acids or synthesized with D amino acids where the peptides are blocking groups. In certain embodiments, this invention excludes peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ (SEQ ID NO:(SEQ ID NO: 1) wherein $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, B8 and $B_9$ are independently tryptophan, phenylalanine, alanine, leucine, tyrosine, isoleucine, valine or α-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not tryptophan.

In certain embodiments, this invention excludes any one or more peptides in WO 97/36927 and/or D variants thereof. Particular embodiments exclude one or more of the following: apoprotein A, apoprotein A-1, apoprotein A-2, apoprotein A4, apoprotein B, apoprotein B-48, apoprotein B-100, apoprotein C, apoprotein C-1, apoprotein C-2, apoprotein C-3, apoprotein D, apoprotein E as described in WO 97/36927.

In certain embodiments, Also excluded are any one or more peptides disclosed in U.S. Pat. No. 6,037,323 and/or D variants thereof. Particular embodiments exclude apo A-I agonist compounds comprising (i) an 18 to 22-residue peptide or peptide analogue that forms an amphipathic .alpha.-helix in the presence of lipids and that comprises the formula: $Z_1$-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$Z_2$, (SEQ ID NO:2), where $X_1$ is Pro (P), Ala (A), Gly (G), Asn (N), Gln (Q) or D-Pro (p); $X_2$ is an aliphatic amino acid; $X_3$ is Leu (L); $X^4$ is an acidic amino acid; $X_5$ is Leu (L) or Phe (F); $X_6$ is Leu (L) or Phe (F); $X_7$ is a basic amino acid; $X_8$ is an acidic amino acid; $X_9$ is Leu (L) or Trp (W); $X_{10}$ is Leu (L) or Trp (W); $X_{11}$ is an acidic amino acid or Asn (N); $X_{12}$ is an acidic amino acid; $X_{13}$ is Leu (L), Trp (W) or Phe (F); $X_{14}$ is a basic amino acid or Leu (L); $X_{15}$ is Gln (Q) or Asn (N); $X_{16}$ is a basic amino acid; $X_{17}$ is Leu (L); $X_{18}$ is a basic amino acid; $Z_1$ is $H_2N$— or RC(O)NH—; $Z_2$ is —C(O)NRR, —C(O)OR or —C(O)OH or a salt thereof; each R is independently —H, ($C_1$–$C_6$) alkyl, ($C_1$–$C_6$) alkenyl, ($C_1$–$C_6$) alkynyl, ($C_5$–$C_{20}$) aryl, ($C_6$–$C_{26}$) alkaryl, 5–20 membered heteroaryl or 6–26 membered alkheteroaryl or a 1 to 4-residue peptide or peptide analogue in which one or more bonds between residues 1–7 are independently a substituted amide, an isostere of an amide or an amide mimetic; and each "-" between residues $X_1$ through $X_{18}$ independently designates an amide linkage, a substituted amide linkage, an isostere of an amide or an amide mimetic; or (ii) an altered form of formula (I) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ or $X_{18}$ is conservatively substituted with another residue, and/or D variants thereof.

In certain embodiments, this invention excludes peptides having the sequence Lys-Arg-Asp-Ser (SEQ ID NO:238) and in certain embodiments, this invention excludes peptides having the sequence Lys-Arg-Asp-Ser (SEQ ID NO:238) in which Lys-Arg-Asp and Ser are all L amino acids.

DEFINITIONS

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., "Segrest et al. (1990) *Proteins: Structure, Function, and Genetics* 8: 103–117).

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like. "Ameliorating one or more symptoms of atherosclerosis" can also refer to improving blood flow to vascular beds affected by atherosclerosis.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propionyl, formyl and others. Preferred carboxyl terminal protecting groups include, but are not limited to groups that form amides or esters. The term "side chain protection groups" refers to protecting groups that protect/block a side-chain (i.e. an R group) of an amino acid. Side-chain protecting groups include, but are not limited to amino protecting groups, carboxyl protecting groups and hydroxyl protecting groups such as aryl ethers and guanidine protecting groups such as nitro, tosyl etc.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)-HPODE, 15-(S)-HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phsophocholine; ChC18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PON: paraoxonase; BL/6: C57BL/6J; C3H:C3H/HeJ.

The term "conservative substitution" is used in reference to proteins or peptides to reflect amino acid substitutions that do not substantially alter the activity (specificity (e.g. for lipoproteins))or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Nati. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA* ,90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "D-18A peptide" refers to a peptide having the sequence: D-W-L-K-A-F-Y-D-K-V-A-E-K-L-K-E-A-F (SEQ ID NO:3) where all of the enantiomeric amino acids are D form amino acids.

The term "coadministering" or "concurrent administration", when used, for example with respect to a peptide of this invention and another active agent (e.g. a statin), refers to administration of the peptide and the active agent such that both can simultaneously achieve a physiological effect. The two agents, however, need not be administered together. In certain embodiments, administration of one agent can precede administration of the other, however, such coadministering typically results in both agents being simultaneously present in the body (e.g. in the plasma) at a significant fraction (e.g. 20% or greater, preferably 30% or 40% or greater, more preferably 50% or 60% or greater, most preferably 70% or 80% or 90% or greater) of their maximum serum concentration for any given dose.

The term "detoxify" when used with respect to lipids, LDL, or HDL refers the removal of some or all oxidizing lipids and/or oxidized lipids. Thus, for example, the uptake of all or some HPODE and/or HPETE (both hydroperoxides on fatty acids) will prevent or reduce entrance of these peroxides into LDLs and thus prevent or reduce LDL oxidation.

The term "pre-beta high density lipoprotein-like particles" typically refers to cholesterol containing particles that also contain apoA-I and which are smaller and relatively lipid-poor compared to the lipid: protein ratio in the majority of HDL particles. When plasma is separated by FPLC, these "pre-beta high density lipoprotein-like particles" are found in the FPLC fractions containing particles smaller than those in the main HDL peak and are located to the right of HDL in an FPLC chromatogram as shown in related application U.S. Ser. No. 10/423,830.

The phrase "reverse lipid transport and detoxification" refers to the removal of lipids including cholesterol, other sterols including oxidized sterols, phospholipids, oxidizing agents, and oxidized phospholipids from tissues such as arteries and transport out of these peripheral tissues to organs where they can be detoxified and excreted such as excretion by the liver into bile and excretion by the kidneys into urine. Detoxification also refers to preventing the formation and/or destroying oxidized phospholipids as explained herein.

The term "biological sample" as used herein refers to any sample obtained from a living organism or from an organism that has died. Examples of biological samples include body fluids, tissue specimens, cells and cell lines taken from an organism (e.g. a human or non-human mammal).

The term "amide" when referring to a hydrophobic protecting group or a hydrophobic blocking group includes a simple amide to methylamide or ethylamide. The term also includes alkyl amides such as CO—NH—R where R is methyl, ethyl, etc. (e.g. up to 7, preferably 9, more preferably 11 or 13 carbons).

The term "D-peptide" refers to a peptide in which one or more of the enantiiomeric amino acids comprising the peptide are D form amino acids. In certain embodiments, a plurality of the enantiomeric amino acids are D form amino acids. In certain embodiments, at least half of the enantiomeric amino acids are D form amino acids. In certain embodiments, the peptide comprises alternating D- and L-form amino acids. In certain embodiments, all of the enantiomeric amino acids are D form amino acids.

The term "L-peptide" refers to a peptide in which all of the amino acids (enantiomeric amino acids) are L-form amino acids.

Figure 1:
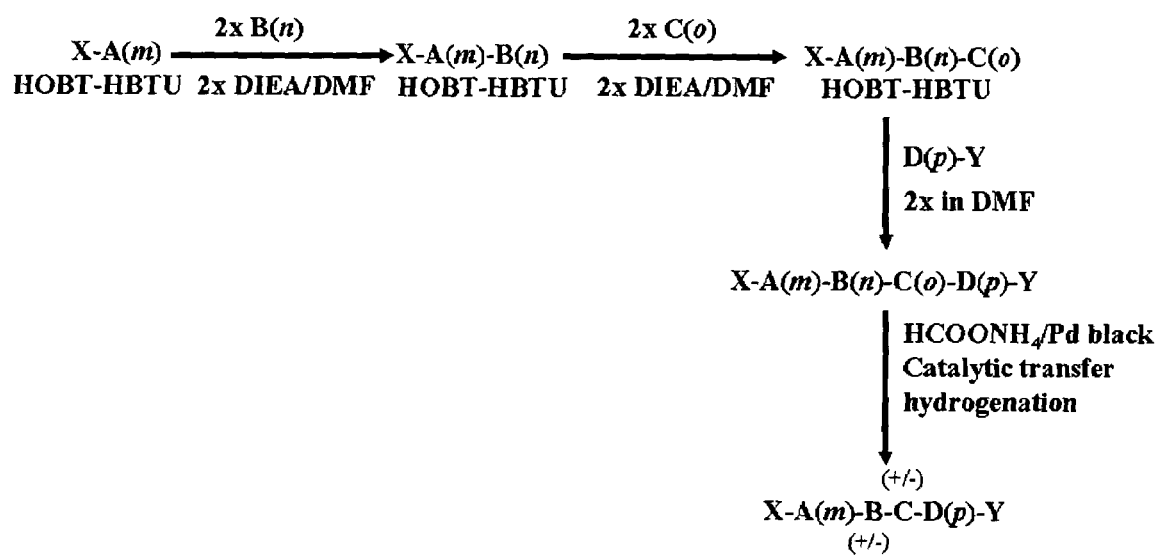
FIG. 1 illustrates a synthesis scheme for the solution phase synthesis of peptides according to this invention.

A peptide that "converts pro-inflammatory HDL to anti-inflammatory HDL or makes anti-inflammatory HDL more anti-inflammatory" refers to a peptide that when administered to a mammal (e.g. a human, a rat, a mouse, etc.), or that when used in an appropriate ex vivo assay (e.g. as described herein), converts HDL to an HDL that reduces or blocks lipid oxidation by an oxidizing agent (e.g. as described in U.S. Ser. No. 6,596,544), and/or that has increased paraoxonase activity, and/or that decreases LDL-induced monocyte chemotactic activity generated by artery wall cells as compared to HDL in a control assay (e.g. HDL from a control animal or assay administered a lower dose of the peptide or a negative control animal or assay lacking the peptide). The alteration of HDL (conversion from non-protective to protective or increase in protective activity) is preferably a detectable change. In preferred embodiments, the change is a statistically significant change, e.g. as determined using any statistical test suited for the data set provided (e.g. t-test, analysis of variance (ANOVA), semiparametric techniques, non-parametric techniques (e.g. Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level. In certain embodiments, the change is at least a 10% change, preferably at least a 20% change, more preferably at least a 50% change and most preferably at least a 90% change.

DETAILED DESCRIPTION

This invention pertains to the discovery that synthetic peptides designed to mimic the class A amphipathic helical motif (Segrest et al. (1990) Proteins: Structure, Function, and Genetics 8: 103–117) are able to associate with phospholipids and exhibit many biological properties similar to human apo-A-I. In particular, it was a discovery of this invention that when such peptides are formulated using D amino acids, the peptides show dramatically elevated serum half-lives and, particularly when the amino and/or carboxy termini are blocked, can even be orally administered.

It was also a surprising discovery that these peptides can stimulate the formation and cycling of pre-beta high density lipoprotein-like particles. In addition, the peptides are capable of enhancing/synergizing the effect of statins allowing statins to be administered as significantly lower dosages or to be significantly more anti-inflammatory at any given dose. It was also discovered that the peptides described herein can inhibit and/or prevent and/or treat one or more symptoms of osteoporosis. The peptides can also increase pre-beta HDL; and/or increase HDL paroxynase activity.

Moreover, it was a surprising discovery of this invention that such D-form peptides retain the biological activity of the corresponding L-form peptide. In vivo animal studies using such D-form peptides showed effective oral delivery, elevated serum half-life, and the ability to mitigate or prevent/inhibit one or more symptoms of atherosclerosis.

It was also a surprising discovery that certain small peptides consisting of a minimum of three amino acids preferentially (but not necessarily) with one or more of the amino acids being the D-sterioisomer of the amino acid, and possessing hydrophobic domains to permit lipid protein interactions, and hydrophilic domains to permit a degree of water solubility also possess significant anti-inflammatory properties. Without being bound to a particular theory, it is believed that the peptides bind the "seeding molecules" required for the formation of pro-inflammatory oxidized phospholipids such as Ox-PAPC, POVPC, PGPC, and PEIPC. Since many inflammatory conditions are mediated at least in part by oxidized lipids, we believe that the peptides of this invention are effective in ameliorating conditions that are known or suspected to be due to the formation of biologically active oxidized lipids. These include, but are not limited to atherosclerosis, rheumatoid arthritis, lupus erythematous, polyarteritis nodosa, and osteoporosis. The "small peptides" typically range in length from 3 amino acids to about 15 amino acids, more preferably from about 4 amino acids to about 10 or 11 amino acids, and most preferably from about 4 to about 8 or 10 amino acids. The peptides are typically characterized by having hydrophobic terminal amino acids or terminal amino acids rendered hydrophobic by the attachment of one or more hydrophobic "protecting" groups. The internal structures of the peptides are described in more detail herein.

I. Stimulating the Formation and Cycling of Pre-beta High Density Lipoprotein-like Particles.

Reverse cholesterol transport is considered to be important in preventing the build up of lipids that predisposes to atherosclerosis (Shah et al. (2001) Circulation, 103: 3047–3050.) Many have believed the lipid of consequence is cholesterol. Our laboratory has shown that the key lipids are oxidized phospholipids that initiate the inflammatory response in atherosclerosis (Navab et al. (2001) Arterioscler Thromb Vasc Biol., 21(4): 481–488; Van Lenten et al. (001) Trends Cardiovasc Med, 11: 155–161; Navab M et al. (2001) Circulation, 104: 2386–2387).

This inflammatory response is also likely responsible for plaque erosion or rupture that leads to heart attack and stroke. HDL-cholesterol levels are inversely correlated with risk for heart attack and stroke (Downs et al. (1998) JAMA 279: 1615–1622; Gordon et al. (1977) Am J Med., 62: 707–714; Castelli et al. (1986) JAMA, 256: 2835–2838).

Pre-beta HDL is generally considered to be the most active HDL fraction in promoting reverse cholesterol transport (e.g., picking up cholesterol from peripheral tissues such as arteries and carrying it to the liver for excretion into the bile; see, Fielding and Fielding (2001) Biochim Biophys Acta, 1533(3): 175–189). However, levels of pre-beta HDL can be increased because of a failure of the pre-beta HDL to be cycled into mature alpha-migrating HDL e.g. LCAT deficiency or inhibition (O'Connor et al. (1998) J Lipid Res, 39: 670–678). High levels of pre-beta HDL have been reported in coronary artery disease patients (Miida et al. (1996) Clin Chem., 42: 1992–1995).

Moreover, men have been found to have higher levels of pre-beta HDL than women but the risk of men for coronary heart disease is greater than for women (O'Connor et al. (1998) J Lipid Res., 39: 670–678). Thus, static measurements of pre-beta HDL levels themselves are not necessarily predictive of risk for coronary artery disease. The cycling, however, of cholesterol through pre-beta HDL into mature HDL is universally considered to be protective against atherosclerosis (Fielding and Fielding (2001) Biochim Biophys Acta, 1533(3): 175–189). Moreover, we have demonstrated that the removal of oxidized lipids from artery wall cells through this pathway protects against LDL oxidation.

Despite relatively low absorption rates when orally administered, the peptides of this invention (e.g. D-4F) were highly active.

In studies of Apo-E null mice orally administered D-4F, we determined that 20 min after absorption from the intestine, D-4F forms small pre-beta HDL-like particles that contain relatively high amounts of apoA-I and paraoxonase. Indeed, estimating the amount of apoA-I in these pre-beta HDL-like particles from Western blots and comparing the amount of apoA-I to the amount of D-4F in these particles (determined by radioactivity or LC-MRM) suggests that as D-4F is absorbed from the intestine, it acts as a catalyst causing the formation of these pre-beta HDL-like particles. This small amount of intestinally derived D-4F appears to recruit amounts of apoA-I, paraoxonase, and cholesterol into these particles that are orders of magnitude more than the amount of D-4F.

Thus, following absorption, D-4F, and other peptides of this invention, rapidly recruit relatively large amounts of apoA-I and paraoxonase to form pre-beta HDL-like particles which are very likely the most potent particles for both promoting reverse cholesterol transport and for destroying biologically active oxidized lipids. We believe that the formation of these particles and their subsequent rapid incorporation into mature HDL likely explains the dramatic reduction in atherosclerosis that we observed in LDL receptor null mice on a Western diet and in apoE-null mice on a chow diet independent of changes in plasma cholesterol or HDL-cholesterol.

Thus, in one embodiment, this invention provides methods of stimulating the formation and cycling of pre-beta high density lipoprotein-like particles by administration of one or more peptides as described herein. The peptides can thereby promote lipid transport and detoxification.

II. Synergizing the Activity of Statins.

It was also discovered that, adding a low dosage of D-4F (1 µg/ml) to the drinking water of apoE null mice for 24 hours did not significantly improve HDL function (see, e.g., related application U.S. Ser. No. 10/423,830). In addition, adding 0.05 mg/ml of atorvastatin or pravastatin alone to the drinking water of the apoE null mice for 24 hours did not improve HDL function. However, when D-4F 1 µg/ml was added to the drinking water together with 0.05 mg/ml of atorvastatin or pravastatin there was a significant improvement in HDL function). Indeed the pro-inflammatory apoE null HDL became as anti-inflammatory as 350 µg/ml of normal human HDL (h, HDL see, e.g., related application U.S. Ser. No. 10/423,830).

Thus, doses of D-4F alone, or statins alone, which by themselves had no effect on HDL function when given together acted synergistically. When D-4F and a statin were given together to apo E null mice, their pro-inflammatory HDL at 50 µg/ml of HDL-cholesterol became as effective as normal human HDL at 350 µg/ml of HDL-cholesterol in preventing the inflammatory response induced by the action of HPODE oxidizing PAPC in cocultures of human artery wall cells.

Thus, in certain embodiments this invention provides methods for enhancing the activity of statins. The methods generally involve administering one or more peptides as described herein concurrently with one or more statins. The D-4F or other similar peptides as described herein achieve synergistic action between the statin and the orally peptide(s) to ameliorate atherosclerosis. In this context statins can be administered at significantly lower dosages thereby avoiding various harmful side effects (e.g. muscle wasting) associated with high dosage statin use and/or the anti-inflammatory properties of statins at any given dose are significantly enhanced.

III. Inhibiting/treating Osteoporosis.

Vascular calcification and osteoporosis often co-exist in the same subjects (Ouchi et al. (1993) Ann NY Acad Sci., 676: 297–307; Boukhris and Becker ('1972) JAMA, 219: 1307–1311; Banks et al. (1994) Eur J Clin Invest., 24: 813–817; Laroche et al. (1994) Clin Rheumatol., 24: 611–614; Broulik and Kapitola (1993) Endocr Regul., 27: 57–60; Frye et al. (1992) Bone Mine., 19: 185–194; Barengolts et al. (1998) Calcif Tissue Int., 62: 209–213; Burnett and Vasikaran (2002) Ann Clin Biochem., 39: 203–210. Parhami et al. (Parhami et al. (1997) *Arterioscl Thromb Vasc Biol.*, 17: 680–687) demonstrated that mildly oxidized LDL (MM-LDL) and the biologically active lipids in MM-LDL [i.e. oxidized 1-palmitoyl-2-arachidonoyl-sn-glycero-3-phosphorylcholine) (Ox-PAPC)], as well as the isoprostane, 8-iso prostaglandin $E_2$, but not the unoxidized phospholipid (PAPC) or isoprostane 8-iso progstaglandin $F_{2\alpha}$ induced alkaline phosphatase activity and osteoblastic differentiation of calcifying vascular cells (CVCs) in vitro, but inhibited the differentiation of MC3T3-E1 bone cells.

The osteon resembles the artery wall in that the osteon is centered on an endothelial cell-lined lumen surrounded by a subendothelial space containing matrix and fibroblast-like cells, which is in turn surrounded by preosteoblasts and osteoblasts occupying a position analogous to smooth muscle cells in the artery wall (Id.). Trabecular bone osteoblasts also interface with bone marrow subendothelial spaces (Id.). Parhami et al. postulated that lipoproteins could cross the endothelium of bone arteries and be deposited in the subendothelial space where they could undergo oxidation as in coronary arteries (Id.). Based on their in vitro data they predicted that LDL oxidation in the subendothelial space of bone arteries and in bone marrow would lead to reduced osteoblastic differentiation and mineralization which would contribute to osteoporosis (Id.). Their hypothesis further predicted that LDL levels would be positively correlated with osteoporosis as they are with coronary calcification (Pohle et al. (2001) *Circulation*, 104: 1927–1932) but HDL levels would be negatively correlated with osteoporosis (Parhami et al. (1997) *Arterioscl Thromb Vasc Biol.*, 17: 680–687).

In vitro, the osteoblastic differentiation of the marrow stromal cell line M2-10B4 was inhibited by MM-LDL but not native LDL (Parhami et al. (1999) *J Bone Miner Res.*, 14: 2067–2078). When marrow stromal cells from atherosclerosis susceptible C57B/L6 (BL6) mice fed a low fat chow diet were cultured there was robust osteogenic differentiation (Id.). In contrast, when the marrow stromal cells taken from the mice after a high fat, atherogenic diet were cultured they did not undergo osteogenic differentiation (Id.). This observation is particularly important since it provides a possible explanation for the decreased osteogenic potential of marrow stromal cells in the development of osteoporosis (Nuttall and Gimble (2000) *Bone*, 27: 177–184). In vivo the decrease in osteogenic potential is accompanied by an increase in adipogenesis in osteoporotic bone (Id.).

It was found that adding D-4F to the drinking water of apoE null mice for 6 weeks dramatically increased trabecular bone mineral density and it is believed that the other peptides of this invention will act similarly.

Our data indicate that osteoporosis can be regarded as an "atherosclerosis of bone". It appears to be a result of the action of oxidized lipids. HDL destroys these oxidized lipids and promotes osteoblastic differentiation. Our datat indicate that administering peptide(s) of this invention to a mammal (e.g. in the drinking water of apoE null mice) dramatically increases trabecular bone in just a matter of weeks.

This indicates that the peptides described herein are useful for mitigation one or more symptoms of atherosclerosis (e.g. for inhibiting decalcification) or for inducing recalcification of osteoporotic bone. The peptides are also useful as prophylactics to prevent the onset of symptom(s) of osteoporosis in a mammal (e.g. a patient at risk for osteoporosis).

IV. Mitigation of a Symptom of Atherosclerosis.

We discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37 pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

Figure 2:
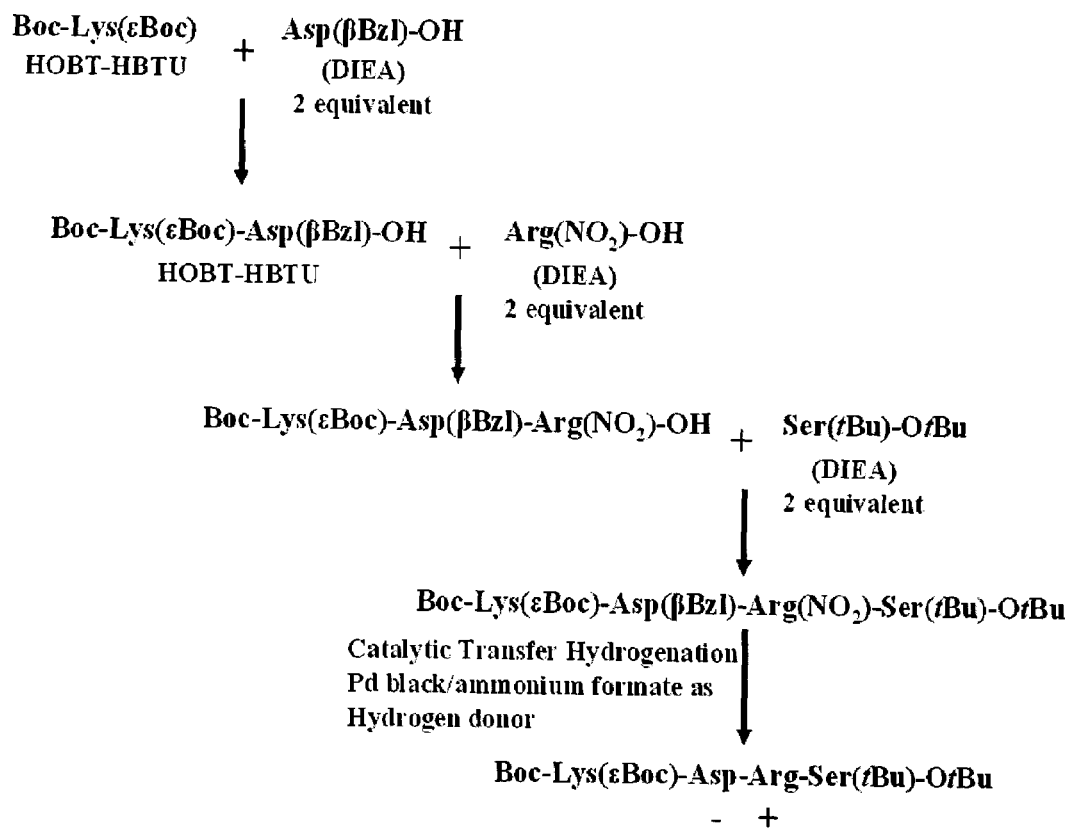
FIG. 2 illustrates the process for synthesizing a tetrapeptide using the process outlined in FIG. 1.

The protective function of the D peptides of this invention is illustrated in the parent applications (Ser. No. 09/645,454, filed Aug. 24, 2000, now U.S. Pat. No. 6,664,230, Ser. No. 09/896,841, filed Jun. 29, 2001, now U.S. Pat. No. 6,933,270, and WO 02/15923 (PCT/US01/26497), filed Jun. 29, 2001, see, e.g., FIGS. 1–5 in WO 02/15923). FIG. 1, panels A, B, C, and D in WO 02/15923 show the association of $^{14}$C-D-5F with blood components in an ApoE null mouse. It is also demonstrated that HDL from mice that were fed an atherogenic diet and injected with PBS failed to inhibit the oxidation of human LDL and failed to inhibit LDL-induced monocyte chemotactic activity in human artery wall coculures. In contrast, HDL from mice fed an atherogenic diet and injected daily with peptides described herein was as effective in inhibiting human LDL oxidation and preventing LDL-induced monocyte chemotactic activity in the cocultures as was normal human HDL (FIGS. 2A and 2B in WO 02/15923). In addition, LDL taken from mice fed the atherogenic diet and injected daily with PBS was more readily oxidized and more readily induced monocyte chemotactic activity than LDL taken from mice fed the same diet but injected with 20 µg daily of peptide 5F. The D peptide did not appear to be immunogenic (FIG. 4 in WO 02/15923).

Figure 5:
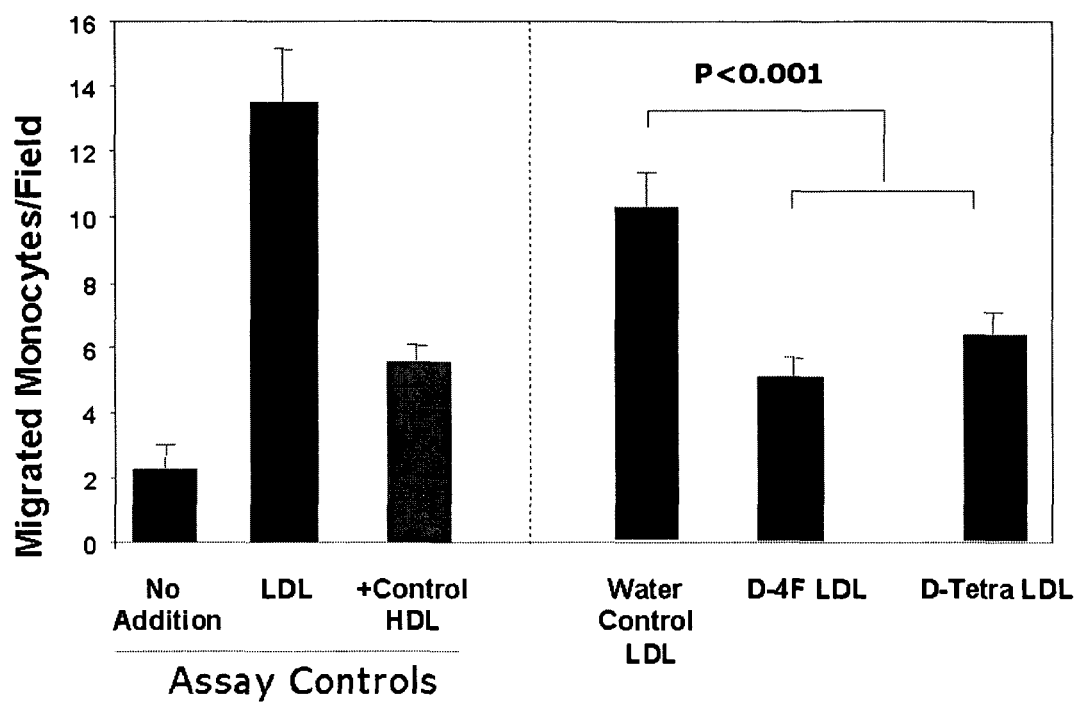
FIG. 5 shows that apoE null mice receiving D-tetrapeptide or D-4F in their drinking water have LDL that induces less monocyte chemotactic activity. The LDL from the FPLC fractions of the mice described in FIG. 4 was added to the cocultures at 100 μg/ml. After 8 hours the supernatants were assayed for monocyte chemotactic activity.

The in vitro responses of human artery wall cells to HDL and LDL from mice fed the atherogenic diet and injected with a peptide according to this invention are consistent with the protective action shown by such peptides in vivo. Despite, similar levels of total cholesterol, LDL-cholesterol, IDL+VLDL-cholesterol, and lower HDL-cholesterol as a percent of total cholesterol, the animals fed the atherogenic diet and injected with the peptide had significantly lower lesion scores (FIG. 5 in WO 02/15923). The peptides of this invention thus prevented progression of atherosclerotic lesions in mice fed an atherogenic diet.

Thus, in one embodiment, this invention provides methods for ameliorating and/or preventing one or more symptoms of atherosclerosis.

VI. Mitigation of a Symptom of Atheroscloerosis Associated with an Acute Inflammatory Response.

The peptides of this invention are also useful in a number of contexts. For example, we have observed that cardiovascular complications (e.g. atherosclerosis, stroke, etc.) frequently accompany or follow the onset of an acute phase inflammatory response. Such an acute phase inflammatory response is often associated with a recurrent inflammatory disease (e.g., leprosy, tuberculosis, systemic lupus erythematosus, and rheumatoid arthritis), a viral infection (e.g. influenza), a bacterial infection, a fungal infection, an organ transplant, a wound or other trauma, an implanted prosthesis, a biofilm, and the like.

It was a surprising discovery of this invention that administration of one or more of the peptides described herein, can reduce or prevent the formation of oxidized phospholipids during or following an acute phase response and thereby mitigate or eliminate cardiovascular complications associated with such a condition.

Thus, for example, we have demonstrated that a consequence of influenza infection is the diminution in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and was no longer able to prevent the LDL-induced production of monocyte chemotactic activity by endothelial cells.

We observed that in a subject injected with very low dosages of the polypeptides of this invention (e.g. 20 micrograms for mice) daily after infection with the influenza A virus paraoxonase levels did not fall and the biologically active oxidized phospholipids were not generated beyond background. This indicates that D-4F (and/or other peptides of this invention) can be administered (e.g. orally or by injection) to patients with known coronary artery disease during influenza infection or other events that can generate an acute phase inflammatory response (e.g. due to viral infection, bacterial infection, trauma, transplant, various autoimmune conditions, etc.) and thus we can prevent by this short term treatment the increased incidence of heart attack and stroke associated with pathologies that generate such inflammatory states.

Thus, in certain embodiments, this invention contemplates administering one or more of the peptides of this invention to a subject at risk for, or incurring, an acute inflammatory response and/or at risk for or incurring a symptom of atherosclerosis.

Thus, for example, a person having or at risk for coronary disease may prophylactically be administered a polypeptide of this invention during flu season. A person (or animal) subject to a recurrent inflammatory condition, e.g. rheumatoid arthritis, various autoimmune diseases, etc., can be treated with a polypeptide of this invention to mitigate or prevent the development of atherosclerosis or stroke. A person (or animal) subject to trauma, e.g. acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g. AGP measured by Cardiotech Services, Louisville, Ky.).

VII. Mitigation of a Symptom or Condition Associated with Coronary Calcification and Osteoporosis.

We have also identified oxidized lipids as a cause of coronary calcification and osteoporosis. Moreover, without being bound to a particularly theory, we believe the same mechanisms are involved in the pathogenesis of calcific aortic stenosis.

Thus, in certain embodiments, this invention contemplates the use of the peptides described herein to inhibit or prevent a symptom of a disease such as polymyalgia rheumatica, polyarteritis nodosa, scleroderma, lupus erythematosus, idiopathic pulmonary fibrosis, chronic obstructive pulmonary disease, Alzheimers Disease, AIDS, coronary calcification, calcific aortic stenosis, osteoporosis, and the like.

V. Peptide Administration.

The methods of this invention typically involve administering to an organism, preferably a mammal, more preferably a human one or more of the peptides of this invention (or mimetics of such peptides). The peptide(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g. as a syrup, capsule, or tablet).

The methods can involve the administration of a single peptide of this invention or the administration of two or more different peptides. The peptides can be provided as monomers or in dimeric, oligomeric or polymeric forms. In certain embodiments, the multimeric forms may comprise associated monomers (e.g. ionically or hydrophobically linked) while certain other multimeric forms comprise covalently linked monomers (directly linked or through a linker).

While the invention is described with respect to use in humans, it is also suitable for animal, e.g. veterinary use. Thus preferred organisms include, but are not limited to humans, non-human primates, canines, equines, felines, porcines, ungulates, largomorphs, and the like.

The methods of this invention are not limited to humans or non-human animals showing one or more symptom(s) of atherosclerosis (e.g. hypertension, plaque formation and rupture, reduction in clinical events such as heart attack, angina, or stroke, high levels of plasma cholesterol, high levels of low density lipoprotein, high levels of very low density lipoprotein, or inflammatory proteins such as CRP, etc.), but are useful in a prophylactic context. Thus, the peptides of this invention (or mimetics thereof) may be administered to organisms to prevent the onset/development of one or more symptoms of atherosclerosis. Particularly preferred subjects in this context are subjects showing one or more risk factors for atherosclerosis (e.g. family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

The peptides of this invention can also be administered to stimulate the formation and cycling of pre-beta high density lipoprotein-like particles and/or to promote reverse lipid transport and detoxification.

The peptides are also useful for administration with statins where they enhance (e.g., synergize) the activity of the statin and permit the statin(s) to be administered at lower dosages and/or the anti-inflammatory properties of statins at any given dose are significantly enhanced.

In addition, the peptides can be administered to reduce or eliminate one or more symptoms of osteoporosis and/or to prevent/inhibit the onset of one or more symptoms of osteoporosis.

VIII. Preferred Peptides and their Preparation.

A) Class A Amphipathic Helical Peptides.

It was a discovery of this invention that peptides comprising a class A amphipathic helix ("class A peptides"), are capable of mitigating one or more symptoms of atherosclerosis. Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) *Meth. Enzymol*, 128: 626–668). It is noted that the fourth exon of apo A-I, when folded into 3.667 residues/turn produces a class A amphipathic helical structure.

One particularly preferred class A peptide, designated 18A (see, e.g., Anantharamaiah (1986) *Meth. Enzymol,* 128: 626–668) was modified as described herein to produce peptides orally administratable and highly effective at inhibiting or preventing one or more symptoms of atherosclerosis. Without being bound by a particular theory, it is believed that the peptides of this invention act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) *Arteriosclerosis, Thrombosis, & Vascular Biology* 16: 328–338. Theoretically, a systematic substitution of residues in the nonpolar face of 18A with Phe could yield six peptides. Peptides with an additional 2, 3 and 4 Phe would have theoretical lipid affinity (λ) values of 13, 14 and 15 units, respectively. However, the λ values jumped four units if the additional Phe were increased from 4 to 5 (to 19 λ units). Increasing to 6 or 7 Phe would produce a less dramatic increase (to 20 and 21 λ units, respectively). Therefore, we chose 5 additional Phe (and hence the peptides designation as 5F). In one particularly preferred embodiment, the 5F peptide was blocked in that the amino terminal residue was acetylated and the carboxyl terminal residue was amidated.

The new class A peptide analog, 5F, inhibited lesion development in atherosclerosis-susceptible mice. The new peptide analog, 5F, was compared with mouse apo A-I (MoA-I) for efficacy in inhibiting diet-induced atherosclerosis in these mice using peptide dosages based on the study by Levine et al. (Levine et al. (1993) *Proc. Natl. Acad. Sci. USA* 90:12040–12044).

A number of other class A peptides were also produced and showed varying, but significant degrees of efficacy in mitigating one or more symptoms of atherosclerosis. A number of such peptides are illustrated in Table 1.

TABLE 1

Illustrative mimetics of the amphipathic helix of Apo A–I for use in this invention.

| Peptide Name | Amino Acid Sequence | SEQ ID NO. |
|---|---|---|
| 18A | D-W-L-K-A-F-Y-D-K-V-A-E-K-L-K-E-A-F | 4 |
| 2F | Ac-D-W-L-K-A-F-Y-D-K-V-A-E-K-L-K-E-A-F-NH$_2$ | 5 |
| 3F | Ac-D-W-F-K-A-F-Y-D-K-V-A-E-K-L-K-E-A-F-NH$_2$ | 6 |
| 3F14 | Ac-D-W-L-K-A-F-Y-D-K-V-A-E-K-F-K-E-A-F-NH$_2$ | 7 |
| 4F | Ac-D-W-F-K-A-F-Y-D-K-V-A-E-K-F-K-E-A-F-NH$_2$ | 8 |
| 5F | Ac-D-W-L-K-A-F-Y-D-K-V-F-E-K-F-K-E-F-F-NH$_2$ | 9 |
| 6F | Ac-D-W-L-K-A-F-Y-D-K-F-F-E-K-F-K-E-F-F-NH$_2$ | 10 |
| 7F | Ac-D-W-F-K-A-F-Y-D-K-F-F-E-K-F-K-E-F-F-NH$_2$ | 11 |
| | Ac-D-W-L-K-A-F-Y-D-K-V-A-E-K-L-K-E-F-F-NH$_2$ | 12 |
| | Ac-D-W-L-K-A-F-Y-D-K-V-F-E-K-F-K-E-A-F-NH$_2$ | 13 |
| | Ac-D-W-L-K-A-F-Y-D-K-V-A-E-K-F-K-E-F-F-NH$_2$ | 14 |
| | Ac-D-W-L-K-A-F-Y-D-K-V-A-E-K-F-K-E-F-F-NH$_2$ | 15 |
| | Ac-D-W-L-K-A-F-Y-D-K-V-F-E-K-F-K-E-F-F-NH$_2$ | 16 |
| | Ac-E-W-L-K-L-F-Y-E-K-V-L-E-K-F-K-E-A-F-NH$_2$ | 17 |
| | Ac-E-W-L-K-A-F-Y-D-K-V-A-E-K-L-K-E-A-F-NH$_2$ | 18 |
| | Ac-E-W-L-K-A-F-Y-D-K-V-A-E-K-L-K-E-F-F-NH$_2$ | 19 |
| | Ac-E-W-L-K-A-F-Y-D-K-V-F-E-K-F-K-E-A-F-NH$_2$ | 20 |
| | Ac-E-W-L-K-A-F-Y-D-K-V-F-E-K-L-K-E-F-F-NH$_2$ | 21 |
| | Ac-E-W-L-K-A-F-Y-D-K-V-A-E-K-F-K-E-F-F-NH$_2$ | 22 |
| | Ac-E-W-L-K-A-F-Y-D-K-V-F-E-K-F-K-E-F-F-NH$_2$ | 23 |
| | Ac-A-F-Y-D-K-V-A-E-K-L-K-E-A-F-NH$_2$ | 24 |
| | Ac-A-F-Y-D-K-V-A-E-K-F-K-E-A-F-NH$_2$ | 25 |
| | Ac-A-F-Y-D-K-V-A-E-K-F-K-E-A-F-NH$_2$ | 26 |
| | Ac-A-F-Y-D-K-F-F-E-K-F-K-E-F-F-NH$_2$ | 27 |
| | Ac-A-F-Y-D-K-F-F-E-K-F-K-E-F-F-NH$_2$ | 28 |
| | Ac-A-F-Y-D-K-V-A-E-K-F-K-E-A-F-NH$_2$ | 29 |
| | Ac-A-F-Y-D-K-V-A-E-K-L-K-E-F-F-NH$_2$ | 30 |
| | Ac-A-F-Y-D-K-V-F-E-K-F-K-E-A-F-NH$_2$ | 31 |
| | Ac-A-F-Y-D-K-V-F-E-K-L-K-E-A-F-NH$_2$ | 32 |
| | Ac-A-F-Y-D-K-V-A-E-K-F-K-E-F-F-NH$_2$ | 33 |
| | Ac-K-A-F-Y-D-K-V-F-E-K-F-K-E-F-NH$_2$ | 34 |
| | Ac-L-F-Y-E-K-V-L-E-K-F-K-E-A-F-NH$_2$ | 35 |
| | Ac-A-F-Y-D-K-V-A-E-K-F-K-E-A-F-NH$_2$ | 36 |
| | Ac-A-F-Y-D-K-V-A-E-K-L-K-E-F-F-NH$_2$ | 37 |
| | Ac-A-F-Y-D-K-V-F-E-K-F-K-E-A-F-NH$_2$ | 38 |
| | Ac-A-F-Y-D-K-V-F-E-K-L-K-E-F-F-NH$_2$ | 39 |
| | Ac-A-F-Y-D-K-V-A-E-K-F-K-E-F-F-NH$_2$ | 40 |
| | Ac-A-F-Y-D-K-V-F-E-K-F-K-E-F-F-NH$_2$ | 41 |
| | Ac-D-W-L-K-A-L-Y-D-K-V-A-E-K-L-K-E-A-L-NH$_2$ | 42 |
| | Ac-D-W-F-K-A-F-Y-E-K-V-A-E-K-L-K-E-F-F-NH$_2$ | 43 |
| | Ac-D-W-F-K-A-F-Y-E-K-F-F-E-K-F-K-E-F-F-NH$_2$ | 44 |
| | Ac-E-W-L-K-A-L-Y-E-K-V-A-E-K-L-K-E-A-L-NH$_2$ | 45 |
| | Ac-E-W-L-K-A-F-Y-E-K-V-A-E-K-L-K-E-A-F-NH$_2$ | 46 |
| | Ac-E-W-F-K-A-F-Y-E-K-V-A-E-K-L-K-E-F-F-NH$_2$ | 47 |
| | Ac-E-W-L-K-A-F-Y-E-K-V-F-E-K-F-K-E-F-F-NH$_2$ | 48 |
| | Ac-E-W-L-K-A-F-Y-E-K-F-F-E-K-F-K-E-F-F-NH$_2$ | 49 |
| | Ac-E-W-F-K-A-F-Y-E-K-F-F-E-K-F-K-E-F-F-NH$_2$ | 50 |
| | Ac-D-F-L-K-A-W-Y-D-K-V-A-E-K-L-K-E-A-W-NH$_2$ | 51 |
| | Ac-E-F-L-K-A-W-Y-E-K-V-A-E-K-L-K-E-A-W-NH$_2$ | 52 |
| | Ac-D-F-W-K-A-W-Y-D-K-V-A-E-K-L-K-E-W-W-NH$_2$ | 53 |
| | Ac-E-F-W-K-A-W-Y-E-K-V-A-E-K-L-K-E-W-W-NH$_2$ | 54 |
| | Ac-D-K-L-K-A-F-Y-D-K-V-F-E-W-A-K-E-A-F-NH$_2$ | 55 |
| | Ac-D-K-W-K-A-V-Y-D-K-F-A-E-A-F-K-E-F-L-NH$_2$ | 56 |
| | Ac-E-K-L-K-A-F-Y-E-K-V-F-E-W-A-K-E-A-F-NH$_2$ | 57 |
| | Ac-E-K-W-K-A-V-Y-E-K-F-A-E-A-F-K-E-F-L-NH$_2$ | 58 |
| | Ac-D-W-L-K-A-F-V-D-K-F-A-E-K-F-K-E-A-Y-NH$_2$ | 59 |
| | Ac-E-K-W-K-A-V-Y-E-K-F-A-E-A-F-K-E-F-L-NH$_2$ | 60 |
| | Ac-D-W-L-K-A-F-V-Y-D-K-V-F-K-L-K-E-F-F-NH$_2$ | 61 |
| | Ac-E-W-L-K-A-F-V-Y-E-K-V-F-K-L-K-E-F-F-NH$_2$ | 62 |
| | Ac-D-W-L-R-A-F-Y-D-K-V-A-E-K-L-K-E-A-F-NH$_2$ | 63 |
| | Ac-E-W-L-R-A-F-Y-E-K-V-A-E-K-L-K-E-A-F-NH$_2$ | 64 |
| | Ac-D-W-L-K-A-F-Y-D-R-V-A-E-K-L-K-E-A-F-NH$_2$ | 65 |
| | Ac-E-W-L-K-A-F-Y-E-R-V-A-E-K-L-K-E-A-F-NH$_2$ | 66 |
| | Ac-D-W-L-K-A-F-Y-D-K-V-A-E-R-L-K-E-A-F-NH$_2$ | 67 |
| | Ac-E-W-L-K-A-F-Y-E-K-V-A-E-R-L-K-E-A-F-NH$_2$ | 68 |

TABLE 1-continued

Illustrative mimetics of the amphipathic helix of Apo A—I for use in this invention.

| Peptide Name Amino Acid Sequence | SEQ ID NO. |
|---|---|
| Ac-D-W-L-K-A-F-Y-D-K-V-A-E-K-L-R-E-A-F-NH$_2$ | 69 |
| Ac-E-W-L-K-A-F-Y-E-K-V-A-E-K-L-R-E-A-F-NH$_2$ | 70 |
| Ac-D-W-L-K-A-F-Y-D-R-V-A-E-R-L-K-E-A-F-NH$_2$ | 71 |
| Ac-E-W-L-K-A-F-Y-E-R-V-A-E-R-L-K-E-A-F-NH$_2$ | 72 |
| Ac-D-W-L-R-A-F-Y-D-K-V-A-E-K-L-R-E-A-F-NH$_2$ | 73 |
| Ac-E-W-L-R-A-F-Y-E-K-V-A-E-K-L-R-E-A-F-NH$_2$ | 74 |
| Ac-D-W-L-R-A-F-Y-D-R-V-A-E-K-L-K-E-A-F-NH$_2$ | 75 |
| Ac-E-W-L-R-A-F-Y-E-R-V-A-E-K-L-K-E-A-F-NH$_2$ | 76 |
| Ac-D-W-L-K-A-F-Y-D-K-V-A-E-R-L-R-E-A-F-NH$_2$ | 77 |
| Ac-E-W-L-K-A-F-Y-E-K-V-A-E-R-L-R-E-A-F-NH$_2$ | 78 |
| Ac-D-W-L-R-A-F-Y-D-K-V-A-E-R-L-K-E-A-F-NH$_2$ | 79 |
| Ac-E-W-L-R-A-F-Y-E-K-V-A-E-R-L-K-E-A-F-NH$_2$ | 80 |
| D-W-L-K-A-F-Y-D-K-V-A-E-K-L-K-E-A-F-_P_-D-W-L-K-A-F-Y-D-K-V-A-E-K-L-K-E-A-F | 81 |
| D-W-L-K-A-F-Y-D-K-V-A-E-K-L-K-E-F-_P_-D-W-L-K-A-F-Y-D-K-V-A-E-K-L-K-E-F-F | 82 |
| D-W-F-K-A-F-Y-D-K-V-A-E-K-L-K-E-A-F-_P_-D-W-F-K-A-F-Y-D-K-V-A-E-K-L-K-E-A-F | 83 |
| D-K-L-K-A-F-Y-D-K-V-F-E-W-A-K-E-A-F-_P_-D-K-L-K-A-F-Y-D-K-V-F-E-W-L-K-E-A-F | 84 |
| D-K-W-K-A-V-Y-D-K-F-A-E-A-F-K-E-F-L-_P_-D-K-W-K-A-V-Y-D-K-F-A-E-A-F-K-E-F-L | 85 |
| D-W-F-K-A-F-Y-D-K-V-A-E-K-F-K-E-A-F-_P_-D-W-F-K-A-F-Y-D-K-V-A-E-K-F-K-E-A-F | 86 |
| D-W-L-K-A-F-V-Y-D-K-V-F-K-L-K-E-F-_P_-D-W-L-K-A-F-V-Y-D-K-V-F-K-L-K-E-F-F | 87 |
| D-W-L-K-A-F-Y-D-K-F-A-E-K-F-K-E-F-F-_P_-D-W-L-K-A-F-Y-D-K-F-A-E-K-F-K-E-F-F | 88 |
| Ac-E-W-F-K-A-F-Y-E-K-V-A-E-K-F-K-E-A-F-NH$_2$ | 89 |
| Ac-D-W-F-K-A-F-Y-D-K-V-A-E-K-F-NH$_2$ | 90 |
| Ac-F-K-A-F-Y-D-K-V-A-E-K-F-K-E-NH$_2$ | 91 |
| Ac-F-K-A-F-Y-E-K-V-A-E-K-F-K-E-NH$_2$ | 92 |
| NMA-F-K-A-F-Y-D-K-V-A-E-K-F-K-E-NH$_2$ | 93 |
| NMA-F-K-A-F-Y-E-K-V-A-E-K-F-K-E-NH$_2$ | 94 |
| NMA-D-W-F-K-A-F-Y-D-K-V-A-E-K-F-K-E-A-F-NH$_2$ | 95 |
| NMA-E-W-F-K-A-F-Y-E-K-V-A-E-K-F-K-E-A-F-NH$_2$ | 96 |
| NMA-A-F-Y-D-K-V-A-E-K-F-K-E-A-F-NH$_2$ | 97 |
| NMA-D-W-F-K-A-F-Y-D-K-V-A-E-K-F-NH$_2$ | 98 |
| Ac-D-W-L-K-A-F-Y-D-K-V-F-E-K-F-K-E-F-F-NH$_2$ | 99 |
| NMA-D-W-L-K-A-F-Y-D-K-V-F-E-K-F-K-E-F-F-NH$_2$ | 100 |
| Ac-E-W-L-K-A-F-Y-E-K-V-F-E-K-F-K-E-F-F-NH$_2$ | |
| NMA-E-W-L-K-A-F-Y-E-K-V-F-E-K-F-K-E-F-F-NH$_2$ | 101 |
| Ac-A-F-Y-D-K-V-F-E-K-F-K-E-F-F-NH$_2$ | |
| NMA-A-F-Y-D-K-V-F-E-K-F-K-E-F-F-NH$_2$ | 102 |
| Ac-A-F-Y-E-K-V-F-E-K-F-K-E-F-F-NH$_2$ | |
| NMA-A-F-Y-E-K-V-F-E-K-F-K-E-F-F-NH$_2$ | 103 |
| Ac-D-W-L-K-A-F-Y-D-K-V-F-E-K-F-K-E-F-NH$_2$ | |
| NMA-D-W-L-K-A-F-Y-D-K-V-F-E-K-F-K-E-F-NH$_2$ | 104 |
| Ac-E-W-L-K-A-F-Y-E-K-V-F-E-K-F-K-E-F-NH$_2$ | |
| NMA-E-W-L-K-A-F-Y-E-K-V-F-E-K-F-K-E-F-NH$_2$ | 105 |
| Ac-L-K-A-F-Y-D-K-V-F-E-K-F-K-E-NH$_2$ | |
| NMA-L-K-A-F-Y-D-K-V-F-E-K-F-K-E-NH$_2$ | 106 |
| Ac-L-K-A-F-Y-E-K-V-F-E-K-F-K-E-NH$_2$ | |
| NMA-L-K-A-F-Y-E-K-V-F-E-K-F-K-E-NH$_2$ | |

[1]Linkers are underlined.
NMA is N-Methyl Anthranilyl.

In certain preferred embodiments, the peptides include variations of 4F or D-4F where one or both aspartic acids (D) are replaced by glutamic acid (E). Also contemplated are peptides (e.g. 4F or D-4F) where 1, 2, 3, or 4 amino acids are deleted from the carboxyl terminus and/or 1, 2, 3, or 4 amino acids are deleted from the carboxyl terminus and/or one or both aspartic acids (D) are replaced by glutamic acid (E). In any of the peptides described herein, the N-terminus can be blocked and labeled using a mantyl moiety (e.g. N-methylanthranilyl).

While various peptides of Table 1, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g. every enantiomeric amino acid) of the peptides of Table 1 is a D-form amino acid.

It is also noted that Table Table 1 is not fully inclusive. Using the teaching provided herein, other suitable class A amphipathic helical peptides can routinely be produced (e.g. by conservative or semi-conservative substitutions (e.g. D replaced by E), extensions, deletions, and the like). Thus, for example, one embodiment utilizes truncations of any one or more of peptides shown hwerein (e.g. peptides identified by SEQ ID Nos:5–23 and 42—in Table 1). Thus, for example, SEQ ID NO:24 illustrates a peptide comprising 14 amino acids from the C-terminus of 18A comprising one or more D amino acids, while SEQ ID NOS:25–41 illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides. Thus, for example, the peptides illustrated heren can be coupled together (directly or through a linker (e.g. a carbon linker, or one or more amino acids) with one or more intervening amino acids). Illustrative polymeric peptides include 18A-Pro-18A and the peptides of SEQ ID NOs:81–88, in certain embodiments comprising one or more D amino acids, more preferably with every amino acid a D amino acid as described herein and/or having one or both termini protected.

B) Other Class A Amphipathic Helical Peptide Mimetics of apoA-I having Aromatic or Aliphatic Residues in the Non-polar Face.

In certain embodiments, this invention also provides modified class A amphiphathic helix peptides. Certain preferred peptides incorporate one or more aromatic residues at the center of the nonpolar face, e.g. $3F^{C\pi}$, (as present in 4F), or with one or more aliphatic residues at the center of the nonpolar face, e.g. $3F^{I\pi}$. Without being bound to a particular theory, we believe the central aromatic residues on the nonpolar face of the peptide $3F^{C\pi}$, due to the presence of π electrons at the center of the nonpolar face, allow water molecules to penetrate near the hydrophobic lipid alkyl chains of the peptide-lipid complex, which in turn would enable the entry of reactive oxygen species (such as lipid hydroperoxides) shielding them from the cell surface. Similarly, we also believe the peptides with aliphatic residues at the center of the nonpolar face, e.g. $3F^{I\pi}$, will act similarly but not quite as effectively as $3F^{C\pi}$.

Preferred peptides will convert pro-inflammatory HDL to anti-inflammatory HDL or make anti-inflammatory HDL more anti-inflammatory, and/or decrease LDL-induced monocyte chemotactic activity generated by artery wall cells equal to or greater than D4F or other peptides shown in Table 1. Peptides showing this activity are useful in ameliorating atherosclerosis and other inflammatory conditions such as rheumatoid arthritis, lupus erythematous, polyarteritis nodosa, osteoporosis, Alzheimer's disease, congestive heart failure, endothelial dysfunction, and viral illnesses such as influenza A and diseases such as multiple sclerosis.

TABLE 2

Examples of certain preferred peptides.

| Name | Sequence | SEQ ID NO |
|---|---|---|
| ($3F^{C\pi}$) | Ac-DKWKAVYDKFAEAFKEFL-NH$_2$ | 107 |
| ($3F^{I\pi}$) | Ac-DKLKAFYDKVFEWAKEAF-NH$_2$ | 108 |

C) Smaller Peptides.

It was also a surprising discovery that certain small peptides consisting of a minimum of three amino acids preferentially (but not necessarily) with one or more of the amino acids being the D-sterioisomer of the amino acid, and possessing hydrophobic domains to permit lipid protein interactions, and hydrophilic domains to permit a degree of water solubility also possess significant anti-inflammatory properties. Without being bound to a particular theory, it is believed that the peptides bind the "seeding molecules" required for the formation of pro-inflammatory oxidized phospholipids such as Ox-PAPC, POVPC, PGPC, and PEIPC. Since many inflammatory conditions are mediated at least in part by oxidized lipids, we believe that the peptides of this invention are effective in ameliorating conditions that are known or suspected to be due to the formation of biologically active oxidized lipids. These include, but are not limited to atherosclerosis, rheumatoid arthritis, lupus erythematous, polyarteritis nodosa, and osteoporosis. The "small peptides" typically range in length from 3 amino acids to about 15 amino acids, more preferably from about 4 amino acids to about 10 or 11 amino acids, and most preferably from about 4 to about 8 or 10 amino acids. The peptides are typically characterized by having hydrophobic terminal amino acids or terminal amino acids rendered hydrophobic by the attachment of one or more hydrophobic "protecting" groups.

In certain embodiments, the peptides can be characterized by Formula I, below:

$$X^1\text{-}X^2\text{-}X^3_n\text{-}X^4 \qquad \text{I}$$

where, n is 0 or 1, $X^1$ is a hydrophobic amino acid and/or bears a hydrophobic protecting group, $X^4$ is a hydrophobic amino acid and/or bears a hydrophobic protecting group; and when n is 0 $X^2$ is an acidic or a basic amino acid; when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid.

Longer peptides (e.g. up to 10, 11, or 15 amino acids) are also contemplated within the scope of this invention. Typically where the shorter peptides (e.g. peptides according to formula I) are characterized by an acidic, basic, aliphatic, or aromatic amino acid, the longer peptides are characterized by acidic, basic, aliphatic, or aromatic domains comprising two or more amino acids of that type.

1) Tripeptides.

It was discovered that certain tripeptides (3 amino acid peptides) can be synthesized that show desirable properties as described herein (e.g. the ability to convert pro-inflammatory HDL to anti-inflammatory HDL, the ability to decrease LDL-induced monocyte chemotactic activity generated by artery wall cells, the ability to increase pre-beta HDL, etc.). In certain embodiments, the peptides are characterized by formula I, wherein N is zero, shown below as Formula II:

$$X^1\text{-}X^2\text{-}X^4 \qquad \text{II}$$

where the end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). In certain embodiments, the $X^2$ amino acid is either acidic (e.g. aspartic acid, glutamic acid, etc.) or basic (e.g. histidine, arginine, lysine, etc.). The peptide can be all L- amino acids or include one or more or all D-amino acids.

Certain preferred tripeptides of this invention include, but are not limited to the peptides shown in Table 3.

TABLE 3

Examples of certain preferred tripeptides bearing hydrophobic blocking groups and acidic, basic, or histidine central amino acids.

| $X^1$ $X^2$ $X^3$ $X^4$ | | | SEQ ID NO |
|---|---|---|---|
| Boc-Lys(εBoc) | Arg | Ser(tBu)-OtBu | 109 |
| Boc-Lys(εBoc) | Arg | Thr(tBu)-OtBu | 110 |
| Boc-Trp | Arg | Ile-OtBu | 111 |
| Boc-Trp | Arg | Leu-OtBu | 112 |
| Boc-Phe | Arg | Ile-OtBu | 113 |
| Boc-Phe | Arg | Leu-OtBu | 114 |
| Boc-Lys(εBoc) | Glu | Ser(tBu)-OtBu | 115 |
| Boc-Lys(εBoc) | Glu | Thr(tBu)-OtBu | 116 |
| Boc-Lys(εBoc) | Asp | Ser(tBu)-OtBu | 117 |
| Boc-Lys(εBoc) | Asp | Thr(tBu)-OtBu | 118 |
| Boc-Lys(εBoc) | Arg | Ser(tBu)-OtBu | 119 |
| Boc-Lys(εBoc) | Arg | Thr(tBu)-OtBu | 120 |
| Boc-Leu | Glu | Ser(tBu)-OtBu | 121 |
| Boc-Leu | Glu | Thr(tBu)-OtBu | 122 |
| Fmoc-Trp | Arg | Ser(tBu)-OtBu | 123 |
| Fmoc-Trp | Asp | Ser(tBu)-OtBu | 124 |
| Fmoc-Trp | Glu | Ser(tBu)-OtBu | 125 |
| Fmoc-Trp | Arg | Ser(tBu)-OtBu | 126 |
| Boc-Lys(εBoc) | Glu | Leu-OtBu | 127 |
| Fmoc-Leu | Arg | Ser(tBu)-OtBu | 128 |
| Fmoc-Leu | Asp | Ser(tBu)-OtBu | 129 |
| Fmoc-Leu | Glu | Ser(tBu)-OtBu | 130 |
| Fmoc-Leu | Arg | Ser(tBu)-OtBu | 131 |
| Fmoc-Leu | Arg | Thr(tBu)-OtBu | 132 |
| Boc-Glu | Asp | Tyr(tBu)-OtBu | 133 |
| Fmoc-Lys(εFmoc) | Arg | Ser(tBu)-OtBu | 134 |
| Fmoc-Trp | Arg | Ile-OtBu | 135 |
| Fmoc-Trp | Arg | Leu-OtBu | 136 |
| Fmoc-Phe | Arg | Ile-OtBu | 137 |
| Fmoc-Phe | Arg | Leu-OtBu | 138 |
| Boc-Trp | Arg | Phe-OtBu | 139 |
| Boc-Trp | Arg | Tyr-OtBu | 140 |
| Fmoc-Trp | Arg | Phe-OtBu | 141 |
| Fmoc-Trp | Arg | Tyr-OtBu | 142 |
| Boc-Orn(δBoc) | Arg | Ser(tBu)-OtBu | 143 |
| Nicotinyl Lys(εBoc) | Arg | Ser(tBu)-OtBu | 144 |
| Nicotinyl Lys(εBoc) | Arg | Thr(tBu)-OtBu | 145 |
| Fmoc-Leu | Asp | Thr(tBu)-OtBu | 146 |
| Fmoc-Leu | Glu | Thr(tBu)-OtBu | 147 |
| Fmoc-Leu | Arg | Thr(tBu)-OtBu | 148 |
| Fmoc-norLeu | Arg | Ser(tBu)-OtBu | 149 |
| Fmoc-norLeu | Asp | Ser(tBu)-OtBu | 150 |
| Fmoc-norLeu | Glu | Ser(tBu)-OtBu | 151 |
| Fmoc-Lys(εBoc) | Arg | Ser(tBu)-OtBu | 152 |
| Fmoc-Lys(εBoc) | Arg | Thr(tBu)-OtBu | 153 |
| Fmoc-Lys(εBoc) | Glu | Ser(tBu)-OtBu | 154 |
| Fmoc-Lys(εBoc) | Glu | Thr(tBu)-OtBu | 155 |
| Fmoc-Lys(εBoc) | Asp | Ser(tBu)-OtBu | 156 |
| Fmoc-Lys(εBoc) | Asp | Thr(tBu)-OtBu | 157 |
| Fmoc-Lys(εBoc) | Glu | Leu-OtBu | 158 |
| Fmoc-Lys(εBoc) | Arg | Leu-OtBu | 159 |
| Fmoc-Lys(εFmoc) | Arg | Thr(tBu)-OtBu | 160 |
| Fmoc-Lys(εFmoc) | Glu | Ser(tBu)-OtBu | 161 |
| Fmoc-Lys(εFmoc) | Glu | Thr(tBu)-OtBu | 162 |
| Fmoc-Lys(εFmoc) | Asp | Ser(tBu)-OtBu | 163 |
| Fmoc-Lys(εFmoc) | Asp | Thr(tBu)-OtBu | 164 |
| Fmoc-Lys(εFmoc) | Arg | Ser(tBu)-OtBu | 165 |
| Fmoc-Lys(εFmoc)) | Glu | Leu-OtBu | 166 |
| Boc-Lys(εFmoc) | Asp | Ser(tBu)-OtBu | 167 |
| Boc-Lys(εFmoc) | Asp | Thr(tBu)-OtBu | 168 |
| Boc-Lys(εFmoc) | Arg | Thr(tBu)-OtBu | 169 |
| Boc-Lys(εFmoc) | Glu | Leu-OtBu | 170 |
| Boc-Orn(δFmoc) | Glu | Ser(tBu)-OtBu | 171 |
| Boc-Orn(δFmoc) | Asp | Ser(tBu)-OtBu | 172 |
| Boc-Orn(δFmoc) | Asp | Thr(tBu)-OtBu | 173 |
| Boc-Orn(δFmoc) | Arg | Thr(tBu)-OtBu | 174 |
| Boc-Orn(δFmoc) | Glu | Thr(tBu)-OtBu | 175 |
| Fmoc-Trp | Asp | Ile-OtBu | 176 |
| Fmoc-Trp | Arg | Ile-OtBu | 177 |
| Fmoc-Trp | Glu | Ile-OtBu | 178 |
| Fmoc-Trp | Asp | Leu-OtBu | 179 |
| Fmoc-Trp | Glu | Leu-OtBu | 180 |

TABLE 3-continued

Examples of certain preferred tripeptides bearing hydrophobic blocking groups and acidic, basic, or histidine central amino acids.

| $X^1$ | $X^2$ | $X^3 X^4$ | SEQ ID NO |
|---|---|---|---|
| Fmoc-Phe | Asp | Ile-OtBu | 181 |
| Fmoc-Phe | Asp | Leu-OtBu | 182 |
| Fmoc-Phe | Glu | Leu-OtBu | 183 |
| Fmoc-Trp | Arg | Phe-OtBu | 184 |
| Fmoc-Trp | Glu | Phe-OtBu | 185 |
| Fmoc-Trp | Asp | Phe-OtBu | 186 |
| Fmoc-Trp | Asp | Tyr-OtBu | 187 |
| Fmoc-Trp | Arg | Tyr-OtBu | 188 |
| Fmoc-Trp | Glu | Tyr-OtBu | 189 |
| Fmoc-Trp | Arg | Thr(tBu)-OtBu | 190 |
| Fmoc-Trp | Asp | Thr(tBu)-OtBu | 191 |
| Fmoc-Trp | Glu | Thr(tBu)-OtBu | 192 |
| Boc-Phe | Arg | norLeu-OtBu | 193 |
| Boc-Phe | Glu | norLeu-OtBu | 194 |
| Fmoc-Phe | Asp | norLeu-OtBu | 195 |
| Boc-Glu | His | Tyr(tBu)-OtBu | 196 |
| Boc-Leu | His | Ser(tBu)-OtBu | 197 |
| Boc-Leu | His | Thr(tBu)-OtBu | 198 |
| Boc-Lys(εBoc) | His | Ser(tBu)-OtBu | 199 |
| Boc-Lys(εBoc) | His | Thr(tBu)-OtBu | 200 |
| Boc-Lys(εBoc) | His | Leu-OtBu | 201 |
| Boc-Lys(εFmoc) | His | Ser(tBu)-OtBu | 202 |
| Boc-Lys(εFmoc) | His | Thr(tBu)-OtBu | 203 |
| Boc-Lys(εFmoc) | His | Leu-OtBu | 204 |
| Boc-Orn(δBoc) | His | Ser(tBu)-OtBu | 205 |
| Boc-Orn(δFmoc) | His | Thr(tBu)-OtBu | 206 |
| Boc-Phe | His | Ile-OtBu | 207 |
| Boc-Phe | His | Leu-OtBu | 208 |
| Boc-Phe | His | norLeu-OtBu | 209 |
| Boc-Phe | Lys | Leu-OtBu | 210 |
| Boc-Trp | His | Ile-OtBu | 211 |
| Boc-Trp | His | Leu-OtBu | 212 |
| Boc-Trp | His | Phe-OtBu | 213 |
| Boc-Trp | His | Tyr-OtBu | 214 |
| Boc-Phe | Lys | Leu-OtBu | 215 |
| Fmoc-Lys(εFmoc) | His | Ser(tBu)-OtBu | 216 |
| Fmoc-Lys(εFmoc) | His | Thr(tBu)-OtBu | 217 |
| Fmoc-Lys(εFmoc)) | His | Leu-OtBu | 218 |
| Fmoc-Leu | His | Ser(tBu)-OtBu | 219 |
| Fmoc-Leu | His | Thr(tBu)-OtBu | 220 |
| Fmoc-Lys(εBoc) | His | Ser(tBu)-OtBu | 221 |
| Fmoc-Lys(εBoc) | His | Thr(tBu)-OtBu | 222 |
| Fmoc-Lys(εBoc) | His | Leu-OtBu | 223 |
| Fmoc-Lys(εFmoc) | His | Ser(tBu)-OtBu | 224 |
| Fmoc-Lys(εFmoc) | His | Thr(tBu)-OtBu | 225 |
| Fmoc-norLeu | His | Ser(tBu)-OtBu | 226 |
| Fmoc-Phe | His | Ile-OtBu | 227 |
| Fmoc-Phe | His | Leu-OtBu | 228 |
| Fmoc-Phe | His | norLeu-OtBu | 229 |
| Fmoc-Trp | His | Ser(tBu)-OtBu | 230 |
| Fmoc-Trp | His | Ile-OtBu | 231 |
| Fmoc-Trp | His | Leu-OtBu | 232 |
| Fmoc-Trp | His | Phe-OtBu | 233 |
| Fmoc-Trp | His | Tyr-OtBu | 234 |
| Fmoc-Trp | His | Thr(tBu)-OtBu | 235 |
| Nicotinyl Lys(εBoc) | His | Ser(tBu)-OtBu | 236 |
| Nicotinyl Lys(εBoc) | His | Thr(tBu)-OtBu | 237 |

While the pepides of Table 3 are illustrated with particular protecting groups, it is noted that these groups may be substituted with other protecting groups as described herein and/or one or more of the shown protecting group can be eliminated.

2) Small Peptides with Central Acidic and Basic Amino Acids.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic amino acid and an acidic amino acid (e.g. in a 4 mer) or a basic domain and/or an acidic domain in a longer molecule.

These four-mers can be represented by Formula I in which $X^1$ and $X^4$ are hydrophobic and/or bear hydrophobic protecting group(s) as described herein and $X^2$ is acidic while $X^3$ is basic or $X^2$ is basic while $X^3$ is acidic. The peptide can be all L-amino acids or include one or more or all D-amino acids.

Certain preferred of this invention include, but are not limited to the peptides shown in Table 4.

TABLE 4

Illustrative examples of small peptides with central acidic and basic amino acids.

| $X^1$ | $X^2$ | $X^3$ | $X^4$ | SEQ ID NO |
|---|---|---|---|---|
| Boc-Lys(εBoc) | Arg | Asp | Ser(tBu)-OtBu | 238 |
| Boc-Lys(εBoc) | Arg | Asp | Thr(tBu)-OtBu | 239 |
| Boc-Trp | Arg | Asp | Ile-OtBu | 240 |
| Boc-Trp | Arg | Asp | Leu-OtBu | 241 |
| Boc-Phe | Arg | Asp | Leu-OtBu | 242 |
| Boc-Phe | Arg | Asp | Ile-OtBu | 243 |
| Boc-Phe | Arg | Asp | norLeu-OtBu | 244 |
| Boc-Phe | Arg | Glu | norLeu-OtBu | 245 |
| Boc-Phe | Arg | Glu | Ile-OtBu | 246 |
| Boc-Phe | Asp | Arg | Ile-OtBu | 247 |
| Boc-Phe | Glu | Arg | Ile-OtBu | 248 |
| Boc-Phe | Asp | Arg | Leu-OtBu | 249 |
| Boc-Phe | Arg | Glu | Leu-OtBu | 250 |
| Boc-Phe | Glu | Arg | Leu-OtBu | 251 |
| Boc-Phe | Asp | Arg | norLeu-OtBu | 252 |
| Boc-Phe | Glu | Arg | norLeu-OtBu | 253 |
| Boc-Lys(εBoc) | Glu | Arg | Ser(tBu)-OtBu | 254 |
| Boc-Lys(εBoc) | Glu | Arg | Thr(tBu)-OtBu | 255 |
| Boc-Lys(εBoc) | Asp | Arg | Ser(tBu)-OtBu | 256 |
| Boc-Lys(εBoc) | Asp | Arg | Thr(tBu)-OtBu | 257 |
| Boc-Lys(εBoc) | Arg | Glu | Ser(tBu)-OtBu | 258 |
| Boc-Lys(εBoc) | Arg | Glu | Thr(tBu)-OtBu | 259 |
| Boc-Leu | Glu | Arg | Ser(tBu)-OtBu | 260 |
| Boc-Leu | Glu | Arg | Thr(tBu)-OtBu | 261 |
| Fmoc-Trp | Arg | Asp | Ser(tBu)-OtBu | 262 |
| Fmoc-Trp | Asp | Arg | Ser(tBu)-OtBu | 263 |
| Fmoc-Trp | Glu | Arg | Ser(tBu)-OtBu | 264 |
| Fmoc-Trp | Arg | Glu | Ser(tBu)-OtBu | 265 |
| Boc-Lys(εBoc) | Glu | Arg | Leu-OtBu | 266 |
| Fmoc-Leu | Arg | Asp | Ser(tBu)-OtBu | 267 |
| Fmoc-Leu | Asp | Arg | Ser(tBu)-OtBu | 268 |
| Fmoc-Leu | Glu | Arg | Ser(tBu)-OtBu | 269 |
| Fmoc-Leu | Arg | Glu | Ser(tBu)-OtBu | 270 |
| Fmoc-Leu | Arg | Asp | Thr(tBu)-OtBu | 271 |
| Boc-Glu | Asp | Arg | Tyr(tBu)-OtBu | 272 |
| Fmoc-Lys(εFmoc) | Arg | Asp | Ser(tBu)-OtBu | 273 |
| Fmoc-Trp | Arg | Asp | Ile-OtBu | 274 |
| Fmoc-Trp | Arg | Asp | Leu-OtBu | 275 |
| Fmoc-Phe | Arg | Asp | Ile-OtBu | 276 |
| Fmoc-Phe | Arg | Asp | Leu-OtBu | 277 |
| Boc-Trp | Arg | Asp | Phe-OtBu | 278 |
| Boc-Trp | Arg | Asp | Tyr-OtBu | 279 |
| Fmoc-Trp | Arg | Asp | Phe-OtBu | 280 |
| Fmoc-Trp | Arg | Asp | Tyr-OtBu | 281 |
| Boc-Orn(δBoc) | Arg | Glu | Ser(tBu)-OtBu | 282 |
| Nicotinyl Lys(εBoc) | Arg | Asp | Ser(tBu)-OtBu | 283 |
| Nicotinyl Lys(εBoc) | Arg | Asp | Thr(tBu)-OtBu | 284 |
| Fmoc-Leu | Asp | Arg | Thr(tBu)-OtBu | 285 |
| Fmoc-Leu | Glu | Arg | Thr(tBu)-OtBu | 286 |
| Fmoc-Leu | Arg | Glu | Thr(tBu)-OtBu | 287 |
| Fmoc-norLeu | Arg | Asp | Ser(tBu)-OtBu | 288 |
| Fmoc-norLeu | Asp | Arg | Ser(tBu)-OtBu | 289 |
| Fmoc-norLeu | Glu | Arg | Ser(tBu)-OtBu | 290 |
| Fmoc-norLeu | Arg | Glu | Ser(tBu)-OtBu | 291 |
| Fmoc-Lys(εBoc) | Arg | Asp | Ser(tBu)-OtBu | 292 |
| Fmoc-Lys(εBoc) | Arg | Asp | Thr(tBu)-OtBu | 293 |
| Fmoc-Lys(εBoc) | Glu | Arg | Ser(tBu)-OtBu | 294 |
| Fmoc-Lys(εBoc) | Glu | Arg | Thr(tBu)-OtBu | 295 |
| Fmoc-Lys(εBoc) | Asp | Arg | Ser(tBu)-OtBu | 296 |
| Fmoc-Lys(εBoc) | Asp | Arg | Thr(tBu)-OtBu | 297 |
| Fmoc-Lys(εBoc) | Arg | Glu | Ser(tBu)-OtBu | 298 |
| Fmoc-Lys(εBoc) | Arg | Glu | Thr(tBu)-OtBu | 299 |
| Fmoc-Lys(εBoc) | Glu | Arg | Leu-OtBu | 300 |
| Fmoc-Lys(εBoc) | Arg | Glu | Leu-OtBu | 301 |
| Fmoc-Lys(εFmoc) | Arg | Asp | Thr(tBu)-OtBu | 302 |
| Fmoc-Lys(εFmoc) | Glu | Arg | Ser(tBu)-OtBu | 303 |
| Fmoc-Lys(εFmoc) | Glu | Arg | Thr(tBu)-OtBu | 304 |
| Fmoc-Lys(εFmoc) | Asp | Arg | Ser(tBu)-OtBu | 305 |
| Fmoc-Lys(εFmoc) | Asp | Arg | Thr(tBu)-OtBu | 306 |
| Fmoc-Lys(εFmoc) | Arg | Glu | Ser(tBu)-OtBu | 307 |

TABLE 4-continued

Illustrative examples of small peptides with central acidic and basic amino acids.

| X¹ | X² | X³ | X⁴ | SEQ ID NO |
|---|---|---|---|---|
| Fmoc-Lys(εFmoc) | Arg | Glu | Thr(tBu)-OtBu | 308 |
| Fmoc-Lys(εFmoc)) | Glu | Arg | Leu-OtBu | 309 |
| Boc-Lys(εFmoc) | Arg | Asp | Ser(tBu)-OtBu | 310 |
| Boc-Lys(εFmoc) | Arg | Asp | Thr(tBu)-OtBu | 311 |
| Boc-Lys(εFmoc) | Glu | Arg | Ser(tBu)-OtBu | 312 |
| Boc-Lys(εFmoc) | Glu | Arg | Thr(tBu)-OtBu | 313 |
| Boc-Lys(εFmoc) | Asp | Arg | Ser(tBu)-OtBu | 314 |
| Boc-Lys(εFmoc) | Asp | Arg | Thr(tBu)-OtBu | 315 |
| Boc-Lys(εFmoc) | Arg | Glu | Ser(tBu)-OtBu | 316 |
| Boc-Lys(εFmoc) | Arg | Glu | Thr(tBu)-OtBu | 317 |
| Boc-Lys(εFmoc) | Glu | Arg | Leu-OtBu | 318 |
| Boc-Orn(δFmoc) | Arg | Glu | Ser(tBu)-OtBu | 319 |
| Boc-Orn(δFmoc) | Glu | Arg | Ser(tBu)-OtBu | 320 |
| Boc-Orn(δFmoc) | Arg | Asp | Ser(tBu)-OtBu | 321 |
| Boc-Orn(δFmoc) | Asp | Arg | Ser(tBu)-OtBu | 322 |
| Boc-Orn(δFmoc) | Asp | Arg | Thr(tBu)-OtBu | 323 |
| Boc-Orn(δFmoc) | Arg | Asp | Thr(tBu)-OtBu | 324 |
| Boc-Orn(δFmoc) | Glu | Arg | Thr(tBu)-OtBu | 325 |
| Boc-Orn(δFmoc) | Arg | Glu | Thr(tBu)-OtBu | 326 |
| Fmoc-Trp | Asp | Arg | Ile-OtBu | 327 |
| Fmoc-Trp | Arg | Glu | Ile-OtBu | 328 |
| Fmoc-Trp | Glu | Arg | Ile-OtBu | 329 |
| Fmoc-Trp | Asp | Arg | Leu-OtBu | 330 |
| Fmoc-Trp | Arg | Glu | Leu-OtBu | 331 |
| Fmoc-Trp | Glu | Arg | Leu-OtBu | 332 |
| Fmoc-Phe | Asp | Arg | Ile-OtBu | 333 |
| Fmoc-Phe | Arg | Glu | Ile-OtBu | 334 |
| Fmoc-Phe | Glu | Arg | Ile-OtBu | 335 |
| Fmoc-Phe | Asp | Arg | Leu-OtBu | 336 |
| Fmoc-Phe | Arg | Glu | Leu-OtBu | 337 |
| Fmoc-Phe | Glu | Arg | Leu-OtBu | 338 |
| Fmoc-Trp | Arg | Asp | Phe-OtBu | 339 |
| Fmoc-Trp | Arg | Glu | Phe-OtBu | 340 |
| Fmoc-Trp | Glu | Arg | Phe-OtBu | 341 |
| Fmoc-Trp | Asp | Arg | Tyr-OtBu | 342 |
| Fmoc-Trp | Arg | Glu | Tyr-OtBu | 343 |
| Fmoc-Trp | Glu | Arg | Tyr-OtBu | 344 |
| Fmoc-Trp | Arg | Asp | Thr(tBu)-OtBu | 345 |
| Fmoc-Trp | Asp | Arg | Thr(tBu)-OtBu | 346 |
| Fmoc-Trp | Arg | Glu | Thr(tBu)-OtBu | 347 |
| Fmoc-Trp | Glu | Arg | Thr(tBu)-OtBu | 348 |
| Fmoc-Phe | Arg | Asp | norLeu-OtBu | 349 |
| Fmoc-Phe | Arg | Glu | norLeu-OtBu | 350 |
| Boc-Phe | Lys | Asp | Leu-OtBu | 351 |
| Boc-Phe | Asp | Lys | Leu-OtBu | 352 |
| Boc-Phe | Lys | Glu | Leu-OtBu | 353 |
| Boc-Phe | Glu | Lys | Leu-OtBu | 354 |
| Boc-Phe | Lys | Asp | Ile-OtBu | 355 |
| Boc-Phe | Asp | Lys | Ile-OtBu | 356 |
| Boc-Phe | Lys | Glu | Ile-OtBu | 357 |
| Boc-Phe | Glu | Lys | Ile-OtBu | 358 |
| Boc-Phe | Lys | Asp | norLeu-OtBu | 359 |
| Boc-Phe | Asp | Lys | norLeu-OtBu | 360 |
| Boc-Phe | Lys | Glu | norLeu-OtBu | 361 |
| Boc-Phe | Glu | Lys | norLeu-OtBu | 362 |
| Boc-Phe | His | Asp | Leu-OtBu | 363 |
| Boc-Phe | Asp | His | Leu-OtBu | 364 |
| Boc-Phe | His | Glu | Leu-OtBu | 365 |
| Boc-Phe | Glu | His | Leu-OtBu | 366 |
| Boc-Phe | His | Asp | Ile-OtBu | 367 |
| Boc-Phe | Asp | His | Ile-OtBu | 368 |
| Boc-Phe | His | Glu | Ile-OtBu | 369 |
| Boc-Phe | Glu | His | Ile-OtBu | 370 |
| Boc-Phe | His | Asp | norLeu-OtBu | 371 |
| Boc-Phe | Asp | His | norLeu-OtBu | 372 |
| Boc-Phe | His | Glu | norLeu-OtBu | 373 |
| Boc-Phe | Glu | His | norLeu-OtBu | 374 |
| Boc-Lys(εBoc) | Lys | Asp | Ser(tBu)-OtBu | 375 |
| Boc-Lys(εBoc) | Asp | Lys | Ser(tBu)-OtBu | 376 |
| Boc-Lys(εBoc) | Lys | Glu | Ser(tBu)-OtBu | 377 |
| Boc-Lys(εBoc) | Glu | Lys | Ser(tBu)-OtBu | 378 |
| Boc-Lys(εBoc) | His | Asp | Ser(tBu)-OtBu | 379 |
| Boc-Lys(εBoc) | Asp | His | Ser(tBu)-OtBu | 380 |

TABLE 4-continued

Illustrative examples of small peptides with central acidic and basic amino acids.

| $X^1$ | $X^2$ | $X^3$ | $X^4$ | SEQ ID NO |
|---|---|---|---|---|
| Boc-Lys(εBoc) | His | Glu | Ser(tBu)-OtBu | 381 |
| Boc-Lys(εBoc) | Glu | His | Ser(tBu)-OtBu | 382 |

While the pepides of Table 4 are illustrated with particular protecting groups, it is noted that these groups may be substituted with other protecting groups as described herein and/or one or more of the shown protecting group can be eliminated.

3) Small Peptides having either an Acidic or Basic Amino Acid in the Center Together with a Central Aliphatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups. End amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aliphatic amino acid (e.g. in a 4 mer) or a basic domain or an acidic domain and an aliphatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aliphatic or $X^2$ is aliphatic while $X^3$ is acidic or basic. The peptide can be all L-amino acids or include one, or more, or all D-amino acids.

Certain preferred of this invention include, but are not limited to the peptides shown in Table 5.

TABLE 5

Examples of certain preferred peptides having either an acidic or basic amino acid in the center together with a central aliphatic amino acid.

| $X^1$ | $X^2$ | $X^3$ | $X^4$ | SEQ ID NO |
|---|---|---|---|---|
| Fmoc-Lys(εBoc) | Leu | Arg | Ser(tBu)-OtBu | 383 |
| Fmoc-Lys(εBoc) | Arg | Leu | Ser(tBu)-OtBu | 384 |
| Fmoc-Lys(εBoc) | Leu | Arg | Thr(tBu)-OtBu | 385 |
| Fmoc-Lys(εBoc) | Arg | Leu | Thr(tBu)-OtBu | 386 |
| Fmoc-Lys(εBoc) | Glu | Leu | Ser(tBu)-OtBu | 387 |
| Fmoc-Lys(εBoc) | Leu | Glu | Ser(tBu)-OtBu | 388 |
| Fmoc-Lys(εBoc) | Glu | Leu | Thr(tBu)-OtBu | 389 |
| Fmoc-Lys(εBoc) | Leu | Glu | Thr(tBu)-OtBu | 390 |
| Fmoc-Lys(εFmoc) | Leu | Arg | Ser(tBu)-OtBu | 391 |
| Fmoc-Lys(εFmoc) | Leu | Arg | Thr(tBu)-OtBu | 392 |
| Fmoc-Lys(εFmoc) | Glu | Leu | Ser(tBu)-OtBu | 393 |
| Fmoc-Lys(εFmoc) | Glu | Leu | Thr(tBu)-OtBu | 394 |
| Boc-Lys(Fmoc) | Glu | Ile | Thr(tBu)-OtBu | 395 |
| Boc-Lys(εFmoc) | Leu | Arg | Ser(tBu)-OtBu | 396 |
| Boc-Lys(εFmoc) | Leu | Arg | Thr(tBu)-OtBu | 397 |
| Boc-Lys(εFmoc) | Glu | Leu | Ser(tBu)-OtBu | 398 |
| Boc-Lys(εFmoc) | Glu | Leu | Thr(tBu)-OtBu | 399 |
| Boc-Lys(εBoc) | Leu | Arg | Ser(tBu)-OtBu | 400 |
| Boc-Lys(εBoc) | Arg | Phe | Thr(tBu)-OtBu | 401 |
| Boc-Lys(εBoc) | Leu | Arg | Thr(tBu)-OtBu | 402 |
| Boc-Lys(εBoc) | Glu | Ile | Thr(tBu) | 403 |
| Boc-Lys(εBoc) | Glu | Val | Thr(tBu) | 404 |
| Boc-Lys(εBoc) | Glu | Ala | Thr(tBu) | 405 |
| Boc-Lys(εBoc) | Glu | Gly | Thr(tBu) | 406 |
| Boc-Lys(εBoc) | Glu | Leu | Ser(tBu)-OtBu | 407 |
| Boc-Lys(εBoc) | Glu | Leu | Thr(tBu)-OtBu | 408 |

While the pepides of Table 5 are illustrated with particular protecting groups, it is noted that these groups may be substituted with other protecting groups as described herein and/or one or more of the shown protecting group can be eliminated.

4) Small Peptides having either an Acidic or Basic Amino Acid in the Center Together with a Central Aromatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aromatic amino acid (e.g. in a 4 mer) or a basic domain or an acidic domain and an aromatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aromatic or $X^2$ is aromatic while $X^3$ is acidic or basic. The peptide can be all L-amino acids or include one, or more, or all D-amino acids. Five-mers can be represented by a minor modification of Formula I in which $X^5$ is inserted as shown in Table 6 and in which $X^5$ is typically an aromatic amino acid.

Certain preferred of this invention include, but are not limited to the peptides shown in Table 6.

TABLE 6

Examples of certain preferred peptides having either an acidic or basic amino acid in the center together with a central aromatic amino acid.

| $X^1$ | $X^2$ | $X^3$ | $X^4$ | $X^5$ | SEQ ID NO |
|---|---|---|---|---|---|
| Fmoc-Lys(εBoc) | Arg | Trp | | Tyr(tBu)-OtBu | 409 |
| Fmoc-Lys(εBoc) | Trp | Arg | | Tyr(tBu)-OtBu | 410 |
| Fmoc-Lys(εBoc) | Arg | Tyr | | Trp-OtBu | 411 |
| Fmoc-Lys(εBoc) | Tyr | Arg | | Trp-OtBu | 412 |
| Fmoc-Lys(εBoc) | Arg | Tyr | Trp | Thr(tBu)-OtBu | 413 |
| Fmoc-Lys(εBoc) | Arg | Tyr | | Thr(tBu)-OtBu | 414 |
| Fmoc-Lys(εBoc) | Arg | Trp | | Thr(tBu)-OtBu | 415 |
| Fmoc-Lys(εFmoc) | Arg | Trp | | Tyr(tBu)-OtBu | 416 |
| Fmoc-Lys(εFmoc) | Arg | Tyr | | Trp-OtBu | 417 |
| Fmoc-Lys(εFmoc) | Arg | Tyr | Trp | Thr(tBu)-OtBu | 418 |
| Fmoc-Lys(εFmoc) | Arg | Tyr | | Thr(tBu)-OtBu | 419 |
| Fmoc-Lys(εFmoc) | Arg | Trp | | Thr(tBu)-OtBu | 420 |
| Boc-Lys(εFmoc) | Arg | Trp | | Tyr(tBu)-OtBu | 421 |
| Boc-Lys(εFmoc) | Arg | Tyr | | Trp-OtBu | 422 |
| Boc-Lys(εFmoc) | Arg | Tyr | Trp | Thr(tBu)-OtBu | 423 |
| Boc-Lys(εFmoc) | Arg | Tyr | | Thr(tBu)-OtBu | 424 |
| Boc-Lys(εFmoc) | Arg | Trp | | Thr(tBu)-OtBu | 425 |
| Boc-Glu | Lys(εFmoc) | Arg | | Tyr(tBu)-OtBu | 426 |
| Boc-Lys(εBoc) | Arg | Trp | | Tyr(tBu)-OtBu | 427 |
| Boc-Lys(εBoc) | Arg | Tyr | | Trp-OtBu | 428 |
| Boc-Lys(εBoc) | Arg | Tyr | Trp | Thr(tBu)-OtBu | 429 |
| Boc-Lys(εBoc) | Arg | Tyr | | Thr(tBu)-OtBu | 430 |
| Boc-Lys(εBoc) | Arg | Phe | | Thr(tBu)-OtBu | 431 |
| Boc-Lys(εBoc) | Arg | Trp | | Thr(tBu)-OtBu | 432 |

While the pepides of Table 6 are illustrated with particular protecting groups, it is noted that these groups may be substituted with other protecting groups as described herein and/or one or more of the shown protecting group can be eliminated.

5) Small Peptides having Aromatic Amino Acids or Aromatic Amino Acids Separated by Histidine(s) at the Center.

In certain embodiments, the peptides of this invention are characterized by π electrons that are exposed in the center of the molecule which allow hydration of the particle and that allow the peptide particles to trap pro-inflammatory oxidized lipids such as fatty acid hydroperoxides and phospholipids that contain an oxidation product of arachidonic acid at the sn-2 position.

In certain embodiments, these peptides consist of a minimum of 4 amino acids and a maximum of about 10 amino acids, preferentially (but not necessarily) with one or more of the amino acids being the D-sterioisomer of the amino acid, with the end amino acids being hydrophobic either because of a hydrophobic side chain or because the terminal amino acid(s) bear one or more hydrophobic blocking group(s), (e.g., an N-terminus blocked with Boc-, Fmoc-, Nicotinyl-, and the like, and a C-terminus blocked with (tBu)-OtBu groups and the like). Instead of having an acidic or basic amino acid in the center, these peptides generally have an aromatic amino acid at the center or have aromatic amino acids separated by histidine in the center of the peptide.

Certain preferred of this invention include, but are not limited to the peptides shown in Table 7.

TABLE 7

Examples of peptides having aromatic amino acids in the center or aromatic amino acids or aromatic domains separated by one or more histidines.

| $X^1$ | $X^2$ | $X^3$ | $X^4$ | $X^5$ | SEQ ID NO |
|---|---|---|---|---|---|
| Boc-Lys(εBoc) | Phe | Trp | Phe | Ser(tBu)-OtBu | 433 |
| Boc-Lys(εBoc) | Phe | Trp | Phe | Thr(tBu)-OtBu | 434 |
| Boc-Lys(εBoc) | Phe | Tyr | Phe | Ser(tBu)-OtBu | 435 |
| Boc-Lys(εBoc) | Phe | Tyr | Phe | Thr(tBu)-OtBu | 436 |
| Boc-Lys(εBoc) | Phe | His | Phe | Ser(tBu)-OtBu | 437 |
| Boc-Lys(εBoc) | Phe | His | Phe | Thr(tBu)-OtBu | 438 |
| Boc-Lys(εBoc) | Val | Phe | Phe-Tyr | Ser(tBu)-OtBu | 439 |
| Nicotinyl-Lys(εBoc) | Phe | Trp | Phe | Ser(tBu)-OtBu | 440 |
| Nicotinyl-Lys(εBoc) | Phe | Trp | Phe | Thr(tBu)-OtBu | 441 |
| Nicotinyl-Lys(εBoc) | Phe | Tyr | Phe | Ser(tBu)-OtBu | 442 |
| Nicotinyl-Lys(εBoc) | Phe | Tyr | Phe | Thr(tBu)-OtBu | 443 |
| Nicotinyl-Lys(εBoc) | Phe | His | Phe | Ser(tBu)-OtBu | 444 |
| Nicotinyl-Lys(εBoc) | Phe | His | Phe | Thr(tBu)-OtBu | 445 |
| Boc-Leu | Phe | Trp | Phe | Thr(tBu)-OtBu | 446 |
| Boc-Leu | Phe | Trp | Phe | Ser(tBu)-OtBu | 447 |

While the pepides of Table 7 are illustrated with particular protecting groups, it is noted that these groups may be substituted with other protecting groups as described herein and/or one or more of the shown protecting group can be eliminated.

6) Summary of Tripeptides and Tetrapeptides.

For the sake of clarity, a number of tripeptides and tetrapeptides of this invention are generally summarized below in Table 8.

TABLE 8

General structure of certain peptides of this invention.

| $X^1$ | $X^2$ | $X^3$ | $X^4$ |
|---|---|---|---|
| hydrophobic side chain or hydrophobic protecting group(s) | Acidic or Basic | — | hydrophobic side chain or hydrophobic protecting group(s) |
| hydrophobic side chain or hydrophobic protecting group(s) | Basic | Acidic | hydrophobic side chain or hydrophobic protecting group(s) |
| hydrophobic side chain or hydrophobic protecting group(s) | Acidic | Basic | hydrophobic side chain or hydrophobic protecting group(s) |
| hydrophobic side chain or hydrophobic protecting group(s) | Acidic or Basic | Aliphatic | hydrophobic side chain or hydrophobic protecting group(s) |
| hydrophobic side chain or hydrophobic protecting group(s) | Aliphatic | Acidic or Basic | hydrophobic side chain or hydrophobic protecting group(s) |
| hydrophobic side chain or hydrophobic protecting group(s) | Acidic or Basic | Aromatic | hydrophobic side chain or hydrophobic protecting group(s) |
| hydrophobic side chain or hydrophobic protecting group(s) | Aromatic | Acidic or Basic | hydrophobic side chain or hydrophobic protecting group(s) |
| hydrophobic side chain or hydrophobic protecting group(s) | Aromatic | His Aromatic | hydrophobic side chain or hydrophobic protecting group(s) |

Where longer peptides are desired, $X^2$ and $X^3$ can represent domains (e.g. regions of two or more amino acids of the specified type) rather than individual amino acids. Table 8 is intended to be illustrative and not limiting. Using the teaching provided herein, other suitable peptides can readily be identified.

D) Other Peptide Modifications.

It was a surprising discovery that the peptides described herein, particular when they incorporated one or more D-amino acids, they retained their activity and could also be administered orally. Moreover this oral administration resulted in relatively efficient uptake and significant serum half-life thereby providing an efficacious method of mitigating one or more symptoms of atherosclerosis or other pathologies characterized by an inflammatory process.

Using the teaching provided herein, one of skill can routinely modify the illustrated peptides to produce other similar peptides of this invention. For example, routine conservative or semi-conservative substitutions (e.g. E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328–338. The peptides can be lengthened or shortened as long as the class A α-helix structure is preserved. In addition, substitutions can be made to render the resulting peptide more similar to peptide(s) endogenously produced by the subject species.

In certain embodiments, the peptides of this invention comprise "D" forms of the peptides described in U.S. Pat. No. 4,643,988, more preferably "D" forms having one or both termini coupled to protecting groups. In certain embodiments, at least 50% of the enantiomeric amino acids are "D" form, more preferably at least 80% of the enantiomeric amino acids are "D" form, and most preferably at least 90% or even all of the enantiomeric amino acids are "D" form amino acids.

While, in certain embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

In addition to the peptides described herein, peptidomimetics are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS* p. 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g, 4F, SEQ ID NO: 258 described herein), but have one or more peptide linkages optionally replaced by a linkage selected from the group consisting of: —CH$_2$NH—, —CH$_2$S—, —CH$_2$—CH$_2$—, —CH═CH— (cis and trans), —COCH$_2$—, —CH(OH)CH$_2$—, —CH$_2$SO—, etc. by methods known in the art and further described in the following references: Spatola (1983) p. 267 in *Chemistry and Biochemistry of Amino Acids, Peptides, and Proteins*, B. Weinstein, eds., Marcel Dekker, New York,; Spatola (1983) Vega Data (3) *Peptide Backbone Modifications*. (general review); Morley (1980) *Trends Pharm Sci* pp. 463–468 (general review); Hudson et al. (1979) *Int J Pept Prot Res* 14:177–185 (—CH$_2$NH—, CH$_2$CH$_2$—); Spatola et al. (1986) *Life Sci* 38:1243–1249 (—CH$_2$—S); Hann, (1982) *J Chem Soc Perkin Trans* I 307–314 (—CH—CH—, cis and trans); Almquist et al. (1980) *J Med Chem.* 23:1392–1398 (—COCH$_2$—); Jennings-White et al.(1982) *Tetrahedron Lett.* 23:2533 (—COCH$_2$—); Szelke, M. et al., European Appln. EP 45665 (1982) CA: 97:39405 (1982) (—CH(OH)CH2—); Holladay et al. (1983) *Tetrahedron Lett* 24:4401–4404 (—C(OH)CH$_2$—); and Hruby (1982) *Life Sci.,* 31:189–199 (—CH$_2$—S—)).

A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circular permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

IX. Functional Assays of Peptides.

Certain peptides of this invention are desctribed herein by various formulas (e.g. Formula I, above) and/or by particular sequences. In certain embodiments, however, preferred peptides of this invention are characterized by one or more of the following functional properties:

1 They convert pro-inflammatory HDL to anti-inflammatory HDL or make anti-inflammatory HDL more anti-inflammatory;
2 They decrease LDL-induced monocyte chemotactic activity generated by artery wall cells;
3 They stimulate the formation and cycling of pre-β HDL;
4 They raise HDL cholesterol; and/or
5 They increase HDL paraoxonase activity.

The specific peptides disclosed herein, and/or peptides corresponding to the various formulas described herein can readily be tested for one or more of these activities as desired.

Methods of screening for each of these functional properties are well known to those of skill in the art. In addition, such screens are illustrated herein in the Examples. In particular, it is noted that assays for monocyte chemotactic activity, HDL cholesterol, and HDL HDL paraoxonase activity are illustrated in PCT/US01/26497 (WO 02/15923). Assays for determining HDL inflammatory and/or anti-inflammatory properties were performed as described below.

A) Determination of HDL Inflammatory/Anti-inflammatory Properties

1) Monocyte Chemotactic Activity (MCA) Assay

Lipoproteins, human artery wall cocultures, and monocytes were prepared and monocyte chemotactic activity (MCA) was determined as previously described (Van Lenten et al. (2002) *Circulation,* 106: 1127–1132). Induction of MCA by a standard control LDL was determined in the absence or presence of the subject's HDL. Values in the absence of HDL were normalized to 1.0. Values greater than 1.0 after the addition of HDL indicated pro-inflammatory HDL; values less than 1.0 indicated anti-inflammatory HDL.

2) Cell-free Assay

The cell-free assay was a modification of a previously published method[9] using PEIPC as the fluorescence-inducing agent. Briefly, HDL was isolated by dextran sulfate method. Sigma "HDL cholesterol reagent" (Catalog No. 352-3) containing dextran sulfate and magnesium ions was dissolved in distilled water (10.0 mg/ml). Fifty microliters of dextran sulfate solution was mixed with 500 µl of the test plasma and incubated at room temperature for 5 min and subsequently centrifuged at 8,000 g for 10 min. The supernatant containing HDL was used in the experiments after cholesterol determination using a cholesterol assay kit (Cat. No. 2340-200, Thermo DMA Company, Arlington, Tex.). We have previously reported (Navab et al. (2001) *J Lipid Res,* 1308–1317) that HDL isolated by this method inactivates bioactive phospholipids to a similar extent as compared with HDL that has been isolated by conventional ultracentrifuge methods. To determine the inflammatory/anti-inflammatory properties of HDL samples from patients and controls, the change in fluorescence intensity as a result of the oxidation of DCFH by PEIPC in the absence or presence of the test HDL was used. DCFH-DA was dissolved in fresh methanol at 2.0 mg/ml and was incubated at room temperature and protected from light for 30 min. resulting in the release of DCFH. The assay was adapted for analyzing a large number of samples with a plate reader. Flat-bottom, black, polystyrene microtiter plates (Microfluor2,Cat. No. 14-245-176, Fisher) were utilized for this purpose. Ten µl of PEIPC solution (final concentration of 50 µg/ml), and 90 µl of HDL-containing dextran sulfate supernatant (final concentration of 10 µg/ml cholesterol), were aliquoted into microtiter plates and mixed. The plates were then incubated at 37° C. on a rotator for 1.0 hr. Ten µl of DCFH solution (0.2 mg/ml) was then added to each well, mixed and incubated for an additional 2 hrs at 37° C. with rotation. The fluorescence was subsequently determined with a plate reader (Spectra Max, Gemini XS; Molecular Devices) at an excitation wavelength of 485 nm and emission wavelength of 530 nm and cutoff of 515 nm with the photomultiplier sensitivity set at "medium". Values for intra- and interassay variability were 5.3±1.7% and 7.1±3.2%, respectively. Values in the absence of HDL were normalized to 1.0. Values greater than 1.0 after the addition of the test HDL indicated pro-inflammatory HDL; values less than 1.0 indicated anti-inflammatory HDL.

3) Other Procedures

Plasma levels of interleukin-6 (IL-6) and tumor necrosis factor-α (TNF-α) were determined by previously published methods (Scheidt-Nave et al. (2001) *J Clin Endocrinol Metab.,* 86:2032–2042; Piguet et al. (1987) *J Experiment Med.,* 166, 1280–1289). Plasma total cholesterol, triglycerides, LDL-cholesterol, HDL-cholesterol and glucose were determined as previously described (Navab et al. (1997) J Clin Invest, 99:2005–2019) using kits (Sigma), and hs-CRP levels (Rifai et al. (1999) *Clin Chem.,* 45:2136–2141) were determined using a sandwich enzyme immunoassay from Immunodiagnostik (ALPCO Diagnostics, Windham, N.H.). Statistical significance was determined with model I ANOVA, and significance was defined as a value of $p<0.05$.

It is noted that these methods are merely illustrative and not intended to be limiting. Using the teachings provided herein, other assays for the desired functional proeperties of the peptides can readily be provided.

X. Peptide Preparation.

A) General Synthesis Methods.

The peptides used in this invention can be chemically synthesized using standard chemical peptide synthesis techniques or, particularly where the peptide does not comprise "D" amino acid residues, the peptide can readily be recombinantly expressed. Where the "D" polypeptides are recombinantly expressed, a host organism (e.g. bacteria, plant, fungal cells, etc.) can be cultured in an environment where one or more of the amino acids is provided to the organism exclusively in a D form. Recombinantly expressed peptides in such a system then incorporate those D amino acids.

In certain embodiments, D amino acids can be incorporated in recombinantly expressed peptides using modified amino acyl-tRNA synthetases that recognize D-amino acids.

In certain preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3–284 in *The Peptides: Analysis, Synthesis, Biology.* Vol. 2: *Special*

*Methods in Peptide Synthesis*, Part A.; Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

In one embodiment, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are describe in a miniprint supplement accompanying Anantharamaiah et al. (1985) *J. Biol. Chem.*, 260(16): 10248–10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, particularly in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

B) Incorporating D-form Amino Acids.

D-amino acids can be incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be completely omitted or incorporated at any position in the peptide as desired. Thus, for example, in certain embodiments, the peptide can comprise a single D-amino acid, while in other embodiments, the peptide comprises at least two, generally at least three, more generally at least four, most generally at least five, preferably at least six, more preferably at least seven and most preferably at least eight D amino acids. In particularly preferred embodiments, essentially every other (enantiomeric) amino acid is a D-form amino acid. In certain embodiments at least 90%, preferably at least 90%, more preferably at least 95% of the enantiomeric amino acids are D-form amino acids. In one particularly preferred embodiment, essentially every enantiomeric amino acid is a D-form amino acid.

C) Solution Phase Synthesis Methods.

In certain embodiments, the peptides of this inventioin can readily be synthesized using solution phase methods. One such synthesis scheme is illustrated in FIGS. 1 and 2.

In this scheme, A,B, C and D represent amino acids in the desired peptide. X-represents a permanent α-amino protecting group. Y-represents a permanent α-carboxyl protecting group. Letters m and n represent side chain protecting groups if the N- and C-terminal amino acids possess side chain functional groups. Side chain protecting groups o and p are protecting groups that can be removed by a treatment such as catalytic transfer hydrogenation using ammonium formate as the hydrogen donor (Anantharamaiah and Sivanandaiah (1977) *Chem Soc. Perkin Trans.* 490: 1–5; and Babiker et al. (1978) *J. Org. Chem.* 44: 3442–3444) under the (neutral) conditions in which side chain protecting groups m and p and α-amino and α-carboxyl protecting groups are stable. HOBT-HBTU represents condensing reagents under which minimum reacimization is observed.

To the activated amino acid X-A(m) in presence of 1-hydroxybenzotriazole-2(H-Benzotriazole-1-yl)- 1,1,3,3-tetramethylammonium hexafluorophosphate (HOBT-HBTU) and a small amount of tertiary amine such as diisopropylethylamine (DIEA) in DMF is added 2 equivalents of DIEA salt of $H_2N$—B(n)—$COO^{31}$ and stirred overnight at room temperature. The reaction is allowed to go to completion with respect to activated carboxylic acid using excess of amino acid in which α-amino is free and carboxyl is temporarily protected as DIEA salt. The reaction mixture is acidified using aqueous citric acid (10%) and extracted with ethyl acetate. In this process the free amino acid remains in citric acid. After washing ethyl acetate with water, the N-terminal protected dipeptide free acid is extracted with 5% sodium bicarbonate solution and acidified. The dipeptide free acid was extracted with ethyl acetate, the organic layer is dried ($Na_2SO_4$) and solvent evaporated to obtain the dipeptide free acid. The tripeptide is also obtained in a similar manner by reacting the dipeptide free acid with the suitably protected amino acid in which the α-amino is free and the carboxyl is temporarily protected as a DIEA salt. To obtain the tetrapeptide, the suitably carboxyl protected amino acid was condensed using HOBT-HBTU. Since the final tetrapeptide is a protected peptide, the reaction mixture after the condensation was taken in ethyl acetate and washed extensively with both aqueous bicarbonate (5%) and citric acid(5%) and then with water. These washings will remove excess of free acid and free base and the condensing reagents. The protected peptide is then reprecipitated using ethyl acetate (or ether) and petroleum ether. The protected free peptide is then subjected to catalytic transfer hydrogenation in presence of freshly prepared palladium black (Pd black) using ammonium formate as the hydrogen donor. This reaction can be carried out in almost neutral condition thus not affecting the acid sensitive side chain protecting groups. This process will remove the protecting groups on amino acids B and C. An example of this procedure is given below using the synthesis of SEQ ID NO:256.

It is noted that this reaction scheme is intended to be illustrative and not limiting. Using the teachings provided herein, other suitable reactions schemes will be known to those of skill in the art.

D) Protecting Groups.

In certain embodiments, the one or more R-groups on the constituent amino acids and/or the terminal amino acids are blocked with a protecting group, most preferably a hydrophobic protecting group. Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain embodiments, the blocking groups can additionally act as a detectable label (e.g. N-methyl anthranilyl).

In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 3 to about 20, preferably from about 3 to about 16, more preferably from about 3 to about 13, and most preferably from about 3 to about 10.

Other protecting groups include, but are not limited to N-methyl anthranilyl, Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis*, 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

XI. Enhancing Peptide Uptake/oral Availability.

A) Use of D-amino Acids.

It was also a surprising discovery of this invention that when an all L amino acid peptide (e.g. otherwise having the sequence of the peptides of this invention) is administered in conjunction with the D-form (i.e. a peptide of this invention) the uptake of the D-form peptide is increased. Thus, in certain embodiments, this invention contemplates the use of combinations of D-form and L-form peptides in the methods of this invention. The D-form peptide and the L-form peptide can have different amino acid sequences, however, in preferred embodiments, they both have amino acid sequences of peptides described herein, and in still more preferred embodiments, they have the same amino acid sequence.

It was also a discovery of this invention that concatamers of the class A amphipathic helix peptides of this invention are also effective in mitigating one or more symptoms of atherosclerosis. The monomers comprising the concatamers can be coupled directly together or joined by a linker. In certain embodiments, the linker is an amino acid linker (e.g. a proline), or a peptide linker (e.g. $Gly_4Ser_3$) (SEQ ID NO:448). In certain embodiments, the concatamer is a 2 mer, more preferably a 3 mer, still more preferably a 4 mer, and most preferably 5 mer, 8 mer, 10 mer, or 15 mer.

B) Alternating D- and L-amino Acids.

It was discovered that alternating the sterioisoforms of the amino acids at the center of the peptide will allow hydration of the particle and will better allow the peptide particles to trap pro-inflammatory oxidized lipids such as fatty acid hydroperoxides and phospholipids that contain an oxidation product of arachidonic acid at the sn-2 position.

Thus, in certain embodiments, the peptides described herein can be synthesized to comprise from 4 amino acids to 10–15 amino acids, preferentially (but not necessarily) with the center (non-terminal) amino acids being alternating D and L sterioisomers of the amino acids. The terminal amino acids can be hydrophobic either because of a hydrophobic side chain or because the amino acids bear hydrophobic blocking groups as described herein (e.g., an N-terminus is blocked with Boc-, Fmoc-, Nicotinyl-, and the like and the C-terminus blocked with (tBu)-OtBu and the like.

Examples of such peptides are illustrated in Table 9.

TABLE 9

Certain examples of peptides containign alternating D- and L-residues in the central region.

| Sequence | SEQ ID NO |
|---|---|
| Boc-Lys(εBoc)-D-Arg-L-Asp-Ser(tBu)-OtBu | 449 |
| Boc-Lys(εBoc)-L-Arg-D-Asp-Ser(tBu)-OtBu/ | 450 |

It is noted that while specific amino acid sequences are illustrated in Table 9, alternating D- and L-amino acids can be used in any of the peptides described herein.

C) Biotin-derivatized Peptides.

In certain embodiments, any of the peptides described herein can be attached (covalently coupled directly or indirectly through a linker) to one or more biotins. The biotin interacts with the intestinal sodium-dependent multivitamin transporter and thereby facilitates uptake and bioavailability of orally administered peptides.

The biotin can be directly coupled or coupled through a linker or through a side chain of an amino acid by any of a number of convenient means known to those of skill in the art. In certain embodiments, the biotin is attached to the amino groups of lysine.

A number of biotin-coupled peptides are illustrated in Table 10.

TABLE 10

Examples of certain preferred peptides:

| Sequence | SEQ ID NO |
|---|---|
| Ac-Asp-Trp-Phe-Lys(ε-biotin)-Ala-Phe-Tyr-Asp-Lys(ε-biotin)-Val-Ala-Glu-Lys(ε-biotin)-Phe-Lys(ε-biotin)-Glu-Ala-Phe-NH₂ | 451 |
| Ac-Asp-Trp-Phe-Lys(ε-biotin)-Ala-Phe-Tyr-Asp-Lys(ε-biotin)-Val-Ala-Glu-Lys(ε-biotin)-Phe-Lys-Glu-Ala-Phe-NH₂ | 452 |

TABLE 10-continued

Examples of certain preferred peptides:

| Sequence | SEQ ID NO |
|---|---|
| Ac-Asp-Trp-Phe-Lys-Ala-Phe-Tyr-Asp-Lys(E-biotin)-Val-Ala-Glu-Lys(ε-biotin)-Phe-Lys(ε-biotin)-Glu-Ala-Phe-NH$_2$ | 453 |
| Ac-Asp-Trp-Phe-Lys(ε-biotin)-Ala-Phe-Tyr-Asp-Lys-Val-Ala-Glu-Lys(ε-biotin)-Phe-Lys(ε-biotin)-Glu-Ala-Phe-NH$_2$ | 454 |
| Ac-Asp-Trp-Phe-Lys(ε-biotin)-Ala-Phe-Tyr-Asp-Lys(ε-biotin)-Val-Ala-Glu-Lys-Phe-Lys(ε-biotin)-Glu-Ala-Phe-NH$_2$ | 455 |
| Ac-Asp-Trp-Phe-Lys(ε-biotin)-Ala-Phe-Tyr-Asp-Lys-Val-Ala-Glu-Lys-Phe-Lys(ε-biotin)-Glu-Ala-Phe-NH$_2$ | 456 |
| Ac-Asp-Trp-Phe-Lys(ε-biotin)-Ala-Phe-Tyr-Asp-Lys(ε-biotin)-Val-Ala-Glu-Lys-Phe-Lys-Glu-Ala-Phe-NH$_2$ | 457 |
| Ac-Asp-Trp-Phe-Lys-Ala-Phe-Tyr-Asp-Lys-Val-Ala-Glu-Lys(ε-biotin)-Phe-Lys(ε-biotin)-Glu-Ala-Phe-NH$_2$ | 458 |
| Ac-Asp-Trp-Phe-Lys-Ala-Phe-Tyr-Asp-Lys(ε-biotin)-Val-Ala-Glu-Lys-Phe-Lys(ε-biotin)-Glu-Ala-Phe-NH$_2$ | 459 |
| Ac-Asp-Trp-Phe-Lys-Ala-Phe-Tyr-Asp-Lys(ε-biotin)-Val-Ala-Glu-Lys(ε-biotin)-Phe-Lys-Glu-Ala-Phe-NH$_2$ | 460 |
| Ac-Asp-Trp-Phe-Lys(ε-biotin)-Ala-Phe-Tyr-Asp-Lys-Val-Ala-Glu-Lys(ε-biotin)-Phe-Lys-Glu-Ala-Phe-NH$_2$ | 461 |
| Ac-Asp-Trp-Phe-Lys(ε-biotin)-Ala-Phe-Tyr-Asp-Lys-Val-Ala-Glu-Lys-Phe-Lys-Glu-Ala-Phe-NH$_2$ | 462 |
| Ac-Asp-Trp-Phe-Lys-Ala-Phe-Tyr-Asp-Lys(ε-biotin)-Val-Ala-Glu-Lys-Phe-Lys-Glu-Ala-Phe-NH$_2$ | 463 |
| Ac-Asp-Trp-Phe-Lys-Ala-Phe-Tyr-Asp-Lys-Val-Ala-Glu-Lys(ε-biotin)-Phe-Lys-Glu-Ala-Phe-NH$_2$ | 464 |
| Ac-Asp-Trp-Phe-Lys-Ala-Phe-Tyr-Asp-Lys-Val-Ala-Glu-Lys-Phe-Lys(ε-biotin)-Glu-Ala-Phe-NH$_2$ | 465 |

XII. Pharmaceutical Formulations.

In order to carry out the methods of the invention, one or more peptides or peptide mimetics of this invention are administered, e.g. to an individual diagnosed as having one or more symptoms of atherosclerosis, or as being at risk for atherosclerosis. The peptides or peptide mimetics can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the peptides or mimetics are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups, that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The peptides or mimetics identified herein are useful for parenteral, topical, oral, nasal (or otherwise inhaled), rectal, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The peptides and/or peptide mimetics of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of peptide or mimetic can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. It will be appreciated that such dosages may be varied to optimize a therapeutic regimen in a particular subject or group of subjects.

In certain preferred embodiments, the peptides or peptide mimetics of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations, that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

A) Sustained Release Formulations.

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

B) Combined Formulations.

In certain instances, one or more peptides of this invention are administered in conjunction with one or more active agents (e.g. statins, beta blockers, ACE inhibitors, lipids, etc.). The two agents (e.g. peptide and statin) can be administered simultaneously or sequentially. When administered sequentially the two agents are administered so that both achieve a physiologically relevant concentration over a similar time period (e.g. so that both agents are active at some common time).

In certain embodiments, both agents are administered simultaneously. In such instances it can be convenient to provide both agents in a single combined formulation. This can be achieved by a variety of methods well known to those of skill in the art. For example, in a tablet formulation the tablet can comprise two layers one layer comprising, e.g. the statin(s), and the other layer comprising e.g. the peptide(s). In a time release capsule, the capsule can comprise two time release bead sets, one for the peptide(s) and one containing the statin(s).

The foregoing formulations and administration methods are intended to be illustrative and not limiting. It will be appreciated that, using the teaching provided herein, other suitable formulations and modes of administration can be readily devised.

XIII. Additional Pharmacologically Active Agents.

Additional pharmacologically active agents may be delivered along with the primary active agents, e.g., the peptides of this invention. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

A) Statins.

It was a surprising discovery that administration of one or more peptides of this invention "concurrently" with one or more statins synergistically enhances the effect of the statin(s). That is, the statins can achieve a similar efficacy at lower dosage thereby obviating potential adverse side effects (e.g. muscle wasting) associated with these drugs and/or cause the statins to be significantly more anti-inflammatory at any given dose.

The major effect of the statins is to lower LDL-cholesterol levels, and they lower LDL-cholesterol more than many other types of drugs. Statins generally inhibit an enzyme, HMG-CoA reductase, which controls the rate of cholesterol production in the body. These drugs typically lower cholesterol by slowing down the production of cholesterol and by increasing the liver's ability to remove the LDL-cholesterol already in the blood.

The large reductions in total and LDL-cholesterol produced by these drugs appears to result in large reductions in heart attacks and heart disease deaths. Thanks to their track record in these studies and their ability to lower LDL-cholesterol, statins have become the drugs most often prescribed when a person needs a cholesterol-lowering medicine. Studies using statins have reported 20 to 60 percent lower LDL-cholesterol levels in patients on these drugs. Statins also reduce elevated triglyceride levels and produce a modest increase in HDL-cholesterol. Recently it has been appreciated that statins have anti-inflammatory properties that may not be directly related to the degree of lipid lowering achieved. For example it has been found that statins decrease the plasma levels of the inflammatory marker CRP relatively independent of changes in plasma lipid levels. This anti-inflammatory activity of statins has been found to be as or more important in predicting the reduction in clinical events induced by statins than is the degree of LDL lowering.

The statins are usually given in a single dose at the evening meal or at bedtime. These medications are often given in the evening to take advantage of the fact that the body makes more cholesterol at night than during the day. When combined with the peptides described herein, the combined peptide/statin treatment regimen will also typically be given in the evening.

Suitable statins are well known to those of skill in the art. Such statins include, but are not limited to atorvastatin (Lipitor®, Pfizer), simvastatin (Zocor®, Merck0, pravastatin (Pravachol®, Bristol-Myers Squibb®, fluvastatin (Lescol®, Novartis), lovastatin (Mevacor®, Merck), rosuvastatin (Crestor®, Astra Zeneca), and Pitavastatin (Sankyo), and the like.

The combined statin/peptide dosage can be routinely optimized for each patient. Typically statins show results after several weeks, with a maximum effect in 4 to 6 weeks. Prior to combined treatment with a statin and one of the peptides described herein, the physician would obtain routine tests for starting a statin including LDL-cholesterol and HDL-cholesterol levels. Additionally, the physician would also measure the anti-inflammatory properties of the patient's HDL and determine CRP levels with a high sensitivity assay. After about 4 to 6 weeks of combined treatment, the physician would typically repeat these tests and adjust the dosage of the medications to achieve maximum lipid lowering and maximum anti-inflammatory activity.

B) Cholesterol Absorption Inhibitors.

In certain embodiments, one or more peptides of this invention are administered to a subject in conjunction with one or more cholesterol absorption inhibitors. The peptide(s) can be administered before, after, or simultaneously with the cholesterol absorption inhibitor. In the latter case, the cholesterol absorption inhibitor can be provided as a separate formulation or as a combined formulation with one or more of the peptide(s).

Cholesterol absorption inhibitors are well known to those of skill in the art. One important cholesterol absorption inhibitor is Ezetimibe, also known as 1-(4-fluorophenyl)-3 (R)-[3-(4-fluorophenyl)-3(S)-hydroxypropyl]-4(S)-(4-hydroxyphenyl)-2-azetidinone (available from Merck). Ezetimibe reduces blood cholesterol by inhibiting the absorption of cholesterol by the small intestine.

C) Beta Blocers.

Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), carvedilol, (Coreg™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

D) ACE Inhibitors.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

E) Lipid-based Formulations.

In certain embodiments, the peptides of this invention are administered in conjunction with one or more lipids. The lipids can be formulated as an active agent, and/or as an excipient to protect and/or enhance transport/uptake of the peptides or they can be administered separately.

Without being bound by a particular theory, it was discovered of this invention that administration (e.g. oral administration) of certain phospholipids can significantly increase HDULDL ratios. In addition, it is believed that certain medium-length phospholipids are transported by a process different than that involved in general lipid transport. Thus, co-administration of certain medium-length phospholipids with the peptides of this invention confer a number of advantages: They protect the phospholipids from digestion or hydrolysis, they improve peptide uptake, and they improve HDL/LDL ratios.

The lipids can be formed into liposomes that encapsulate the polypeptides of this invention and/or they can be simply complexed/admixed with the polypeptides. Methods of making liposomes and encapsulating reagents are well known to those of skill in the art (see, e.g., Martin and Papahadjopoulos (1982) *J. Biol. Chem.,* 257: 286–288; Papahadjopoulos et al. (1991) *Proc. Natl. Acad. Sci. USA,* 88: 11460–11464; Huang et al. (1992) *Cancer Res.,* 52:6774–6781; Lasic et al. (1992) *FEBS Lett.,* 312: 255–258., and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 11.

TABLE 11

Preferred fatty acids in the sn-1 and/or sn-2 position of the preferred phospholipids for administration of D polypeptides.

| Carbon No. | Common Name | IUPAC Name |
|---|---|---|
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |
| 22:0 | Behenoyl | Docosanoic |
| 23:0 | Trucisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

XIV. Kits.

In another embodiment this invention provides kits for amelioration of one or more symptoms of atherosclerosis and/or for the prophylactic treatment of a subject (human or animal) at risk for atherosclerosis and/or for stimulating the formation and cycling of pre-beta high density lipoprotein-like particles and/or for inhibiting one or more symptoms of osteoporosis. The kits preferably comprise a container containing one or more of the peptides or peptide mimetics of this invention. The peptide or peptide mimetic can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In certain preferred embodiments, the kits additionally include a statin (e.g. cerivastatin, atorvastatin, simvastatin, pravastatin, fluvastatin, lovastatin. rosuvastatin, pitavastatin, etc.) either formulated separately or in a combined formulation with the peptide(s). Typically the dosage of a statin in such a formulation can be lower than the dosage of a statin typically presecribed without the synergistic peptide.

In addition, the kits optionally include labeling and/or instructional materials providing directions (i.e., protocols) for the practice of the methods or use of the "therapeutics" or "prophylactics" of this invention. Preferred instructional materials describe the use of one or more polypeptides of this invention to mitigate one or more symptoms of atherosclerosis and/or to prevent the onset or increase of one or more of such symptoms in an individual at risk for atherosclerosis and/or to stimulate the formation and cycling of pre-beta high density lipoprotein-like particles and/or to inhibit one or more symptoms of osteoporosis. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Evaluation of Small Peptides to Mediate Symptoms of Atherosclerosis and other Inflammatory Pathologies The apo A-I mimetic peptides described herein (see, e.g., Table 1) exhibit antiatherogenic properties similar to apo A-I in that they remove the "seeding molecules" (e.g., oxidized phospholipids such as Ox-PAPC, POVPC, PGPC, and PEIPC, etc.) necessary for artery wall cells to oxidized LDL and are similar to apo A-I in that they ameliorated atherosclerosis in mouse models.

The apo A-I mimetic peptides (e.g. D-4F, SEQ ID NO:8), differ from apo A-I in that they are also active in a co-incubation similar to apo J (see, e.g., U.S. Ser. No. 10/120, 508 and PCT/US03/09988). These peptides generally do not have substantial sequence homology to apo A-I, but have homology in their helical structure and in their ability to bind lipids.

Figure 3:
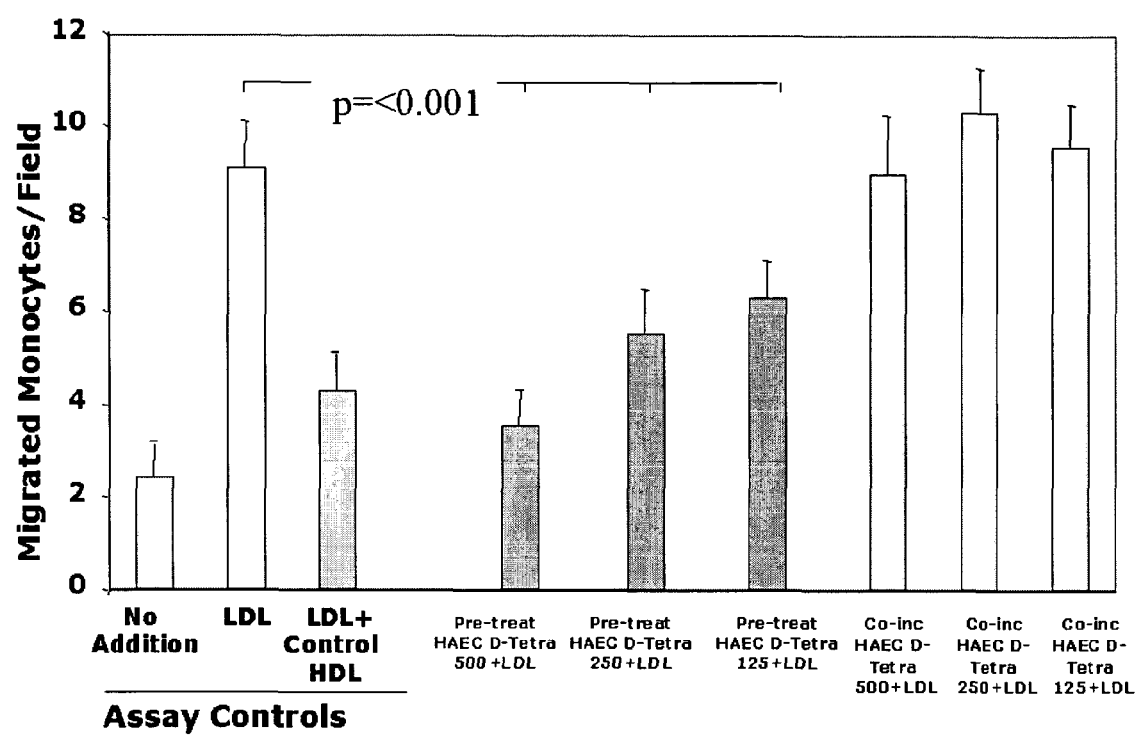
FIG. 3 shows that pre-incubation (pre-treatment) but not co-incubation (Co-inc) of Boc-Lys(Boc)-Arg-Asp-Ser(tBu)-OtBu (synthesized from all D-amino acids) (SEQ ID NO:238 in Table 4) inhibited LDL-induced monocyte chemotactic activity produced by human artery wall cells (HAEC). The cells were either pre-incubated with 125 μg/ml, 250 μg/nm, or 500 μg/ml of the peptide, the peptide was then removed and LDL at 100 μg/ml cholesterol with fresh medium was added or the same concentrations of peptide were added together with the LDL and monocyte chemotactic activity determined.
Figure 4:
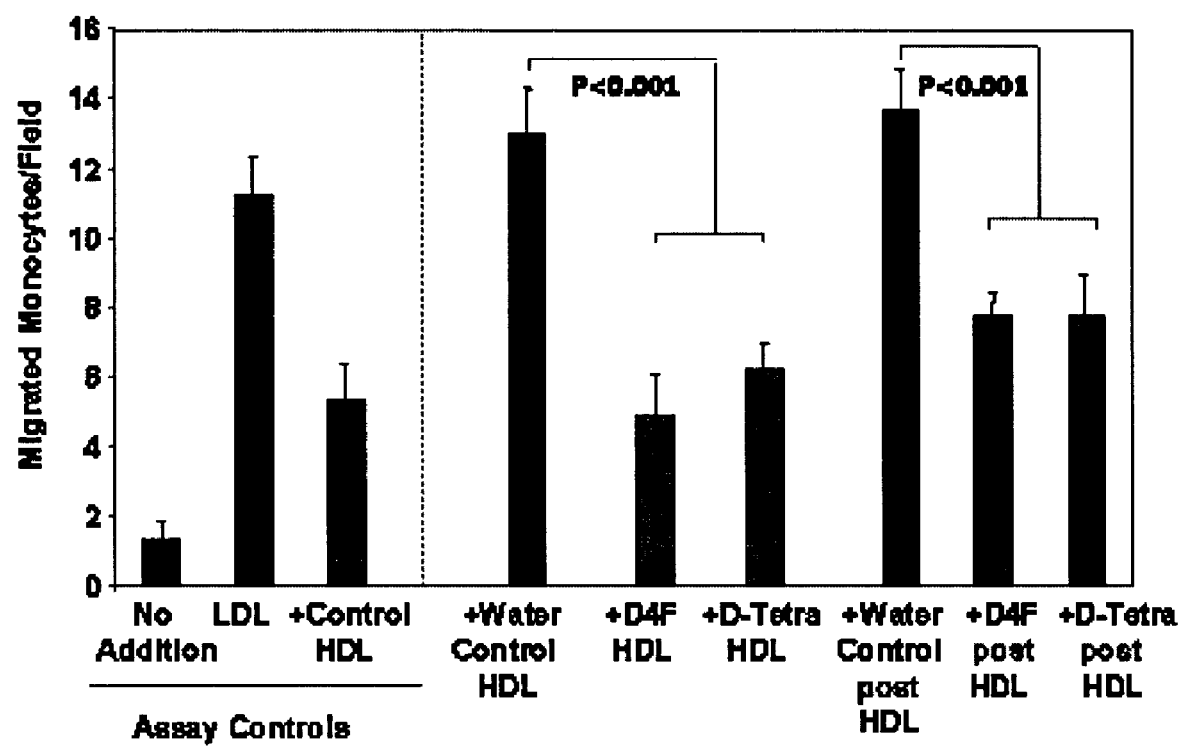
FIG. 4 shows that the addition of the tetrapeptide described in FIG. 3 to the drinking water of apoE null mice converted HDL and the post-HDL FPLC fractions from pro-inflammatory to anti-inflammatory similar to D-4F. The tetrapeptide or D-4F were added to the drinking water of the mice (n=4 for each condition) at a concentration of 5 μg/ml for 18 hours. The mice were bled and their lipoproteins were separated by FPLC. A control human LDL at 100 μg/ml of Cholesterol was added (LDL) or not added (No Addition) to human artery wall cocultures or was added together with HDL at 50 μg/ml from a normal human control subject (+Control HDL) or HDL at 50 μg/ml from apoE null mice that received drinking water without peptide (+Water Control HDL) or received the tetrapeptide (+D-Tetra HDL) or D-4F (+D4F HDL) or the post-HDL FPLC fractions from apoE null mice that did not receive the peptide (+Water Control post HDL) or from mice that did receive the tetrapeptide (+D-Tetra post HDL) or received D-4F (+D4F post HDL)were added at 20 μg/ml together with the control human LDL at 100 μg/ml of Cholesterol. After 8 hours the supernatants were assayed for monocyte chemotactic activity.

The smaller peptides described herein (see, e.g., Tables 4–7 herein) are similar to native apoA-I in that they prevent LDL oxidation and LDL-induced monocyte chemotactic activity in a pre-incubation with artery wall cells but not in a co-incubation (see, e.g., FIG. 3).

The peptide described in FIG. 3 was also active in vivo (FIG. 4). The tetrapeptide or D-4F (SEQ ID NO:8) were added at 5 µg/ml to the drinking water or not added to the drinking water of apoE null mice (a mouse model of human atherosclerosis). After 18 hours the mice were bled and their lipoproteins isolated by FPLC. Adding the fractions containing mature HDL or the FPLC fractions after these fractions where pre-beta HDL would be expected (particles that come off the FPLC column just after the main HDL peak; post HDL) from mice that received drinking water without peptide increased the monocyte chemotactic activity induced by a control LDL added to a human artery wall cell coculture (FIG. 4). In contrast, adding HDL or the post HDL FPLC fractions from the mice that received the tetrapeptide or D-4F in their drinking water significantly decreased the LDL-induced monocyte chemotactic activity indicating that the tetrapeptide and D-4F converted these lipoproteins from a pro-inflammatory to an anti-inflammatory state (FIG. 4).

As shown in FIG. 5, LDL taken from the mice that received the tetrapeptide or D-4F induced significantly less monocyte chemotactic activity than did LDL from mice that did not receive the peptides confirming the biologic activity of the orally administered D-tetrapeptide.

Figure 6:
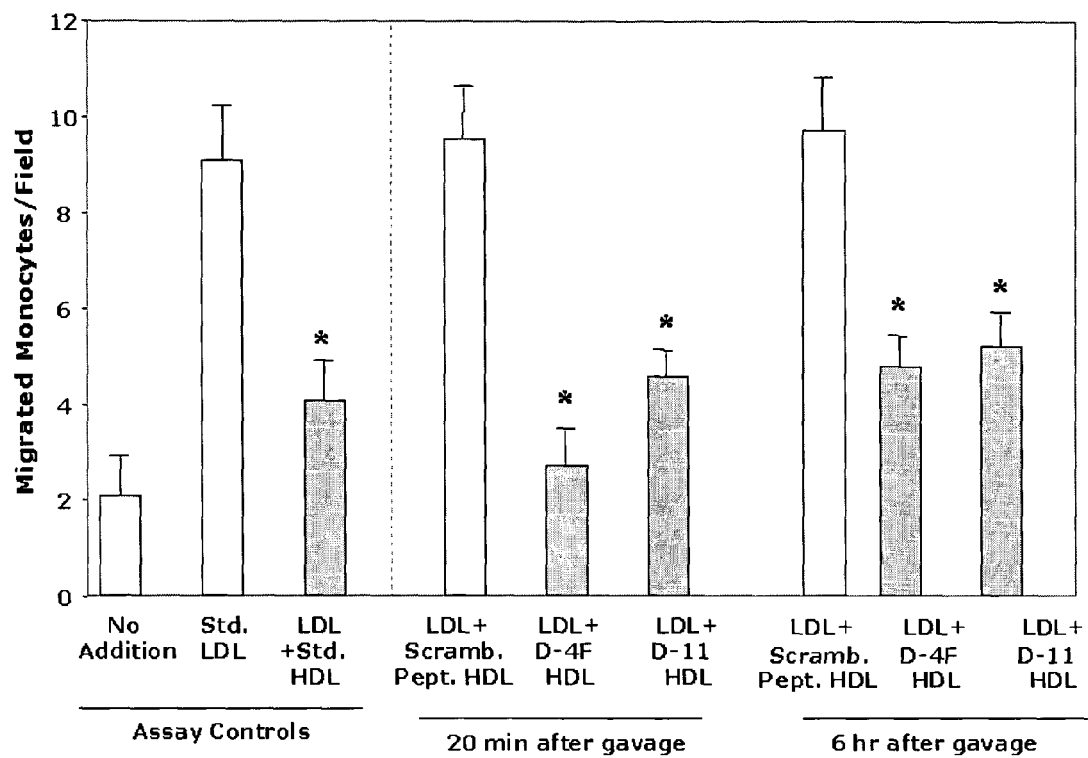
FIG. 6 shows that SEQ ID NO:258 from Table 4 (designated D-11 in the figure) when synthesized from all D-amino acids or D-4F given orally renders HDL anti-inflammatory in apoE null mice but a peptide containing the same D-amino acids as in D-4F but arranged in a scrambled sequence that prevents lipid binding did not. Five hundred micrograms of SEQ ID NO: 258 synthesized from D-amino acids (D-11) or 500 μg of D-4F (D-4F) or 500 μg of scrambled D-4F (Scramb. Pept.) were instilled via a tube into the stomachs of female, 3 month old apoE null mice, (n=4) and the mice were bled 20 min (20 min after gavage) or 6 hours later (6 hr after gavage). Plasma was separated and HDL was isolated by FPLC. Cultures of human aortic endothelial cells received medium alone (No Addition/Assay Controls), standard normal human LDL at 100 μgm/mL cholesterol without (LDL/Assay Controls) or together with standard control human HDL (LDL+Control HDL/Assay Controls) at 50 μgm/mL cholesterol, or control human LDL at 100 μgm/mL cholesterol was added with mouse HDL at 50 μgm/mL cholesterol obtained from mice that received the scrambled D-4F peptide (LDL+Scramb.Pept. HDL), or D-4F (LDL+D-4F HDL) or SEQ ID NO: 258 made from all D-amino acids (LDL+D-11 HDL). The cultures were incubated for 8 hrs. The supernatants were then assayed for monocyte chemotactic activity. The values are mean+/−SD of the number of migrated monocytes in 9 high power fields. * indicates $p<0.001$.

FIG. 6 demonstrates that HDL taken 20 min or 6 hours after SEQ ID NO:258 from Table 4 synthesized from D-amino acids was instilled into the stomachs of apoE null mice by stomach tube, was converted from pro-inflammatory to anti-inflammatory and was similar to that from mice that received D-4F and quite different from mice that received a peptide with the same D-amino acids as in D-4F but arranged in such a way as to prevent the formation of a class A amphipathic helix and hence rendering the peptide unable to bind lipids (scrambled D-4F).

Figure 7:
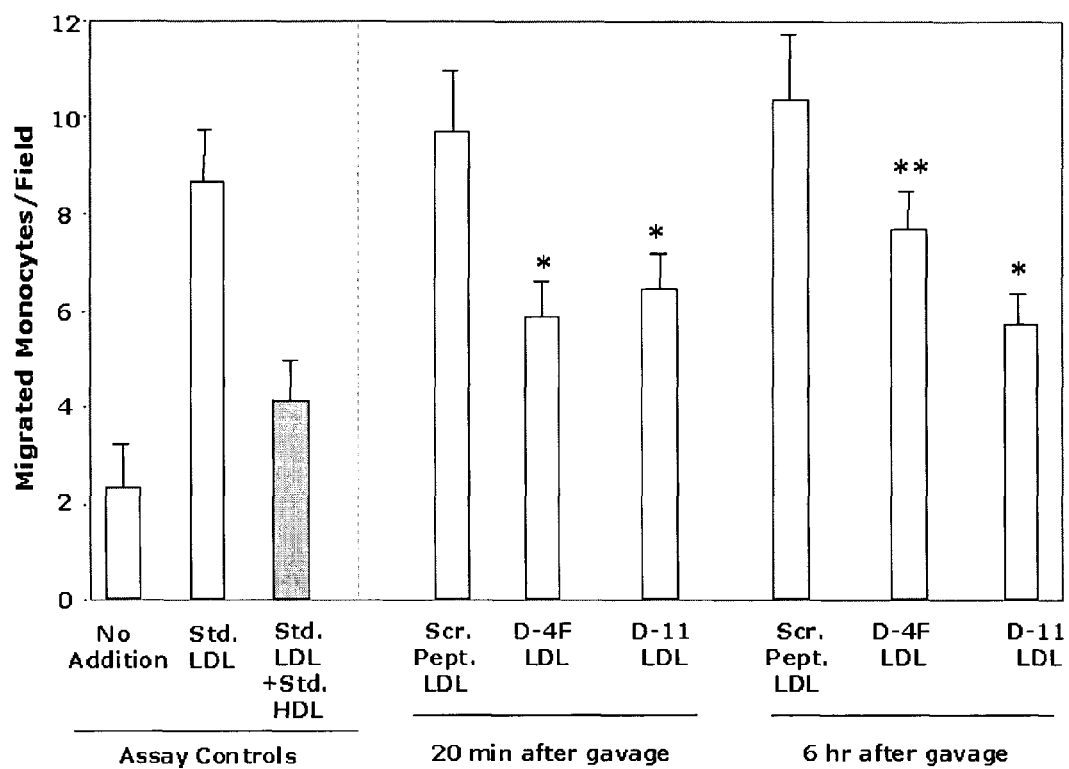
FIG. 7 shows that apoE null mice receiving D-4F or SEQ ID NO:258 from Table 4 synthesized from D-amino acids (designated D-11) (but not from mice that received scrambled D-4F) have LDL that induces less monocyte chemotactic activity. The LDL from the FPLC fractions of the mice described in FIG. 6 was added to the cultures at 100 μg/ml. After 8 hours the supernatants were assayed for monocyte chemotactic activity.* indicates $p<0.001$, **indicates $p<0.01$.

FIG. 7 demonstrates that at both 20 min and 6 hours after oral administration of D-4F or SEQ ID NO:258 synthesized from D-amino acids the mouse LDL was significantly less able to induce monocyte chemotactic activity compared to LDL taken from mice that received the scrambled D-4F peptide.

Figure 8:
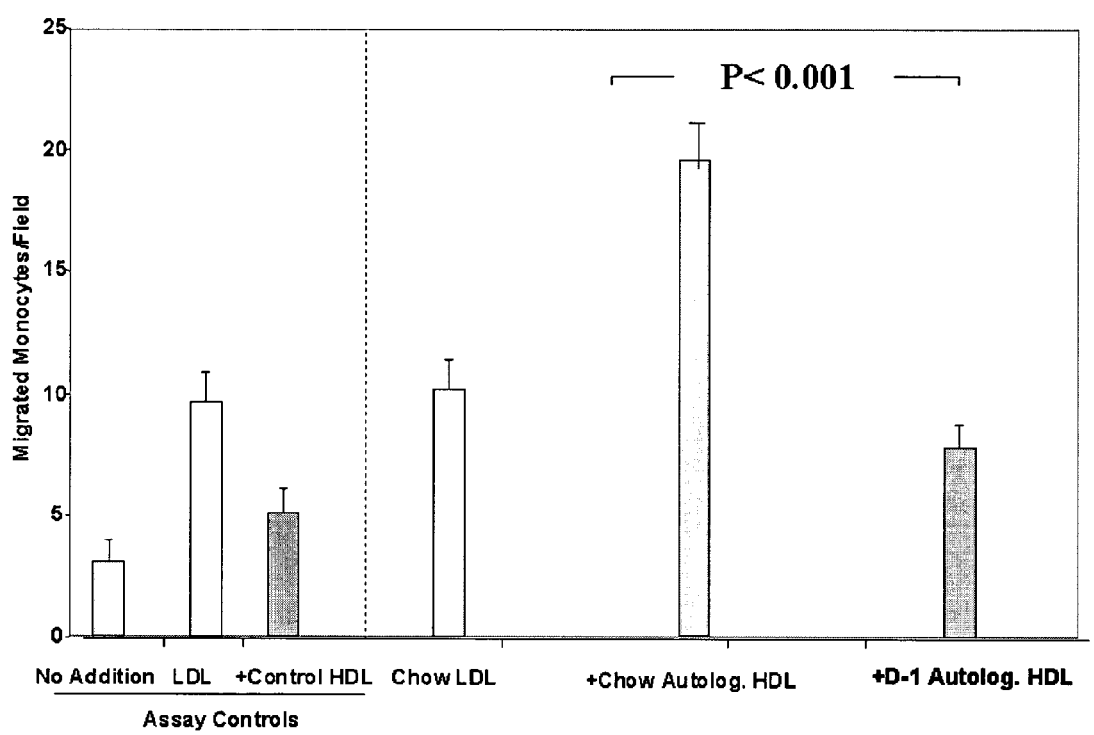
FIG. 8 shows that HDL was converted from pro-inflammatory to anti-inflammatory after addition of SEQ ID NO:238 in Table 4 synthesized from D amino aicids (designated D-1) to the chow of apoE null mice (200 μg/gm chow for 18 hours). Assay Controls: No Addition, no addition to the cocultures; LDL ,a standard control human LDL was added to the cocultures; +Control HDL, a control normal human HDL was added to the cocultures. Chow LDL, LDL from mice that received chow alone; +Chow Autolog. HDL, HDL from the mice that received Chow alone was added together with the LDL from these mice; +D-1 Autolog. HDL, HDL from the mice receiving the peptide was added together with the LDL from these mice to the cocultures and monocyte chemotactic activity was determined.

FIG. 8 demonstrates that adding SEQ ID NO:238 in Table 4 (synthesized from all D-amino acids) to the food of apoE null mice for 18 hours converted the pro-inflammatory HDL of apoE null mice to anti-inflammatory HDL.

Figure 9:
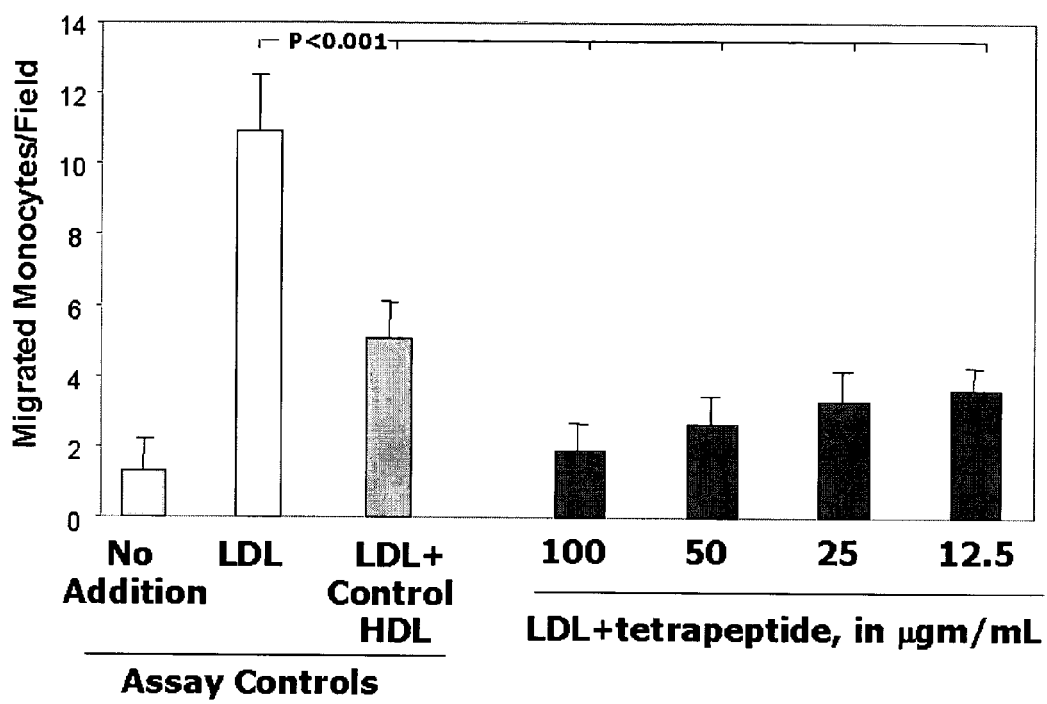
FIG. 9 shows that the tetrapeptide (SEQ ID NO:258 in Table 4) was ten times more potent than SEQ ID NO:238 in vitro. The tetrapeptide was added or not added in a pre-incubation to human artery wall cell cocultures at 100, 50, 25 or 12.5 μgm/mL and incubated for 2 hrs. The cultures were then washed. Some wells then received medium alone (No Addition). The other wells either received standard normal human LDL at 100 μgm/mL cholesterol (LDL) or received this LDL together with a standard control human HDL (LDL+Control HDL) at 50 μgm/mL cholesterol and were incubated for 8 hrs. Culture supernatants were then assayed for monocyte chemotactic activity. The values are mean+/-SD of the number of migrated monocytes in 9 high power fields. The wells that received the tetrapeptide in the 2 hr pre-incubation at the concentrations noted above followed by the addition of LDL at 100 μgm/mL cholesterol are indicated in the figure (LDL+tetrapeptide, in μgm/ml).

FIG. 9 demonstrates that in vitro SEQ ID NO:258 in Table 4 was ten times more potent than SEQ ID NO:238.

As shown in FIG. 3 SEQ ID NO:238 at 125 µg/ml was only mildly effective while as shown in FIG. 9, SEQ ID NO:258 was highly active at 12.5 µg/ml in a pre-incubation in vitro.

Figure 10:
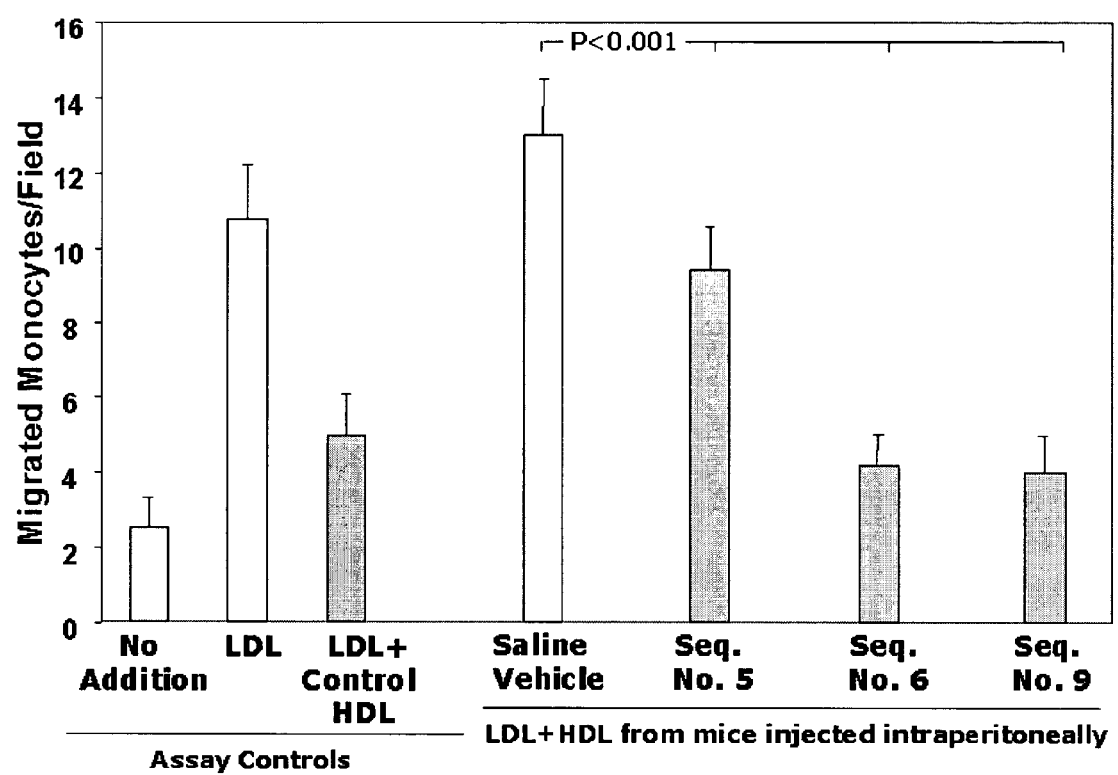
FIG. 10 shows that SEQ ID NOs:243, 242, and 256 from Table 4 (designated Seq No.5, Seq No.6, and Seq No. 9, respectively in the figure) convert pro-inflammatory HDL from apoE null mice to anti-inflammatory HDL. Two month old female apo E null mice (n=4 per treatment) fasted for 18 hrs, were injected intraperitoneally with L-tetrapeptides at 20 μgm peptide/mouse or were injected with the saline vehicle (Saline Vehicle). Two hours later, blood was collected from the retroorbital sinus under mild anesthesia with Isofluorine. Plasma was separated and HDL was isolated by FPLC. HDL inflammatory/anti-inflammatory properties were then determined. Cultures of human aortic endothelial cells received medium alone (No Addition), standard normal human LDL at 100 μgm/mL cholesterol without (LDL) or together with standard control human HDL (LDL+Control HDL) at 50 μgm/mL cholesterol, or standard control human LDL at 100 μgm/mL cholesterol with mouse HDL at 50 μgm/mL cholesterol obtained from mice that received the tetrapeptides or the saline vehicle (LDL+HDL from mice injected intraperitoneally). The cultures were incubated for 8 hrs. The supernatants were then assayed for monocyte chemotactic activity. The values are mean+/−SD of the number of migrated monocytes in 9 high power fields.

The experiments shown in FIG. 10 demonstrate that SEQ ID NO:243, SEQ ID NO: 242, and SEQ ID NO:256 from Table 4 were also able to convert the pro-inflammatory HDL of apoE null mice to anti-inflammatory HDL.

Figure 11:
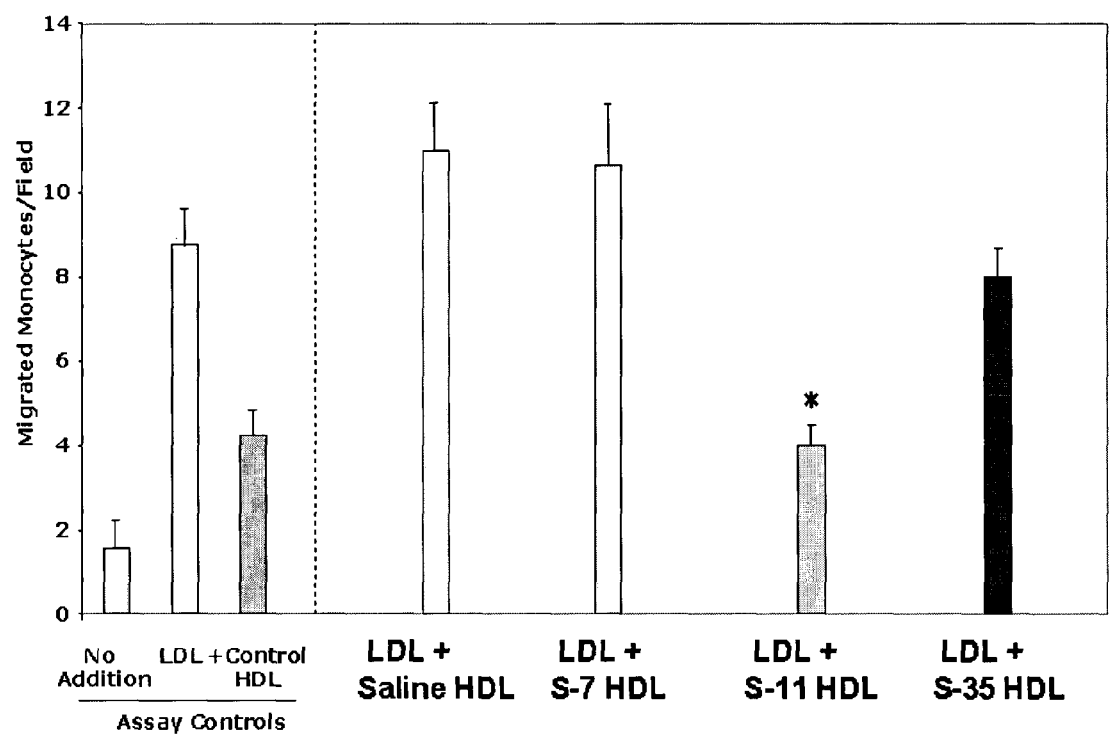
FIG. 11 shows that SEQ ID NO:258 from Table 4 (designated S-11 in the Figure) converts pro-inflammatory HDL from apoE null mice to anti-inflammatory HDL better than SEQ ID NO:254 and SEQ ID NO:282 (designated S-7 and S-35, respectively in the Figure). Two-month-old female apo E null mice (n=4 per treatment) fasted for 18 hrs, were injected intraperitoneally with S-7 or S-11 or S-35, at 20 μgm peptide/mouse or were injected with the saline vehicle (Saline Vehicle). Two hours later, blood was collected from the retroorbital sinus under mild anesthesia with Isofluorine. Plasma was separated and LDL and HDL were isolated by FPLC. HDL inflammatory/anti-inflammatory properties were then determined. Cultures of human aortic endothelial cells received medium alone (No Addition/Assay Controls), standard normal human LDL at 100 μgm/mL cholesterol without (LDL/Assay Controls) or together with standard control human HDL (+Control HDUAssay Controls) at 50 μgm/mL cholesterol, or mouse LDL at 100 μgm/mL cholesterol with mouse HDL at 50 μgm/mL cholesterol obtained from mice that received S-7, or S-11 or S-35 (LDL+S-7 HDL. LDL+S-11 HDL, LDL+S-35 HDL, respectively) or the saline vehicle (LDL+Saline HDL)). The cultures were incubated for 8 hrs. The supernatants were then assayed for monocyte chemotactic activity. The values are mean+/−SD of the number of migrated monocytes in 9 high power fields.*$p<0.001$.
Figure 12:
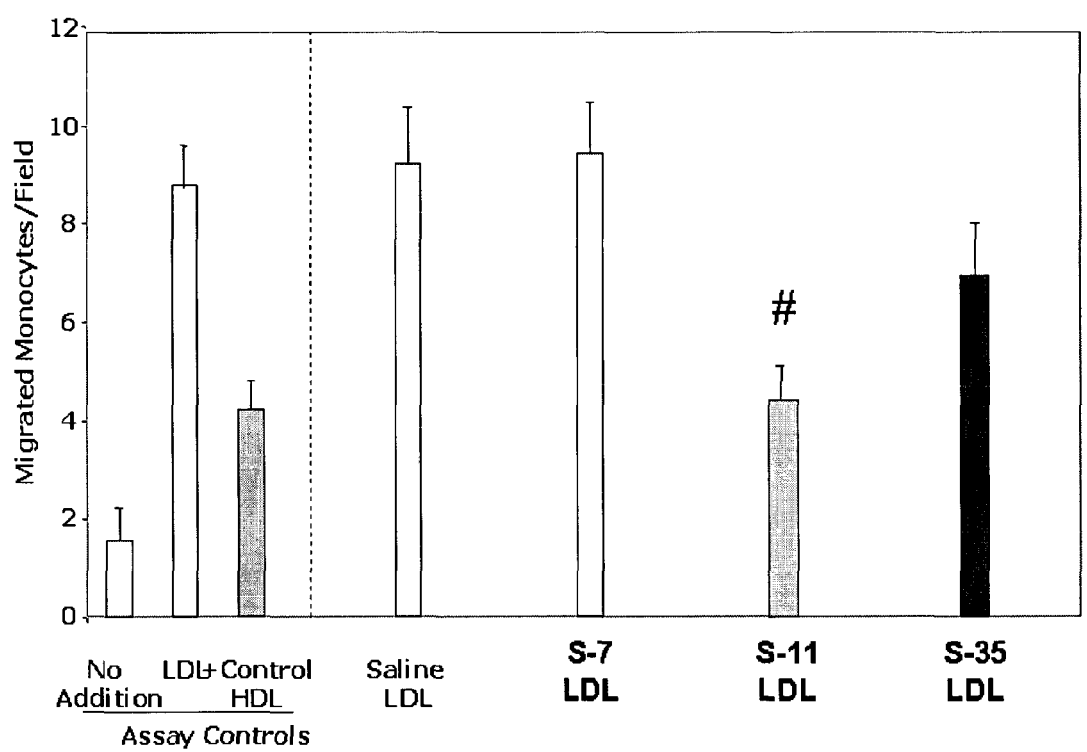
FIG. 12. The LDL from the FPLC fractions of the mice described in FIG. 11 was added to the cells at 100 μg/ml. After 8 hours the supernatants were assayed for monocyte chemotactic activity. Assay Controls are as described in FIG. 11. Saline LDL, LDL from mice injected with the saline vehicle; S-7 LDL, LDL from mice injected with SEQ ID NO:254 from Table 4 as described in FIG. 11; S-11 LDL, LDL from mice injected with SEQ ID NO:258 from Table 4 as described in FIG. 11 ;S-35, LDL from mice injected with SEQ ID NO:282 as described in FIG. 9. # $p<0.001$.
Figure 13:
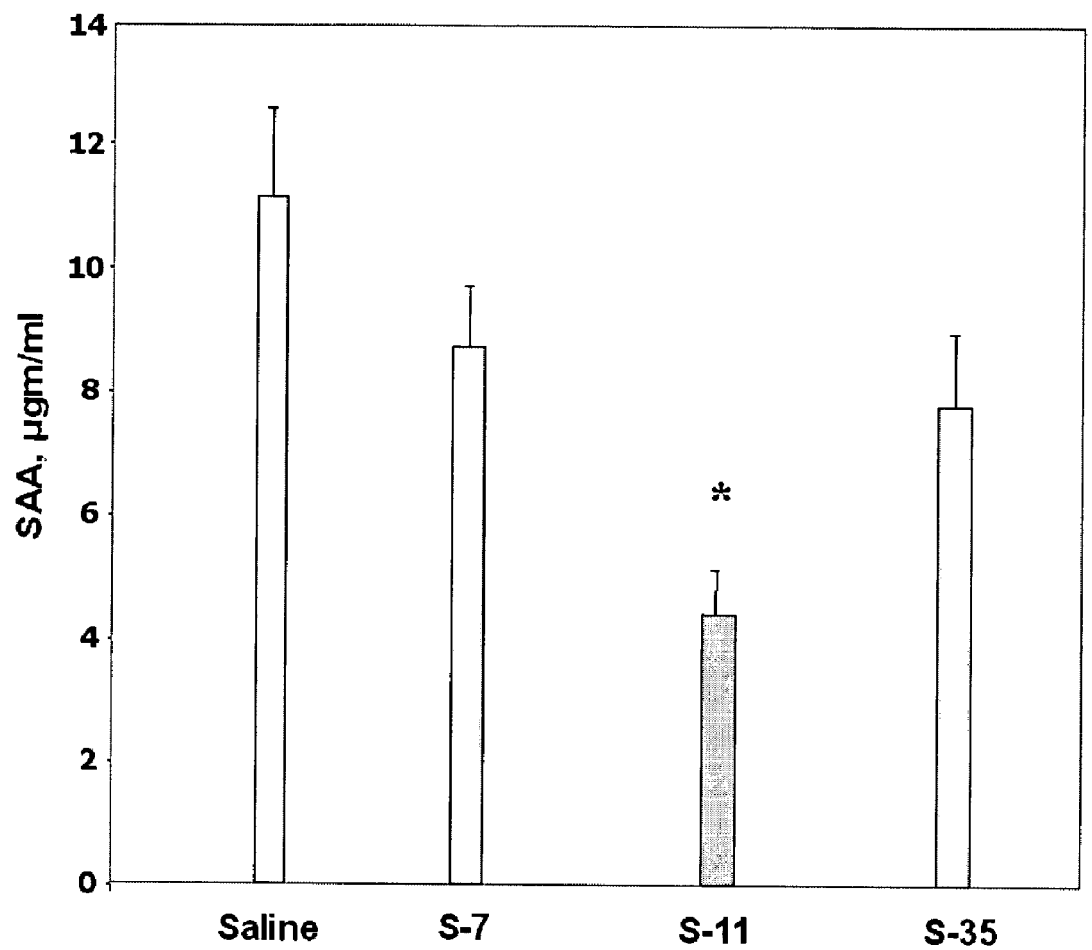
FIG. 13 shows serum Amyloid A (SAA) plasma levels after injection of peptides. SAA levels in plasma were measured 24 hours after injection of the peptides described in FIGS. 11 and 12. *$p<0.001$.

The activity of particular peptides of this invention is dependent on particular amino acid substitutions as shown in FIGS. 11, 12, and 13. SEQ ID NO:254 is identical with SEQ ID NO:258 except that the positions of the arginine and glutamic acid amino acids are reversed in the sequence (i.e. SEQ ID NO:254 is Boc-Lys(∈Boc)-Glu-Arg-Ser(tBu)-OtBu, while SEQ ID NO:258 is Boc-Lys(∈Boc)-Arg-Glu-Ser(tBu)-OtBu). As a result of this seemingly minor change, SEQ ID NO: 254 is substantially less effective in these assays than SEQ ID NO:258.

The experiments described in FIGS. 11 and 12 demonstrate that SEQ ID NO:258 from Table 4 was more effective in converting pro-inflammatory HDL to anti-inflammatory HDL and rendering LDL less able to induce monocyte chemotactic activity than was either SEQ ID NO:254 or SEQ ID NO:282.

Serum Amyloid A (SAA) is a positive acute phase reactant in mice that is similar to C-Reactive Protein (CRP) in humans. The data in FIG. 13 indicate that this acute phase reactant was significantly reduced in plasma after injection of SEQ ID NO:258 and to a lesser, non-significant degree after injection of SEQ ID NO:254 and 282.

Figure 14:
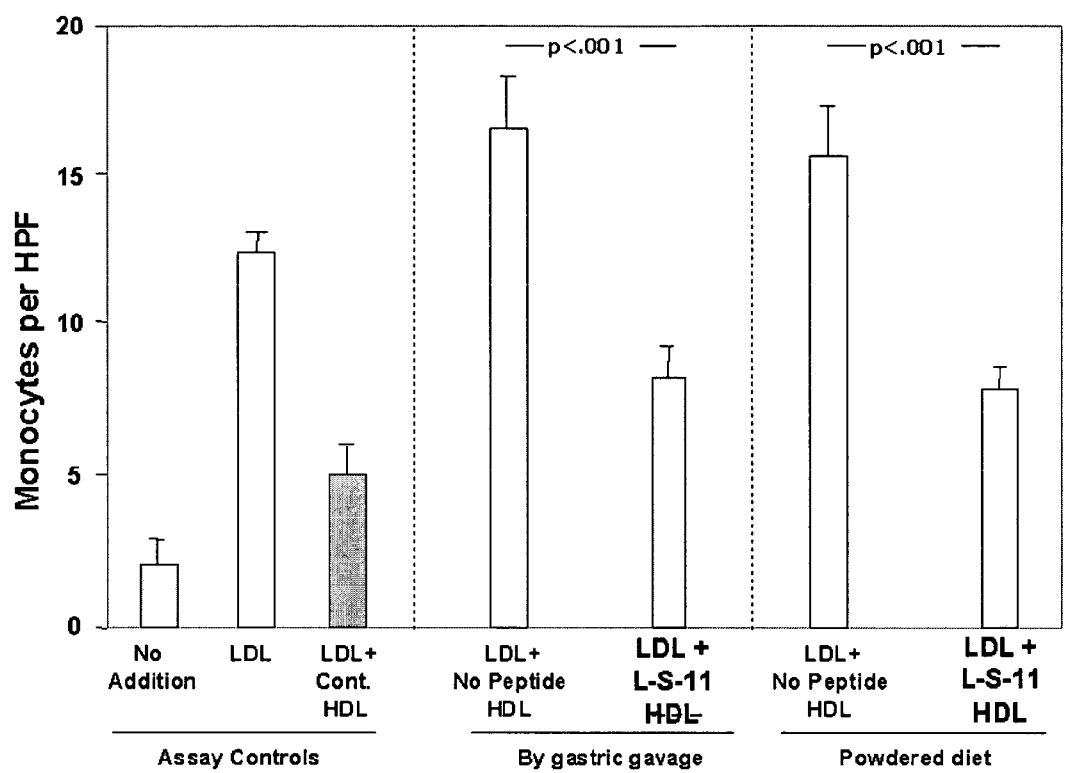
FIG. 14 shows that SEQ ID NO:258 from Table 4 when synthesized from all L-amino acids and given orally converts pro-inflammatory HDL from apoE null mice to anti-inflammatory HDL. Female, 3 month old apoE null mice, (n=4), were given 200 micrograms in water of the peptide described as SEQ ID NO:258 from Table 4, which was synthesized from all L-amino acids (designated S-11 in the figure). The peptide or water without peptide was administered by stomach tube and the mice were bled 4 hours later. A second group of four mice were given access to standard mouse chow in powdered form and containing 200 micrograms of the S-11, which was synthesized from all L-amino acids and added per 1.0 gram of powdered mouse chow in a total of 4 grams of powdered mouse chow containing a total of 800 micrograms of the peptide for the cage of four mice or they were given the same powdered mouse chow without peptide. The chow was available to the mice overnight and by morning the chow was consumed and the mice were bled. Plasma was separated and HDL was isolated by FPLC. HDL inflammatory/anti-inflammatory properties were then determined. Cultures of human aortic endothelial cells received medium alone (No Addition/Assay Controls), standard normal human LDL at 100 μgm/mL cholesterol without (LDL/Assay Controls) or together with standard control human HDL (LDL+Cont.HDL/Assay Controls) at 50 μgm/mL cholesterol, or control human LDL at 100 μgm/mL cholesterol with mouse HDL at 50 μgm/mL cholesterol obtained from mice that received no peptide (LDL+ No Peptide HDL) or L-S-11 (LDL+L-S-11 HDL) by stomach tube (By gastric gavage) or in the mouse chow (Powdered diet). The cultures were incubated for 8 hrs. The supernatants were then assayed for monocyte chemotactic activity. The values are mean+/−SD of the number of migrated monocytes in 9 high power fields. $p<0.001$.
Figure 15:
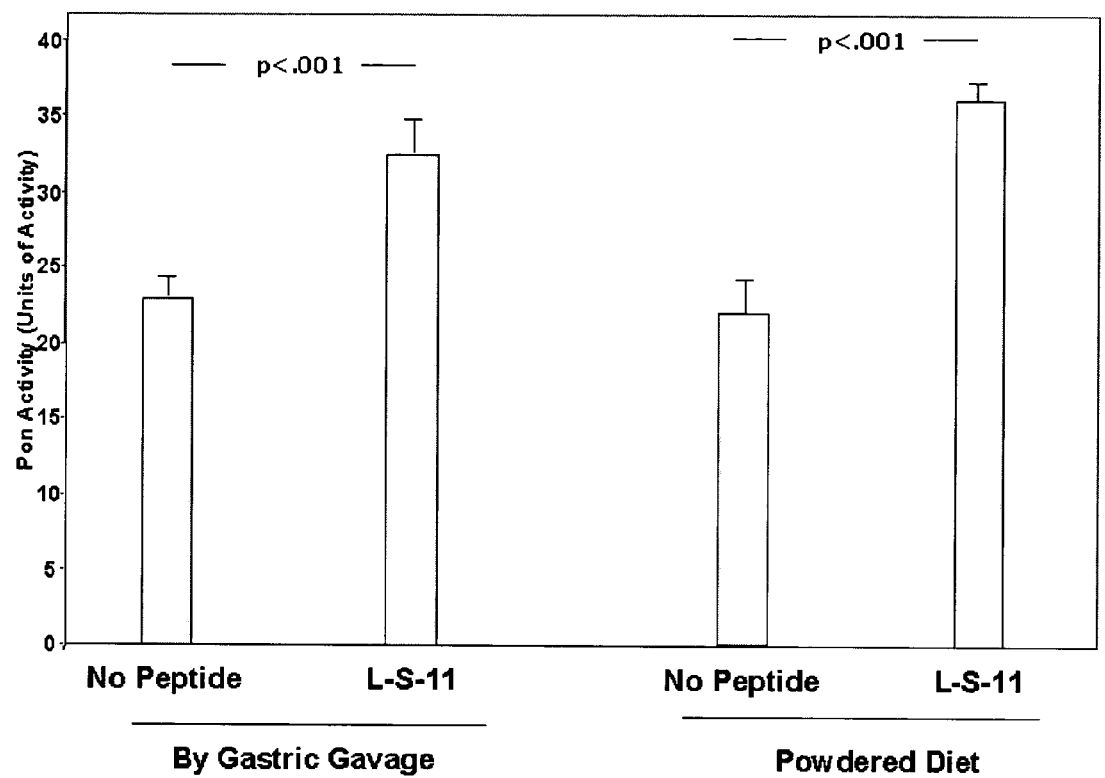
FIG. 15 L-S-11, when synthesized from all L-amino acids and given orally increased plasma paraoxonase activity. The plasma from the mice described in FIG. 14 was assayed for paraoxonase activity (PON Activity, which is shown in the figure as Units per 500 μl of plasma). No peptide, mice that received water or food alone without peptide. L-S-11, mice given 200 micrograms in water or food of the peptide described as SEQ ID NO:256 from Table 4 as described in FIG. 14. $P<0.001$.
Figure 16:
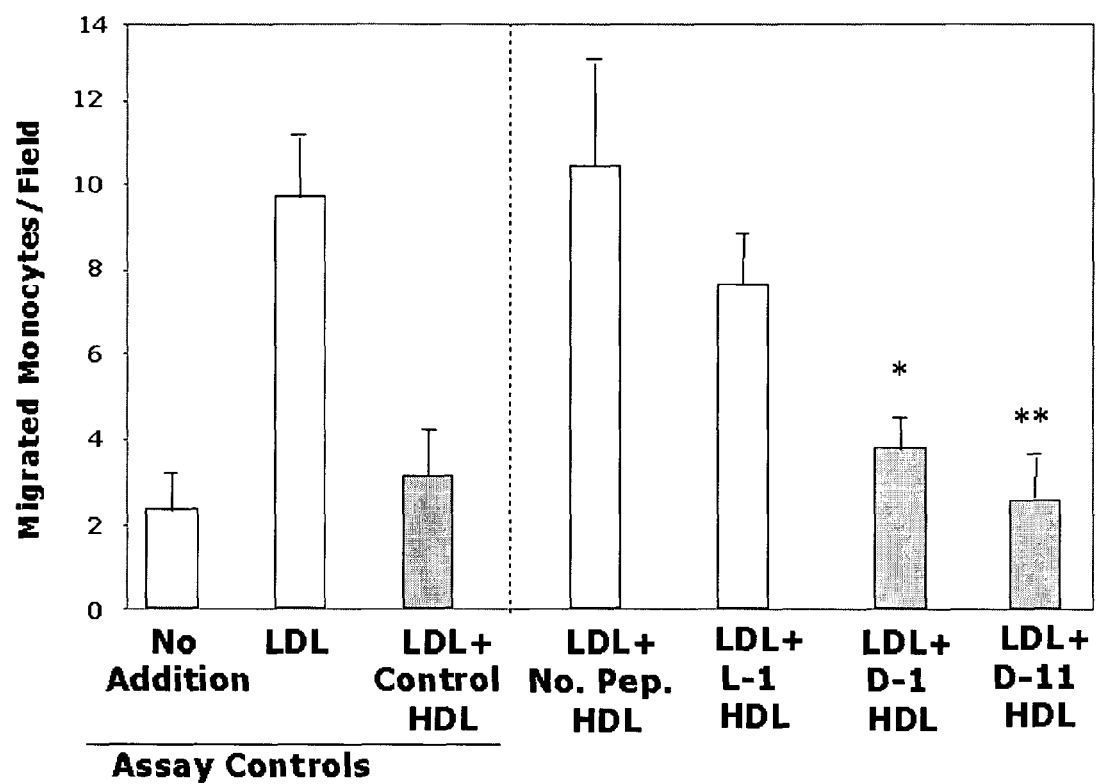
FIG. 16. SEQ ID NO:238 (designated D-1) and SEQ ID NO:258 (designated D-11) from Table 4 when synthesized from all D-amino acids and given orally renders HDL anti-inflammatory in apoE null mice but SEQ ID NO:238, when synthesized from all L-amino acids (L-1) and given orally did not. Female, 3 month old apoE null mice, (n=4), were given access to standard mouse chow in powdered form and containing 0.5 milligram of each peptide added per 1.0 gram of powdered mouse chow in a total of 4 grams of powdered mouse chow containing a total of 2.0 milligrams of the peptide for the cage of four mice or they were given the same powdered mouse chow without peptide. The chow was available to the mice for 24 hrs at which time the chow was consumed and the mice were bled. Plasma was separated and HDL was isolated by FPLC. Cultures of human aortic endothelial cells received medium alone (No Addition/Assay Controls), standard normal human LDL at 100 μgm/mL cholesterol without (LDL/Assay Controls) or together with standard control human HDL (LDL+Control HDL/Assay Controls) at 50 μgm/mL cholesterol, or control human LDL at 100 μgm/mL cholesterol was added with mouse HDL at 50 μgm/mL cholesterol obtained from mice that received no peptide (LDL+No Pep. HDL), or SEQ ID NO:238 made from all L-amino acids (LDL+L-1 HDL),or SEQ ID NO:238 made from all D-amino acids (LDL+D-1 HDL) or SEQ ID NO:258 made from all D-amino acids (LDL+D-11 HDL). The cultures were incubated for 8 hrs. The supernatants were then assayed for monocyte chemotactic activity. The values are mean+/−SD of the number of migrated monocytes in 9 high power fields. * indicates $p<0.01$ and ** indicates $p<0.001$.
Figure 17:
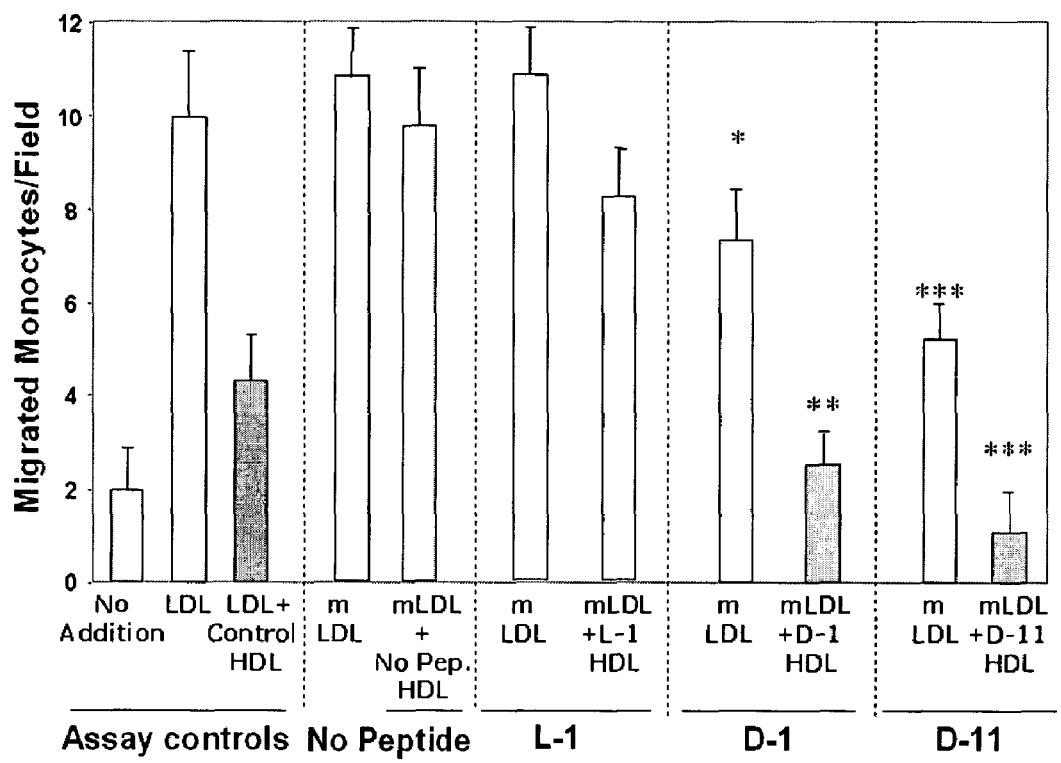
FIG. 17. SEQ ID NO:238 (D-1) and SEQ ID NO:258 (D-11) from Table 4 when synthesized from all D-amino acids and given orally renders HDL anti-inflammatory and reduces LDL-induced monocyte chemotactic activity in apoE null mice but SEQ ID NO:238, when synthesized from all L-amino acids and given orally, did not. Plasma from the mice described in FIG. 16 was separated and HDL and LDL were isolated by FPLC. Cultures of human aortic endothelial cells received medium alone (No Addition/Assay Controls), standard normal human LDL at 100 μgm/mL cholesterol without (LDL/Assay Controls) or together with standard control human HDL (LDL+Control HDL/Assay Controls) at 50 μgm/mL cholesterol, or autologous mouse LDL at 100 μgm/mL cholesterol alone (mLDL) or with mouse HDL at 50 μgm/mL cholesterol obtained from mice that received no peptide (mLDL+No Pep. HDL),or SEQ ID NO:238 made from all L-amino acids (mLDL+L-1 HDL), or SEQ ID NO:238 made from all D-amino acids (mLDL+D-1 HDL) or SEQ ID NO:258 made from all D-amino acids (mLDL+D-11 HDL). The cultures were incubated for 8 hrs. The supernatants were then assayed for monocyte chemotactic activity. The values are mean+/−SD of the number of migrated monocytes in 9 high power fields. * indicates $p<0.05$,  indicates $p<0.01$ and * indicates $p<0.001$.
Figure 18:
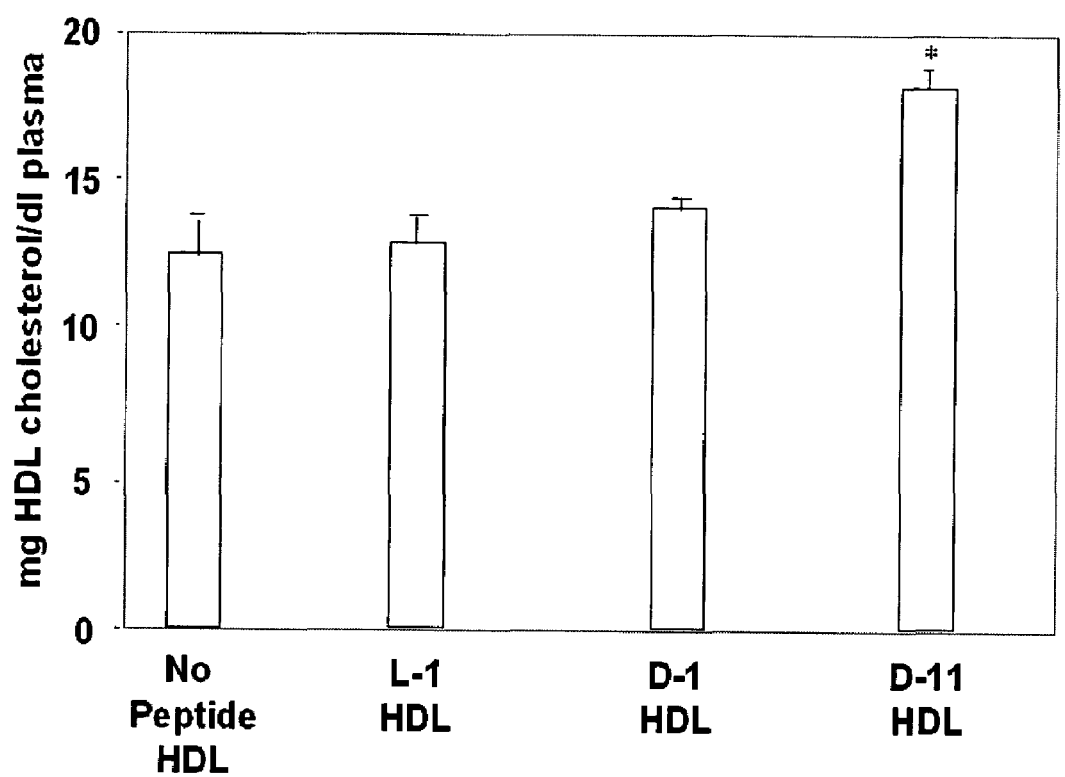
FIG. 18. SEQ ID NO:258 from Table 4 synthesized from all D-amino acids (D-11), when given orally to mice, raised HDL cholesterol concentrations while giving SEQ ID NO:238 synthesized from either L- or D-amino acids (L-1 or D-1, respectively) orally did not. Plasma HDL-cholesterol concentrations from the mice that are described in FIGS. 16 and 17 were determined. No Peptide HDL, plasma HDL-cholesterol in mice that received no peptide; L-1 HDL, plasma HDL-cholesterol in mice that received SEQ ID NO:238 synthesized from L-amino acids; D-1 HDL, plasma HDL-cholesterol in mice that received SEQ ID NO:238 synthesized from D-amino acids; D-11 HDL, plasma HDL-cholesterol in mice that received SEQ ID NO:258 synthesized from D-amino acids. *indicates $p<0.001$.

FIG. 14 demonstrates that the peptide described in Table 4 as SEQ ID NO:258, when synthesized from all L-amino acids and given to apoE null mice orally converted pro-inflammatory HDL to anti-inflammatory and increased plasma paraoxonase activity (FIG. 15).

Figure 19:
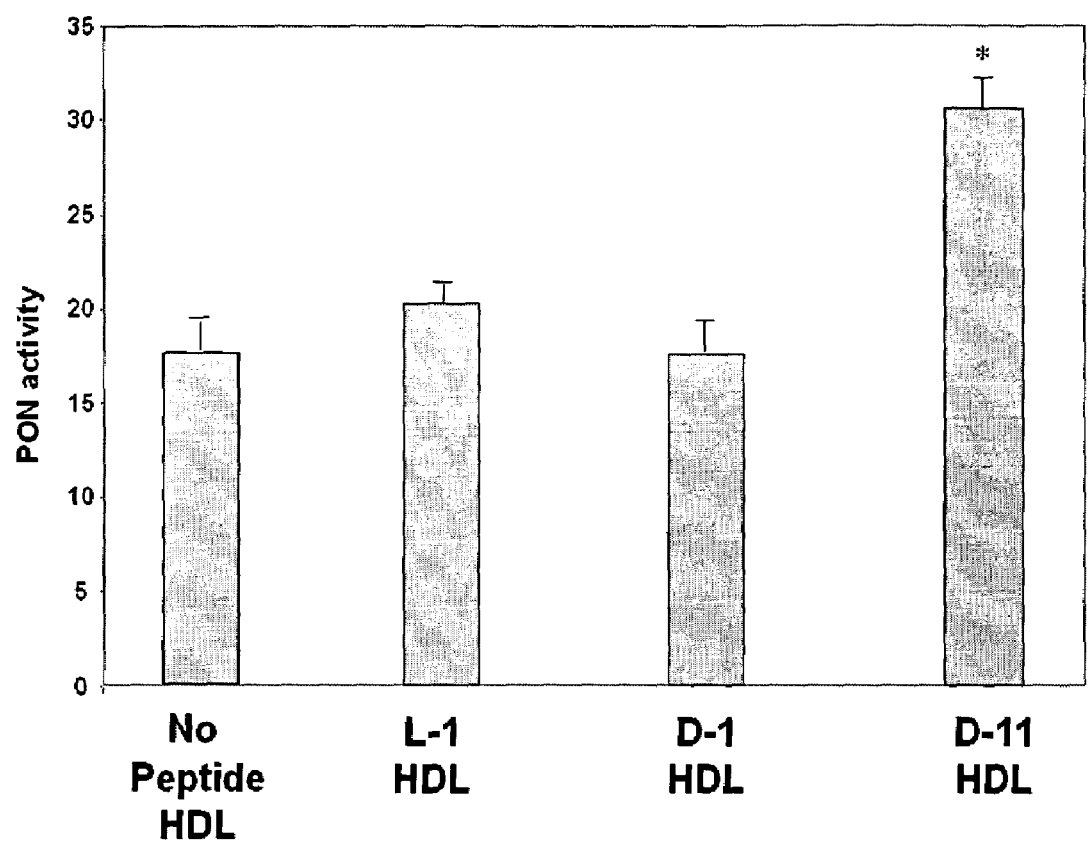
FIG. 19. SEQ ID NO:258 from Table 4 synthesized from all D-amino acids (D-11) when given orally to mice raised HDL paraoxonase (PON) activity while giving SEQ ID NO:238 synthesized from either L- or D- amino acids (L-1, D-1, respectively) orally did not. Paraoxonase activity in the HDL described in FIG. 18 was determined. The values are activity per 500 microliters of plasma. *indicates $p<0.001$.

FIGS. 16, 17, 18, and 19 demonstrate that the peptide described in Table 4 as SEQ ID NO:258 when synthesized from all D-amino acids and given orally to apoE null mice rendered HDL anti-inflammatory (FIGS. 16 and 17), reducing LDL-induced monocyte chemotactic activity (FIG. 17) and increasing plasma HDL-cholesterol (FIG. 18) and increasing HDL paraoxonase activity (FIG. 19). These data also show that SEQ ID NO:238, when synthesized from all L-amino acids and given orally to apoE null mice, did not significantly alter HDL inflammatory properties (FIGS. 16 and 17) nor did it significantly alter LDL-induced monocyte chemotactic activity (FIG. 17) nor did it significantly alter plasma HDL-cholesterol concentrations (FIG. 18), nor did it significantly alter HDL paraoxonase activity (FIG. 19). Additionally these data show that when SEQ ID NO:238 from Table 4 was synthesized from all D-amino acids and was given orally to apoE null mice, HDL was rendered anti-inflammatory (FIGS. 16 and 17), and reduced LDL-induced monocyte chemotactic activity (FIG. 17), but neither change was as dramatic as with SEQ ID NO:258. Moreover, unlike SEQ ID NO:258, SEQ ID NO:238 from Table 4 when synthesized from all D-amino acids did not raise plasma HDL-cholesterol concentrations (FIG. 18) and did not increase HDL paraoxonase activity (FIG. 19). We conclude that SEQ ID NO:238 from Table 4 when synthesized from L-amino acids is not effective when given orally but is effective when synthesized from D-amino acids, but is substantially less effective than SEQ ID NO:258.

The data presented herein demonstrate that SEQ ID NO:238 when synthesized from all L-amino acids and given orally is generally ineffective, and when synthesized from all D-amino acids, while effective, is substantially less effective than the same dose of SEQ ID NO:258 synthesized from all D-amino acids when administered orally.

Example 2

Peptides Synergize Statin Activity

Figure 20:
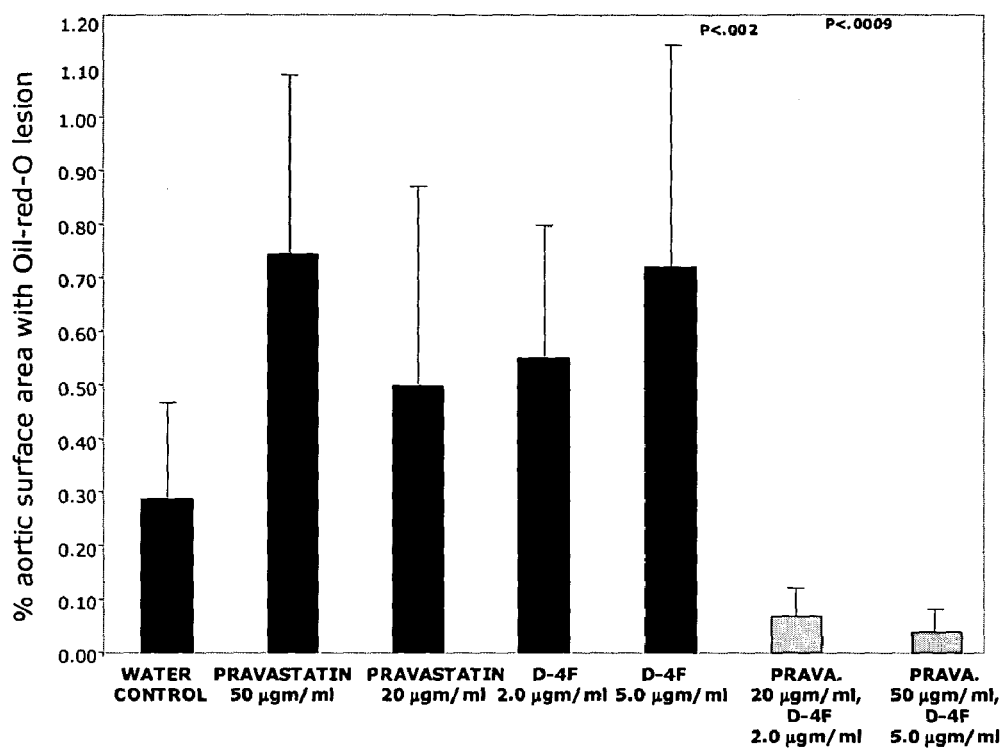
FIG. 20. Pravastatin and D-4F act synergistically to reduce aortic lesions as determine in en face preparations in apoE null mice. Five week old female apoE null mice were given in their drinking water either no additions (water control), pravastatin 50 μg/ml, pravastatin 20 μg/ml or D-4F 2 μg/ml, or D-4F 5 μg/ml, or pravastatin (PRAVA.) 20 μg/ml together with D-4F 2 μg/ml, or pravastatin (PRAVA.) 50 μg/ml together with D-4F 5 μg/ml. After 11 weeks the mice were sacrificed and lesions determined in en face aortic preparations.
Figure 21:
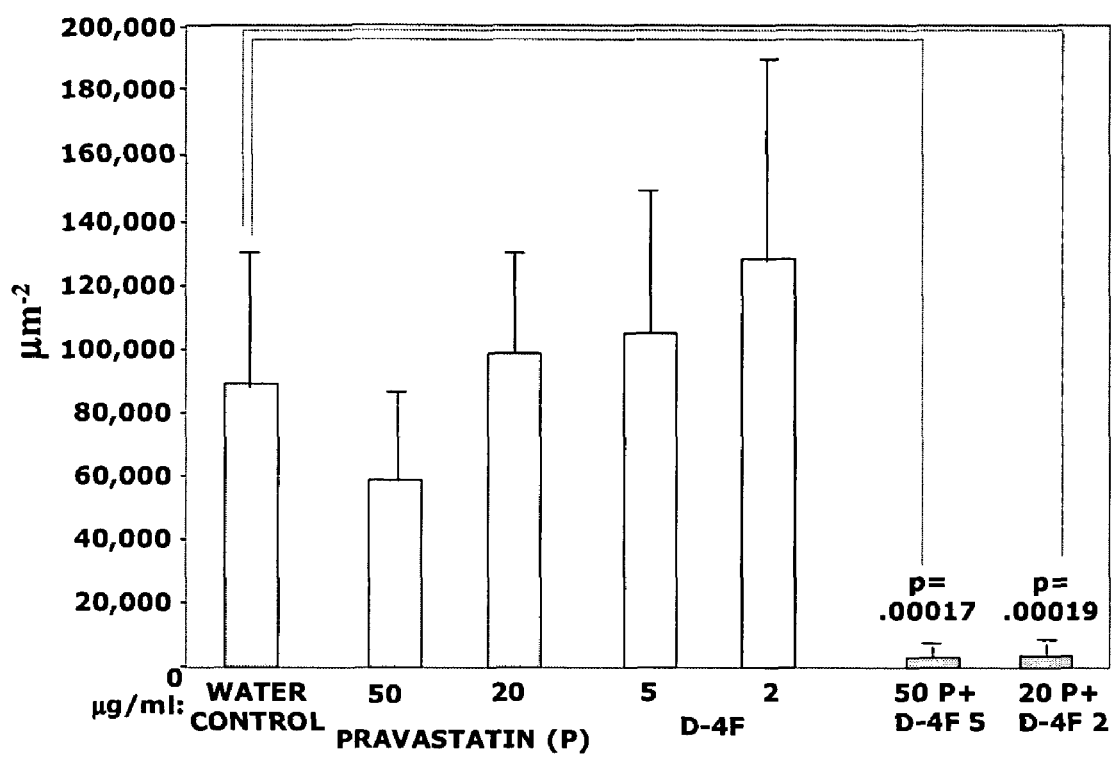
FIG. 21. Pravastatin and D-4F act synergistically to reduce aortic sinus lesions in apoE null mice. Five week old female apoE null mice were given in their drinking water either no additions (water control), pravastatin 50 μg/ml, pravastatin 20 μg/ml or D-4F 2 μg/ml, or D-4F 5 μg/ml, or pravastatin (P) 50 μg/ml together with D-4F 5 μg/ml, or pravastatin (P) 20 μg/ml together with D-4F 2 μg/ml. After 11 weeks the mice were sacrificed and aortic sinus lesions were determined.

FIGS. 20 and 21 show the very dramatic synergy between a statin (pravastatin) and D-4F in ameliorating atherosclerosis in apoE null mice. Mice are known to be resistant to statins. The mice that received pravastatin in their drinking water at 20 µg/ml consumed a dose of pravastatin equal to 175 mg per day for a 70 Kg human and the mice that received pravastatin in their drinking water at 50 µg/ml consumed a dose of pravastatin equal to 437.5 mg per day for a 70 Kg human. As shown in FIGS. 20 and 21, these very high doses of pravastatin were not effective in ameliorating atherosclerotic lesions in apoE null mice. As shown in FIGS. 20 and 21, adding D-4F alone to the drinking water of the apoE null mice at concentrations of 2 µg/ml or 5 µg/ml did not reduce atherosclerotic lesions. These doses of D-4F would be equivalent to doses of 17.5 mg per day, and 43.75 mg per day, respectively, for a 70 Kg human. Remarkably, as shown in FIGS. 20 and 21, adding the same concentrations of pravastatin and D-4F together to the drinking water of the apoE null mice essentially abolished atherosclerosis in these mice. This indicates a very high degree of synergy between a statin (pravastatin) and D-4F.

Figure 22:
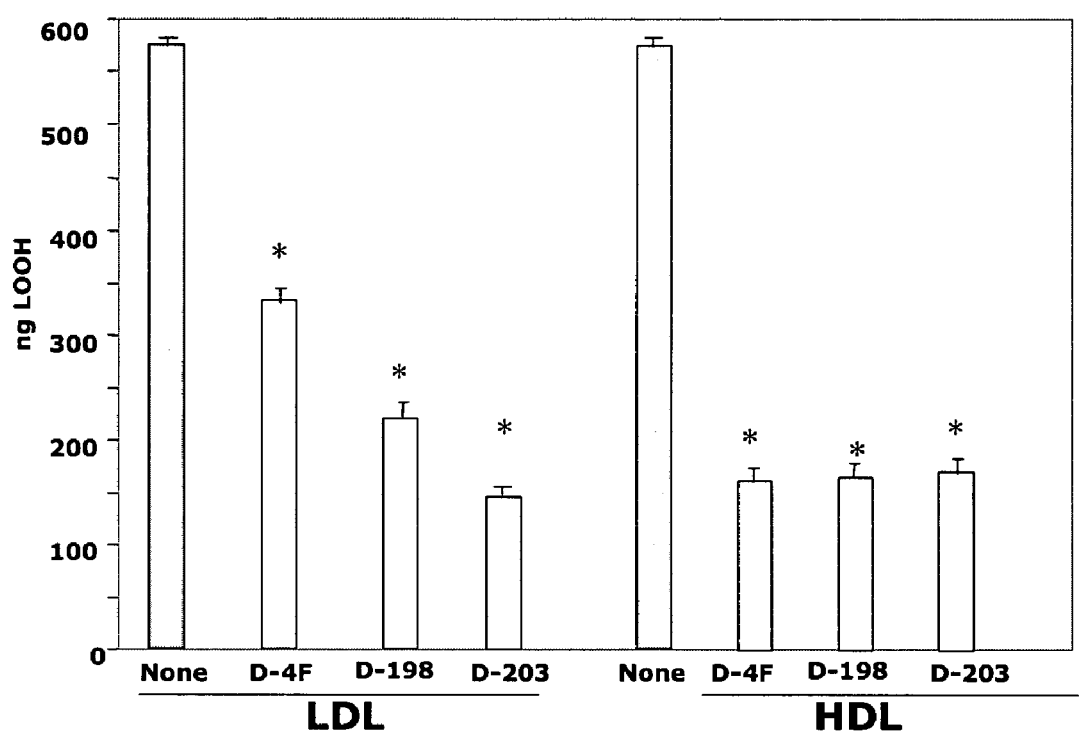
FIG. 22. D-4F and SEQ ID NO:242 and SEQ ID NO:258 from Table 4 dramatically reduce lipoprotein lipid hydroperoxides in apoE null mice. Fifty μg/gm of SEQ ID NO:242 (D-198 in the drawing) or SEQ ID NO:258 (D-203 in the drawing) or D-4F (the peptides were synthesized from all D-amino acids) were added to the chow of apoE null mice or the mice were continued on chow without additions (None). Eighteen hours later the mice were bled, their plasma fractionated by FPLC and the lipid hydroperoxide (LOOH) content of their low density lipoproteins (LDL) and high density lipoproteins (HDL) were determined. *indicates $p<0.01$.

FIG. 22 shows that SEQ ID NO:242 and SEQ ID NO:258 from Table 4 were equally effective or even more effective than D-4F in reducing the lipid hydroperoxide content of both LDL and HDL in apoE null mice. These data are consistent with D-4F and the peptides described in this application acting in part by sequestering the "seeding molecules" necessary for LDL to induce the inflammatory atherosclerotic reaction. Taken together with the data shown in FIGS. 3 to 19 it is very likely that the peptides described in this application (e.g. SEQ ID NO. 198 and SEQ ID NO. 203 from Table 4) will be as or more effective than D-4F in ameliorating atherosclerosis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A peptide that ameliorates one or more symptoms of an inflammatory condition, wherein said peptide is a peptide of the formula:

$X^1$-$X^2$-$X^3$-$X^4$ wherein:
$X^1$ and $X^4$ are independently selected from the group consisting of alanine (Ala), valine (Val), leucine (Leu), isoleucine (Ile), proline (Pro), phenylalanine (Phe), tryptophan (Trp), methionine (Met), serine (Ser) bearing a hydrophobic protecting group, beta-naphthyl alanine, alpha-naphthyl alanine, norleucine, cyclohexylalanine, threonine (Thr) bearing a hydrophobic protecting group, tyrosine (Tyr) bearing a hydrophobic protecting group, lysine (Lys) bearing a hydrophobic protecting group, arginine (Arg) bearing a hydrophobic protecting group, ornithine (Orn) bearing a hydrophobic protecting group, aspartic acid (Asp) bearing a hydrophobic protecting group, cysteine (Cys) bearing a hydrophobic protecting group, and glutamic acid (Glu) bearing a hydrophobic protecting group; and
$X^2$ and $X^3$ are independently selected from the group consisting of Asp, Arg, and Glu, wherein when $X^2$ is an acidic amino acid; $X^3$ is a basic amino acid, and when $X^2$ is a basic amino acid $X^3$ is an acidic amino acid;
said peptide converts pro-inflammatory HDL to anti-inflammatory HDL or makes anti-inflammatory HDL more anti-inflammatory; and
said peptide does not consist of the amino acid sequence Lys-Arg-Asp-Ser (SEQ ID NO:238) in which Lys-Arg-Asp and Ser are all L amino acids.

2. The peptide of claim 1, wherein:
$X^1$-$X^2$-$X^3$-$X^4$ consists of the amino acid sequence Phe-Arg-Glu-Leu (SEQ ID NO:250).

3. The peptide of claim 1, wherein said peptide comprises at least one "D" amino acid.

4. The peptide of claim 3, wherein said peptide consists of all "D" amino acids.

5. The peptide of claim 2, wherein said peptide comprises at least one "D" amino acid.

6. The peptide of claim 5, wherein said peptide consists of all "D" amino acids.

7. The peptide of any one of claims 1, 2, 3, 4, or 6, wherein $X^1$ bears a hydrophobic protecting group.

8. The peptide of claim 7, wherein said hydrophobic protecting group is selected from the group consisting of t-butoxycarbonyl (Boc), Fmoc, nicotinyl, OtBu, a benzoyl group, an acetyl (Ac), a carbobenzoxy, a methyl ester, a propyl ester, a butyl ester, a pentyl ester, a hexyl ester, an N-methyl anthranilyl, a 3 to 20 carbon alkyl, amide, 9-fluorenacetyl group, 1-fluorenecarboxylic group, 9-fluorenecarboxylic group, 9-fluorenone-1-carboxylic group, , Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-Butyl (tBu), trifluoroacetyl (TFA), 4[N-{1-(4,4-dimethyl-2,6-dioxocyclohexylidene)-3-methyldibutyl}-amino] benzyl ester (ODmab), α-allyl ester (OAll), 2-phenylisopropyl ester (2-PhiPr), and 1-[4,4-dimethyl-2,6-dioxycyclohex-1-yl-idene]ethyl (Dde).

9. The peptide of claim 7, wherein said hydrophobic protecting group is selected from the group consisting of Boc, Fmoc, nicotinyl, and OtBu.

10. The peptide of claim 7, wherein $X^4$ bears a hydrophobic protecting group.

11. The peptide of claim 10, wherein said hydrophobic protecting group is selected from the group consisting of t-butoxycarbonyl (Boc), Fmoc, nicotinyl, OtBu, a benzoyl group, an acetyl (Ac), a carbobenzoxy, a methyl ester, a propyl ester, a butyl ester, a pentyl ester, a hexyl ester, an N-methyl anthranilyl, a 3 to 20 carbon alkyl, amide, 9-fluorenacetyl group, 1-fluorenecarboxylic group, 9-fluorenecarboxylic group, 9-fluorenone-1-carboxylic group, , Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-Butyl (tBu), trifluoroacetyl (TFA), 4[N-{1-(4,4-dimethyl-2,6-dioxocyclohexylidene)-3-methyldibutyl}-amino]benzyl ester (ODmab), α-allyl ester (OAll), 2-phenylisopropyl ester (2-PhiPr), and 1-[4,4-dimethyl-2,6-dioxycyclohex-1-yl-idene]ethyl (Dde).

12. The peptide of claim 7, wherein the N-terminus of said peptide is blocked with a protecting group selected from the group consisting of Boc-, Fmoc-, and Nicotinyl-.

13. The peptide of claim 7, wherein the C-terminus of said peptide is blocked with a protecting group selected from the group consisting of tBu, and OtBu.

14. The peptide of claim 1, wherein said peptide comprises alternating D- and L-amino acids.

15. The peptide of claim 1, wherein said peptide comprises all L-amino acids.

16. The peptide of claims 1 or 2, wherein said peptide is mixed with a pharmacologically acceptable excipient.

17. The peptide of claim 16, wherein said peptide is mixed with a pharmacologically acceptable excipient suitable for oral administration to a mammal.

18. The peptide of claim 16, wherein said peptide is provided as a unit formulation in a pharmaceutically acceptable excipient.

19. The peptide of claims 1 or 2, wherein said peptide is provided as a time release formulation.

20. The peptide of claims 1 or 2, wherein said peptide protects a phospholipid against oxidation by an oxidizing agent.

21. The peptide of claim 2, wherein said peptide is coupled to a biotin.

22. A pharmaceutical formulation comprising:
one or more peptides according to claims 1, 2, 3, 4, and 6; and
a pharmaceutically acceptable excipient;
wherein the peptide is present in a dose effective to ameliorate one or more symptoms of an inflammatory condition.

23. The pharmaceutical formulation of claim 22, wherein said peptide consists of all "D" amino acids.

24. The pharmaceutical formulation of claim 22, wherein the peptide is in a time release formulation.

25. The pharmaceutical formulation of claim 22, wherein the formulation is formulated as a unit dosage formulation.

26. The pharmaceutical formulation of claim 22, wherein the formulation is formulated for oral administration.

27. The pharmaceutical formulation of claim 22, wherein the formulation is formulated for administration by a route selected from the group consisting of oral administration, nasal administration, rectal administration, intraperitoneal injection, intravascular injection, subcutaneous injection, transcutaneous administration, inhalation administration, and intramuscular injection.

28. A kit comprising:
a container containing one or more of the peptides according to claims 1, 2, 3, 4, and 6; and
instructional materials teaching the use of the peptide(s) in the treatment of a pathology characterized by inflammation.

29. The kit of claim 28, wherein said pathology is a pathology selected from the group consisting of atherosclerosis, rheumatoid arthritis, lupus erythematosus, polyarteritis nodosa, osteoporosis, Alzheimer's disease, and a viral illness.

30. A method of mitigating one or more symptoms of atherosclerosis in a mammal, said method comprising administering to said mammal an effective amount of one or more of the peptides of claims 1, 2, 3, 4, and 6.

31. The method of claim 30, wherein said peptide is in a pharmaceutically acceptable excipient.

32. The method of claim 30, wherein said peptide is administered in conjunction with a lipid.

33. The method of claim 30, wherein said peptide is in a pharmaceutically acceptable excipient suitable for oral administration.

34. The method of claim 30, wherein said peptide is administered as a unit dosage formulation.

35. The method of claim 30, wherein said administering comprises administering said peptide by a route selected from the group consisting of oral administration, nasal administration, rectal administration, intraperitoneal injection, intravascular injection, subcutaneous injection, transcutaneous administration, and intramuscular injection.

36. The method of claim 30, wherein said mammal is a mammal diagnosed as having one or more symptoms of atherosclerosis.

37. The method of claim 30, wherein said mammal is a mammal diagnosed as at risk for stroke or atherosclerosis.

38. The method of claim 30, wherein said mammal is a human.

39. The method of claim 30, wherein said mammal is non-human mammal.

40. A method of mitigating one or more symptoms of an inflammatory pathology in a mammal, said method comprising administering to said mammal an effective amount of one or more of the peptides of claims 1, 2, 3, 4, and 6.

41. The method of claim 40, wherein said inflammatory pathology is a pathology selected from the group consisting of atherosclerosis, rheumatoid arthritis, lupus erythematosus, polyarteritis nodosa, osteoporosis, Alzheimer's disease, multiple sclerosis, and a viral illness.

42. The method of claim 40, wherein said peptide is in a pharmaceutically acceptable excipient.

43. The method of claim 40, wherein said peptide is administered in conjunction with a lipid.

44. The method of claim 40, wherein said peptide is in a pharmaceutically acceptable excipient suitable for oral administration.

45. The method of claim 40, wherein said peptide is administered as a unit dosage formulation.

46. The method of claim 40, wherein said administering comprises administering said peptide by a route selected from the group consisting of oral administration, nasal administration, rectal administration, intraperitoneal injection, intravascular injection, subcutaneous injection, transcutaneous administration, and intramuscular injection.

47. The method of claim 40, wherein said mammal is a mammal diagnosed as at risk for stroke.

48. The method of claim 40, wherein said mammal is a human.

49. The method of claim 40, wherein said mammal is non-human mammal.

50. A method of enhancing the activity of a statin in a mammal, said method comprising coadministering with said statin an effective amount of one or more of the peptides of claims 1, 2, 3, 4, and 6.

51. The method of claim 50, wherein said statin is selected from the group consisting of cerivastatin, atorvastatin, simvastatin, pravastatin, fluvastatin, lovastatin, rosuvastatin, and pitavastatin.

52. The method of claim 50, wherein said peptide is administered simultaneously with said statin.

53. The method of claim 50, wherein said peptide is administered before said statin.

54. The method of claim 50, wherein said peptide is administered after said statin.

55. The method of claim 50, wherein said peptide and/or said statin are administered as a unit dosage formulation.

56. The method of claim 50, wherein said administering comprises administering said peptide and/or said statin by a route selected from the group consisting of oral administration, nasal administration, rectal administration, intraperitoneal injection, intravascular injection, subcutaneous injection, transcutaneous administration, and intramuscular injection.

57. The method of claim 50, wherein said mammal is a mammal diagnosed as having one or more symptoms of atherosclerosis.

58. The method of claim 50, wherein said mammal is a mammal diagnosed as at risk for stroke or atherosclerosis.

59. The method of claim 50, wherein said mammal is a human.

60. The method of claim 50, wherein said mammal is non-human mammal.

61. A method of mitigating one or more symptoms associated with atherosclerosis in a mammal, said method comprising:
administering to said mammal an effective amount of a statin; and
an effective amount of one or more peptides of claims 1, 2, 3, 4, and 6;
wherein the effective amount of the statin is lower than the effective amount of a statin administered without said peptide.

62. The method of claim 61, wherein the effective amount of the peptide is lower than the effective amount of the peptide administered without said statin.

63. The method of claim 61, wherein said statin is selected from the group consisting of cerivastatin, atorvastatin, simvastatin, pravastatin, fluvastatin, lovastatin, rosuvastatin, and pitavastatin.

64. The method of claim 61, wherein said peptide is administered simultaneously with said statin.

65. The method of claim 61, wherein said peptide is administered before said statin.

66. The method of claim 61, wherein said peptide is administered after said statin.

67. The method of claim 61, wherein said peptide and/or said statin are administered as a unit dosage formulation.

68. The method of claim 61, wherein said administering comprises orally administering said one or more peptides.

69. The method of claim 61, wherein said administering is by a route selected from the group consisting of oral administration, nasal administration, rectal administration, intraperitoneal injection, intravascular injection, subcutaneous injection, transcutaneous administration, inhalation administration, and intramuscular injection.

70. The method of claim 61, wherein said mammal is a mammal diagnosed as having one or more symptoms of atherosclerosis.

71. The method of claim 61, wherein said mammal is a mammal diagnosed as at risk for stroke or atherosclerosis.

72. The method of claim 61, wherein said mammal is a human.

73. The method of claim 61, wherein said mammal is non-human mammal.

74. A pharmaceutical formulation, the formulation comprising:
   a statin and/or Ezetimibe; and
   a peptide or a concatamer of a peptide according to any of claims 1, 2, 3, 4, and 6.

75. The pharmaceutical formulation of claim 74, wherein the peptide and/or the statin are present in an effective dose.

76. The pharmaceutical formulation of claim 75, wherein the effective amount of the statin is lower than the effective amount of the statin administered without the peptide.

77. The pharmaceutical formulation of claim 75, wherein the effective amount of the peptide is lower than the effective amount of the peptide administered without the statin.

78. The pharmaceutical formulation of claim 75, wherein the effective amount of the Ezetimibe is lower than the effective amount of the Ezetimibe administered without the peptide.

79. The pharmaceutical formulation of claim 75, wherein the effective amount of the peptide is lower than the effective amount of the peptide administered without the Ezetimibe.

80. The pharmaceutical formulation of claim 74, wherein the statin is selected from the group consisting of cerivastatin, atorvastatin, simvastatin, pravastatin, fluvastatin, lovastatin, rosuvastatin, and pitavastatin.

81. The pharmaceutical formulation of claim 74, wherein the Ezetimibe, the statin, and/or the peptide are in a time release formulation.

82. The pharmaceutical formulation of claim 74, wherein the formulation is formulated as a unit dosage formulation.

83. The pharmaceutical formulation of claim 74, wherein the formulation is formulated for oral administration.

84. The pharmaceutical formulation of claim 74, wherein the formulation is formulated for administration by a route selected from the group consisting of oral administration, nasal administration, rectal administration, intraperitoneal injection, intravascular injection, subcutaneous injection, transcutaneous administration, inhalation administration, and intramuscular injection.

85. The pharmaceutical formulation of claim 74, wherein the formulation further comprises one or more phospholipids.

* * * * *

UNITED STATES PATENT AND TRADEMARK OFFICE
CERTIFICATE OF CORRECTION

| | |
|---|---|
| PATENT NO. | : 7,148,197 B2 |
| APPLICATION NO. | : 10/649378 |
| DATED | : December 12, 2006 |
| INVENTOR(S) | : Fogelman et al. |

It is certified that error appears in the above-identified patent and that said Letters Patent is hereby corrected as shown below:

On the Cover Page:
Column 1, Field (73), change "The University of Alabama Research Foundation, Birmingham, AL (US)" to -- The UAB Research Foundation, Birmingham, AL (US) --

Column 1, Field (75), change "Gattadahalli M Anantharamaiah, Birmingham, CA (US)" to -- Gattadahalli M Anantharamaiah, Birmingham, AL (US) --

In the Specification:
Column 1, line 15-20, change "This work was supported by United States Public Health Service and National Heart, Lung, and Blood Institute Grants HL30568 and HL34343. The Government of the United States of America may have certain rights in this invention." to -- This invention was made with Government support of Grant No. HL30568 and HL34343 awarded by the National Institutes of Health. The Government has certain rights in this invention. --

Signed and Sealed this

Sixth Day of July, 2010

David J. Kappos
*Director of the United States Patent and Trademark Office*

SEQUENCE LISTING

<160> NUMBER OF SEQ ID NOS: 464

<210> SEQ ID NO 1
<211> LENGTH: 18
<212> TYPE: PRT
<213> ORGANISM: Artificial Sequence
<220> FEATURE:
<223> OTHER INFORMATION: Chemically synthesized peptide.  Amino acids
      can be protected or unprotected D or L form.
<220> FEATURE:
<221> NAME/KEY: misc_feature
<222> LOCATION: (1)..(1)
<223> OTHER INFORMATION: Xaa is aspartic acid or glutamic acid.
<220> FEATURE:
<221> NAME/KEY: misc_feature
<222> LOCATION: (2)..(3)
<223> OTHER INFORMATION: Xaa is tryptophan, phenylalanine, alanine,
      leucine, tyrosine, isoleucine, valine or alpha-naphthylalanine.
<220> FEATURE:
<221> NAME/KEY: misc_feature
<222> LOCATION: (4)..(4)
<223> OTHER INFORMATION: Xaa is lysine, or arginine.
<220> FEATURE:
<221> NAME/KEY: misc_feature
<222> LOCATION: (5)..(5)
<223> OTHER INFORMATION: Xaa is serine, threonine, alanine, glycine,
      or histidine,.
<220> FEATURE:
<221> NAME/KEY: misc_feature -continued

```
<222> LOCATION: (6)..(7)
<223> OTHER INFORMATION: Xaa is tryptophan, phenylalanine, alanine,
      leucine, tyrosine, isoleucine, valine or alpha-naphthylalanine.
<220> FEATURE:
<221> NAME/KEY: misc_feature
<222> LOCATION: (8)..(8)
<223> OTHER INFORMATION: Xaa is aspartic acid or glutamic acid.
<220> FEATURE:
<221> NAME/KEY: misc_feature
<222> LOCATION: (9)..(9)
<223> OTHER INFORMATION: Xaa is lysine or arginine
<220> FEATURE:
<221> NAME/KEY: misc_feature
<222> LOCATION: (10)..(11)
<223> OTHER INFORMATION: Xaa is tryptophan, phenylalanine, alanine,
      leucine, tyrosine, isoleucine, valine or alpha-naphthylalanine.
<220> FEATURE:
<221> NAME/KEY: misc_feature
<222> LOCATION: (12)..(12)
<223> OTHER INFORMATION: Xaa is aspartic acid or glutamic acid.
<220> FEATURE:
<221> NAME/KEY: misc_feature
<222> LOCATION: (13)..(13)
<223> OTHER INFORMATION: Xaa is lysine or arginine
<220> FEATURE:
<221> NAME/KEY: misc_feature
<222> LOCATION: (14)..(14)
<223> OTHER INFORMATION: Xaa is tryptophan, phenylalanine, alanine,
      leucine, tyrosine, isoleucine, valine or alpha-naphthylalanine.
<220> FEATURE:
<221> NAME/KEY: misc_feature
<222> LOCATION: (15)..(15)
<223> OTHER INFORMATION: Xaa is lysine or arginine
<220> FEATURE:
<221> NAME/KEY: misc_feature
<222> LOCATION: (16)..(16)
<223> OTHER INFORMATION: Xaa is aspartic acid or glutamic acid.
<220> FEATURE:
<221> NAME/KEY: misc_feature
<222> LOCATION: (17)..(18)
<223> OTHER INFORMATION: Xaa is tryptophan, phenylalanine, alanine,
      leucine, tyrosine, isoleucine, valine or alpha-naphthylalanine.

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 2
<211> LENGTH: 20
<212> TYPE: PRT
<213> ORGANISM: Artificial Sequence
<220> FEATURE:
<223> OTHER INFORMATION: Chemically synthesized peptide.  Amino acids
      can be protected or unprotected D or L form.
<220> FEATURE:
<221> NAME/KEY: misc_feature
<222> LOCATION: (1)..(1)
<223> OTHER INFORMATION: Xaa is Pro, Ala, Gly, Asn, Gln, or D-Pro
<220> FEATURE:
<221> NAME/KEY: misc_feature
<222> LOCATION: (2)..(2)
<223> OTHER INFORMATION: Xaa is is an aliphatic amino acid
<220> FEATURE:
<221> NAME/KEY: misc_feature
<222> LOCATION: (3)..(3)
<223> OTHER INFORMATION: Xaa is Leu
<220> FEATURE:
<221> NAME/KEY: misc_feature
<222> LOCATION: (4)..(4)
<223> OTHER INFORMATION: Xaa is an acidic amino acid
<220> FEATURE:
<221> NAME/KEY: misc_feature
<222> LOCATION: (5)..(6)
<223> OTHER INFORMATION: Xaa is  Leu, or Phe
<220> FEATURE:
```

```
<221> NAME/KEY: misc_feature
<222> LOCATION: (7)..(7)
<223> OTHER INFORMATION: Xaa is a basic amino acid
<220> FEATURE:
<221> NAME/KEY: misc_feature
<222> LOCATION: (8)..(8)
<223> OTHER INFORMATION: Xaa is an acidic amino acid
<220> FEATURE:
<221> NAME/KEY: misc_feature
<222> LOCATION: (9)..(10)
<223> OTHER INFORMATION: Xaa is Leu, or Trp
<220> FEATURE:
<221> NAME/KEY: misc_feature
<222> LOCATION: (11)..(11)
<223> OTHER INFORMATION: Xaa is an acidic amino acid or Asn
<220> FEATURE:
<221> NAME/KEY: misc_feature
<222> LOCATION: (12)..(12)
<223> OTHER INFORMATION: Xaa is an acidic amino acid
<220> FEATURE:
<221> NAME/KEY: misc_feature
<222> LOCATION: (13)..(13)
<223> OTHER INFORMATION: Xaa is Leu, Trp, or Phe
<220> FEATURE:
<221> NAME/KEY: misc_feature
<222> LOCATION: (14)..(14)
<223> OTHER INFORMATION: Xaa is a basic amino acid or Leu
<220> FEATURE:
<221> NAME/KEY: misc_feature
<222> LOCATION: (15)..(15)
<223> OTHER INFORMATION: Xaa is Gln, or Asn
<220> FEATURE:
<221> NAME/KEY: misc_feature
<222> LOCATION: (16)..(16)
<223> OTHER INFORMATION: Xaa is a basic amino acid
<220> FEATURE:
<221> NAME/KEY: misc_feature
<222> LOCATION: (17)..(17)
<223> OTHER INFORMATION: Xaa is Leu
<220> FEATURE:
<221> NAME/KEY: misc_feature
<222> LOCATION: (18)..(18)
<223> OTHER INFORMATION: Xaa is a basic amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 3
<211> LENGTH: 18
<212> TYPE: PRT
<213> ORGANISM: Artificial Sequence
<220> FEATURE:
<223> OTHER INFORMATION: Chemically synthesized peptide.
     Amino acids can be protected or unprotected D or L form.

<400> SEQUENCE: 3

Asp Trp Leu Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial Sequence
<220> FEATURE:
<223> OTHER INFORMATION: Chemically synthesized peptide.
```

Amino acids can be protected or unprotected D or L form.

<400> SEQUENCE: 4

Asp Trp Leu Lys Ala Phe Tyr Asp Lys Val Ala Glu Lys Leu Lys Glu
1               5                   10                  15

Ala Phe

<210> SEQ ID NO 5
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 5

Asp Trp Leu Lys Ala Phe Tyr Asp Lys Val Ala Glu Lys Leu Lys Glu
1               5                   10                  15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 6

Asp Trp Phe Lys Ala Phe Tyr Asp Lys Val Ala Glu Lys Leu Lys Glu
1               5                   10                  15

Ala Phe

<210> SEQ ID NO 7
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 7

Asp Trp Leu Lys Ala Phe Tyr Asp Lys Val Ala Glu Lys Phe Lys Glu
1               5                   10                  15

Ala Phe

<210> SEQ ID NO 8
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 8

Asp Trp Phe Lys Ala Phe Tyr Asp Lys Val Ala Glu Lys Phe Lys Glu
1               5                   10                  15

Ala Phe

<210> SEQ ID NO 9
<211> LENGTH: 18
<212> TYPE: PRT
<213> ORGANISM: Artificial Sequence
<220> FEATURE:

```
<223> OTHER INFORMATION: Chemically synthesized peptide.
      Amino acids can be protected or unprotected D or L form.

<400> SEQUENCE: 9

Asp Trp Leu Lys Ala Phe Tyr Asp Lys Val Phe Glu Lys Phe Lys Glu
1               5                   10                  15

Phe Phe

<210> SEQ ID NO 10
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 10

Asp Trp Leu Lys Ala Phe Tyr Asp Lys Phe Phe Glu Lys Phe Lys Glu
1               5                   10                  15

Phe Phe

<210> SEQ ID NO 11
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 11

Asp Trp Phe Lys Ala Phe Tyr Asp Lys Phe Phe Glu Lys Phe Lys Glu
1               5                   10                  15

Phe Phe

<210> SEQ ID NO 12
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 12

Asp Trp Leu Lys Ala Phe Tyr Asp Lys Val Ala Glu Lys Leu Lys Glu
1               5                   10                  15

Phe Phe

<210> SEQ ID NO 13
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 13

Asp Trp Leu Lys Ala Phe Tyr Asp Lys Val Phe Glu Lys Phe Lys Glu
1               5                   10                  15

Ala Phe

<210> SEQ ID NO 14
<211> LENGTH: 18
<212> TYPE: PRT
<213> ORGANISM: Artificial Sequence
```

```
<220> FEATURE:
<223> OTHER INFORMATION: Chemically synthesized peptide.
      Amino acids can be protected or unprotected D or L form.

<400> SEQUENCE: 14

Asp Trp Leu Lys Ala Phe Tyr Asp Lys Val Phe Glu Lys Leu Lys Glu
1               5                   10                  15

Phe Phe

<210> SEQ ID NO 15
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 15

Asp Trp Leu Lys Ala Phe Tyr Asp Lys Val Ala Glu Lys Phe Lys Glu
1               5                   10                  15

Phe Phe

<210> SEQ ID NO 16
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 16

Asp Trp Leu Lys Ala Phe Tyr Asp Lys Val Phe Glu Lys Phe Lys Glu
1               5                   10                  15

Phe Phe

<210> SEQ ID NO 17
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 17

Glu Trp Leu Lys Leu Phe Tyr Glu Lys Val Leu Glu Lys Phe Lys Glu
1               5                   10                  15

Ala Phe

<210> SEQ ID NO 18
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 18

Glu Trp Leu Lys Ala Phe Tyr Asp Lys Val Ala Glu Lys Phe Lys Glu
1               5                   10                  15

Ala Phe

<210> SEQ ID NO 19
<211> LENGTH: 18
<212> TYPE: PRT
```

```
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 19

Glu Trp Leu Lys Ala Phe Tyr Asp Lys Val Ala Glu Lys Leu Lys Glu
1               5                   10                  15

Phe Phe

<210> SEQ ID NO 20
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 20

Glu Trp Leu Lys Ala Phe Tyr Asp Lys Val Phe Glu Lys Phe Lys Glu
1               5                   10                  15

Ala Phe

<210> SEQ ID NO 21
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 21

Glu Trp Leu Lys Ala Phe Tyr Asp Lys Val Phe Glu Lys Leu Lys Glu
1               5                   10                  15

Phe Phe

<210> SEQ ID NO 22
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 22

Glu Trp Leu Lys Ala Phe Tyr Asp Lys Val Ala Glu Lys Phe Lys Glu
1               5                   10                  15

Phe Phe

<210> SEQ ID NO 23
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 23

Glu Trp Leu Lys Ala Phe Tyr Asp Lys Val Phe Glu Lys Phe Lys Glu
1               5                   10                  15

Phe Phe

<210> SEQ ID NO 24
<211> LENGTH: 14
```

```
-continued

<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 24

Ala Phe Tyr Asp Lys Val Ala Glu Lys Leu Lys Glu Ala Phe
1               5                   10

<210> SEQ ID NO 25
<211> LENGTH: 14
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 25

Ala Phe Tyr Asp Lys Val Ala Glu Lys Phe Lys Glu Ala Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 27

Ala Phe Tyr Asp Lys Phe Phe Glu Lys Phe Lys Glu Phe Phe
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 28

Ala Phe Tyr Asp Lys Phe Phe Glu Lys Phe Lys Glu Phe Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 29

Ala Phe Tyr Asp Lys Val Ala Glu Lys Phe Lys Glu Ala Phe
```

-continued

<210> SEQ ID NO 30
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 30

Ala Phe Tyr Asp Lys Val Ala Glu Lys Leu Lys Glu Phe Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 31

Ala Phe Tyr Asp Lys Val Phe Glu Lys Phe Lys Glu Ala Phe
1               5                   10

<210> SEQ ID NO 32
<211> LENGTH: 14
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 32

Ala Phe Tyr Asp Lys Val Phe Glu Lys Leu Lys Glu Phe Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 33

Ala Phe Tyr Asp Lys Val Ala Glu Lys Phe Lys Glu Phe Phe
1               5                   10

<210> SEQ ID NO 34
<211> LENGTH: 14
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 34

Lys Ala Phe Tyr Asp Lys Val Phe Glu Lys Phe Lys Glu Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Chemically synthesized peptide.

Amino acids can be protected or unprotected D or L form.

<400> SEQUENCE: 35

Leu Phe Tyr Glu Lys Val Leu Glu Lys Phe Lys Glu Ala Phe
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 36

Ala Phe Tyr Asp Lys Val Ala Glu Lys Phe Lys Glu Ala Phe
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 37

Ala Phe Tyr Asp Lys Val Ala Glu Lys Leu Lys Glu Phe Phe
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 38

Ala Phe Tyr Asp Lys Val Phe Glu Lys Phe Lys Glu Ala Phe
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 39

Ala Phe Tyr Asp Lys Val Phe Glu Lys Leu Lys Glu Phe Phe
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 40

Ala Phe Tyr Asp Lys Val Ala Glu Lys Phe Lys Glu Phe Phe
1               5                   10

<210> SEQ ID NO 41

```
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 41

Ala Phe Tyr Asp Lys Val Phe Glu Lys Phe Lys Glu Phe Phe
1               5                   10

<210> SEQ ID NO 42
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 42

Asp Trp Leu Lys Ala Leu Tyr Asp Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 43

Asp Trp Phe Lys Ala Phe Tyr Glu Lys Val Ala Glu Lys Leu Lys Glu
1               5                   10                  15

Phe Phe

<210> SEQ ID NO 44
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 44

Asp Trp Phe Lys Ala Phe Tyr Glu Lys Phe Phe Glu Lys Phe Lys Glu
1               5                   10                  15

Phe Phe

<210> SEQ ID NO 45
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 45

Glu Trp Leu Lys Ala Leu Tyr Glu Lys Val Ala Glu Lys Leu Lys Glu
1               5                   10                  15

Ala Leu

<210> SEQ ID NO 46
<211> LENGTH: 18
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 46

Glu Trp Leu Lys Ala Phe Tyr Glu Lys Val Ala Glu Lys Leu Lys Glu
1               5                   10                  15

Ala Phe

<210> SEQ ID NO 47
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 47

Glu Trp Phe Lys Ala Phe Tyr Glu Lys Val Ala Glu Lys Leu Lys Glu
1               5                   10                  15

Phe Phe

<210> SEQ ID NO 48
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 48

Glu Trp Leu Lys Ala Phe Tyr Glu Lys Val Phe Glu Lys Phe Lys Glu
1               5                   10                  15

Phe Phe

<210> SEQ ID NO 49
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 49

Glu Trp Leu Lys Ala Phe Tyr Glu Lys Phe Phe Glu Lys Phe Lys Glu
1               5                   10                  15

Phe Phe

<210> SEQ ID NO 50
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 50

Glu Trp Phe Lys Ala Phe Tyr Glu Lys Phe Phe Glu Lys Phe Lys Glu
1               5                   10                  15

Phe Phe

<210> SEQ ID NO 51
```

-continued

```
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 51

Asp Phe Leu Lys Ala Trp Tyr Asp Lys Val Ala Glu Lys Leu Lys Glu
1               5                   10                  15

Ala Trp

<210> SEQ ID NO 52
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 52

Glu Phe Leu Lys Ala Trp Tyr Glu Lys Val Ala Glu Lys Leu Lys Glu
1               5                   10                  15

Ala Trp

<210> SEQ ID NO 53
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 53

Asp Phe Trp Lys Ala Trp Tyr Asp Lys Val Ala Glu Lys Leu Lys Glu
1               5                   10                  15

Trp Trp

<210> SEQ ID NO 54
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 54

Glu Phe Trp Lys Ala Trp Tyr Glu Lys Val Ala Glu Lys Leu Lys Glu
1               5                   10                  15

Trp Trp

<210> SEQ ID NO 55
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 55

Asp Lys Leu Lys Ala Phe Tyr Asp Lys Val Phe Glu Trp Ala Lys Glu
1               5                   10                  15

Ala Phe
```

```
<210> SEQ ID NO 56
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 56

Asp Lys Trp Lys Ala Val Tyr Asp Lys Phe Ala Glu Ala Phe Lys Glu
1               5                   10                  15

Phe Leu

<210> SEQ ID NO 57
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 57

Glu Lys Leu Lys Ala Phe Tyr Glu Lys Val Phe Glu Trp Ala Lys Glu
1               5                   10                  15

Ala Phe

<210> SEQ ID NO 58
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 58

Glu Lys Trp Lys Ala Val Tyr Glu Lys Phe Ala Glu Ala Phe Lys Glu
1               5                   10                  15

Phe Leu

<210> SEQ ID NO 59
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 59

Asp Trp Leu Lys Ala Phe Val Asp Lys Phe Ala Glu Lys Phe Lys Glu
1               5                   10                  15

Ala Tyr

<210> SEQ ID NO 60
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 60

Glu Lys Trp Lys Ala Val Tyr Glu Lys Phe Ala Glu Ala Phe Lys Glu
1               5                   10                  15

Phe Leu
```

```
<210> SEQ ID NO 61
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 61

Asp Trp Leu Lys Ala Phe Val Tyr Asp Lys Val Phe Lys Leu Lys Glu
1               5                   10                  15

Phe Phe

<210> SEQ ID NO 62
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 62

Glu Trp Leu Lys Ala Phe Val Tyr Glu Lys Val Phe Lys Leu Lys Glu
1               5                   10                  15

Phe Phe

<210> SEQ ID NO 63
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 63

Asp Trp Leu Arg Ala Phe Tyr Asp Lys Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 64

Glu Trp Leu Arg Ala Phe Tyr Glu Lys Val Ala Glu Lys Leu Lys Glu
1               5                   10                  15

Ala Phe

<210> SEQ ID NO 65
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 65

Asp Trp Leu Lys Ala Phe Tyr Asp Arg Val Ala Glu Lys Leu Lys Glu
1               5                   10                  15

Ala Phe
```

<210> SEQ ID NO 66
<211> LENGTH: 18
<212> TYPE: PRT
<213> ORGANISM: Artificial Sequence
<220> FEATURE:
<223> OTHER INFORMATION: Chemically synthesized peptide.
       Amino acids can be protected or unprotected D or L form.

<400> SEQUENCE: 66

Glu Trp Leu Lys Ala Phe Tyr Glu Arg Val Ala Glu Lys Leu Lys Glu
1               5                   10                  15

Ala Phe

<210> SEQ ID NO 67
<211> LENGTH: 18
<212> TYPE: PRT
<213> ORGANISM: Artificial Sequence
<220> FEATURE:
<223> OTHER INFORMATION: Chemically synthesized peptide.
       Amino acids can be protected or unprotected D or L form.

<400> SEQUENCE: 67

Asp Trp Leu Lys Ala Phe Tyr Asp Lys Val Ala Glu Arg Leu Lys Glu
1               5                   10                  15

Ala Phe

<210> SEQ ID NO 68
<211> LENGTH: 18
<212> TYPE: PRT
<213> ORGANISM: Artificial Sequence
<220> FEATURE:
<223> OTHER INFORMATION: Chemically synthesized peptide.
       Amino acids can be protected or unprotected D or L form.

<400> SEQUENCE: 68

Glu Trp Leu Lys Ala Phe Tyr Glu Lys Val Ala Glu Arg Leu Lys Glu
1               5                   10                  15

Ala Phe

<210> SEQ ID NO 69
<211> LENGTH: 18
<212> TYPE: PRT
<213> ORGANISM: Artificial Sequence
<220> FEATURE:
<223> OTHER INFORMATION: Chemically synthesized peptide.
       Amino acids can be protected or unprotected D or L form.

<400> SEQUENCE: 69

Asp Trp Leu Lys Ala Phe Tyr Asp Lys Val Ala Glu Lys Leu Arg Glu
1               5                   10                  15

Ala Phe

<210> SEQ ID NO 70
<211> LENGTH: 18
<212> TYPE: PRT
<213> ORGANISM: Artificial Sequence
<220> FEATURE:
<223> OTHER INFORMATION: Chemically synthesized peptide.
       Amino acids can be protected or unprotected D or L form.

<400> SEQUENCE: 70

Glu Trp Leu Lys Ala Phe Tyr Glu Lys Val Ala Glu Lys Leu Arg Glu
1               5                   10                  15

Ala Phe

<210> SEQ ID NO 71
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 71

Asp Trp Leu Lys Ala Phe Tyr Asp Arg Val Ala Glu Arg Leu Lys Glu
1               5                   10                  15

Ala Phe

<210> SEQ ID NO 72
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 72

Glu Trp Leu Lys Ala Phe Tyr Glu Arg Val Ala Glu Arg Leu Lys Glu
1               5                   10                  15

Ala Phe

<210> SEQ ID NO 73
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 73

Asp Trp Leu Arg Ala Phe Tyr Asp Lys Val Ala Glu Lys Leu Arg Glu
1               5                   10                  15

Ala Phe

<210> SEQ ID NO 74
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 74

Glu Trp Leu Arg Ala Phe Tyr Glu Lys Val Ala Glu Lys Leu Arg Glu
1               5                   10                  15

Ala Phe

<210> SEQ ID NO 75
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 75

Asp Trp Leu Arg Ala Phe Tyr Asp Arg Val Ala Glu Lys Leu Lys Glu
1               5                   10                  15

Ala Phe

<210> SEQ ID NO 76
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 76

Glu Trp Leu Arg Ala Phe Tyr Glu Arg Val Ala Glu Lys Leu Lys Glu
 1               5                  10                  15

Ala Phe

<210> SEQ ID NO 77
<211> LENGTH: 18
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 77

Asp Trp Leu Lys Ala Phe Tyr Asp Lys Val Ala Glu Arg Leu Arg Glu
 1               5                  10                  15

Ala Phe

<210> SEQ ID NO 78
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 78

Glu Trp Leu Lys Ala Phe Tyr Glu Lys Val Ala Glu Arg Leu Arg Glu
 1               5                  10                  15

Ala Phe

<210> SEQ ID NO 79
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 79

Asp Trp Leu Arg Ala Phe Tyr Asp Lys Val Ala Glu Arg Leu Lys Glu
 1               5                  10                  15

Ala Phe

<210> SEQ ID NO 80
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 80

Glu Trp Leu Arg Ala Phe Tyr Glu Lys Val Ala Glu Arg Leu Lys Glu

```
                1               5                  10                 15
Ala Phe

<210> SEQ ID NO 81
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 81

Asp Trp Leu Lys Ala Phe Tyr Asp Lys Val Ala Glu Lys Leu Lys Glu
 1               5                  10                 15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 82
<211> LENGTH: 37
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 82

Asp Trp Leu Lys Ala Phe Tyr Asp Lys Val Ala Glu Lys Leu Lys Glu
 1               5                  10                 15

Phe Phe Pro Asp Trp Leu Lys Ala Phe Tyr Asp Lys Val Ala Glu Lys
            20                  25                  30

Leu Lys Glu Phe Phe
        35

<210> SEQ ID NO 83
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 83

Asp Trp Phe Lys Ala Phe Tyr Asp Lys Val Ala Glu Lys Leu Lys Glu
 1               5                  10                 15

Ala Phe Pro Asp Trp Phe Lys Ala Phe Tyr Asp Lys Val Ala Glu Lys
            20                  25                  30

Leu Lys Glu Ala Phe
        35

<210> SEQ ID NO 84
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 84

Asp Lys Leu Lys Ala Phe Tyr Asp Lys Val Phe Glu Trp Ala Lys Glu
 1               5                  10                 15

Ala Phe Pro Asp Lys Leu Lys Ala Phe Tyr Asp Lys Val Phe Glu Trp
```

```
                  20                  25                  30

Leu Lys Glu Ala Phe
        35

<210> SEQ ID NO 85
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 85

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
        35

<210> SEQ ID NO 86
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 86

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 87
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 87

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
        35

<210> SEQ ID NO 88
<211> LENGTH: 37
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 88

Asp Trp Leu Lys Ala Phe Tyr Asp Lys Phe Ala Glu Lys Phe Lys Glu
1               5                   10                  15
```

```
Phe Phe Pro Asp Trp Leu Lys Ala Phe Tyr Asp Lys Phe Ala Glu Lys
            20                  25                  30

Phe Lys Glu Phe Phe
        35

<210> SEQ ID NO 89
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 89

Glu Trp Phe Lys Ala Phe Tyr Glu Lys Val Ala Glu Lys Phe Lys Glu
1               5                   10                  15

Ala Phe

<210> SEQ ID NO 90
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 90

Asp Trp Phe Lys Ala Phe Tyr Asp Lys Val Ala Glu Lys Phe
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 91

Phe Lys Ala Phe Tyr Asp Lys Val Ala Glu Lys Phe Lys Glu
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 92

Phe Lys Ala Phe Tyr Glu Lys Val Ala Glu Lys Phe Lys Glu
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 93

Asn Met Ala Phe Lys Ala Phe Tyr Asp Lys Val Ala Glu Lys Phe Lys
1               5                   10                  15

Glu
```

<210> SEQ ID NO 94
<211> LENGTH: 17
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 94

Asn Met Ala Phe Lys Ala Phe Tyr Glu Lys Val Ala Glu Lys Phe Lys
1               5                   10                  15

Glu

<210> SEQ ID NO 95
<211> LENGTH: 21
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 95

Asn Met Ala Asp Trp Phe Lys Ala Phe Tyr Asp Lys Val Ala Glu Lys
1               5                   10                  15

Phe Lys Glu Ala Phe
            20

<210> SEQ ID NO 96
<211> LENGTH: 21
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 96

Asn Met Ala Glu Trp Phe Lys Ala Phe Tyr Glu Lys Val Ala Glu Lys
1               5                   10                  15

Phe Lys Glu Ala Phe
            20

<210> SEQ ID NO 97
<211> LENGTH: 17
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 97

Asn Met Ala Ala Phe Tyr Asp Lys Val Ala Glu Lys Phe Lys Glu Ala
1               5                   10                  15

Phe

<210> SEQ ID NO 98
<211> LENGTH: 17
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 98

Asn Met Ala Asp Trp Phe Lys Ala Phe Tyr Asp Lys Val Ala Glu Lys

```
                1               5              10              15
Phe

<210> SEQ ID NO 99
<211> LENGTH: 39
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 99

Asp Trp Leu Lys Ala Phe Tyr Asp Lys Val Phe Glu Lys Phe Lys Glu
1               5                  10                  15

Phe Phe Asn Met Ala Asp Trp Leu Lys Ala Phe Tyr Asp Lys Val Phe
            20                  25                  30

Glu Lys Phe Lys Glu Phe Phe
        35

<210> SEQ ID NO 100
<211> LENGTH: 39
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 100

Glu Trp Leu Lys Ala Phe Tyr Glu Lys Val Phe Glu Lys Phe Lys Glu
1               5                  10                  15

Phe Phe Asn Met Ala Glu Trp Leu Lys Ala Phe Tyr Glu Lys Val Phe
            20                  25                  30

Glu Lys Phe Lys Glu Phe Phe
        35

<210> SEQ ID NO 101
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 101

Ala Phe Tyr Asp Lys Val Phe Glu Lys Phe Lys Glu Phe Phe Asn Met
1               5                  10                  15

Ala Ala Phe Tyr Asp Lys Val Phe Glu Lys Phe Lys Glu Phe Phe
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 102

Ala Phe Tyr Glu Lys Val Phe Glu Lys Phe Lys Glu Phe Phe Asn Met
1               5                  10                  15

Ala Ala Phe Tyr Glu Lys Val Phe Glu Lys Phe Lys Glu Phe Phe
            20                  25                  30
```

<210> SEQ ID NO 103
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 103

Asp Trp Leu Lys Ala Phe Tyr Asp Lys Val Phe Glu Lys Phe Asn Met
1               5                   10                  15

Ala Asp Trp Leu Lys Ala Phe Tyr Asp Lys Val Phe Glu Lys Phe
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 104

Glu Trp Leu Lys Ala Phe Tyr Glu Lys Val Phe Glu Lys Phe Asn Met
1               5                   10                  15

Ala Glu Trp Leu Lys Ala Phe Tyr Glu Lys Val Phe Glu Lys Phe
            20                  25                  30

<210> SEQ ID NO 105
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 105

Leu Lys Ala Phe Tyr Asp Lys Val Phe Glu Lys Phe Lys Glu Asn Met
1               5                   10                  15

Ala Leu Lys Ala Phe Tyr Asp Lys Val Phe Glu Lys Phe Lys Glu
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 106

Leu Lys Ala Phe Tyr Glu Lys Val Phe Glu Lys Phe Lys Glu Asn Met
1               5                   10                  15

Ala Leu Lys Ala Phe Tyr Glu Lys Val Phe Glu Lys Phe Lys Glu
            20                  25                  30

<210> SEQ ID NO 107
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 107

Asp Lys Trp Lys Ala Val Tyr Asp Lys Phe Ala Glu Ala Phe Lys Glu

```
                1               5                   10                  15

Phe Leu

<210> SEQ ID NO 108
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 108

Asp Lys Leu Lys Ala Phe Tyr Asp Lys Val Phe Glu Trp Ala Lys Glu
1               5                   10                  15

Ala Phe

<210> SEQ ID NO 109
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 109

Lys Arg Ser
1

<210> SEQ ID NO 110
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 110

Lys Arg Thr
1

<210> SEQ ID NO 111
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 111

Trp Arg Ile
1

<210> SEQ ID NO 112
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 112

Trp Arg Leu
1

<210> SEQ ID NO 113
<211> LENGTH: 3
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 113

Phe Arg Ile
1

<210> SEQ ID NO 114
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 114

Phe Arg Leu
1

<210> SEQ ID NO 115
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 115

Lys Glu Ser
1

<210> SEQ ID NO 116
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 116

Lys Glu Thr
1

<210> SEQ ID NO 117
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 117

Lys Asp Ser
1

<210> SEQ ID NO 118
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 118

Lys Asp Thr
```

<210> SEQ ID NO 119
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 119

Lys Arg Ser
1

<210> SEQ ID NO 120
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 120

Lys Arg Thr
1

<210> SEQ ID NO 121
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 121

Leu Glu Ser
1

<210> SEQ ID NO 122
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 122

Leu Glu Thr
1

<210> SEQ ID NO 123
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 123

Trp Arg Ser
1

<210> SEQ ID NO 124
<211> LENGTH: 3
<212> TYPE: PRT
<213> ORGANISM: Artificial Sequence
<220> FEATURE:
<223> OTHER INFORMATION: Chemically synthesized peptide.

Amino acids can be protected or unprotected D or L form.

<400> SEQUENCE: 124

Trp Asp Ser
1

<210> SEQ ID NO 125
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 125

Trp Glu Ser
1

<210> SEQ ID NO 126
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 126

Trp Arg Ser
1

<210> SEQ ID NO 127
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 127

Lys Glu Leu
1

<210> SEQ ID NO 128
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 128

Leu Arg Ser
1

<210> SEQ ID NO 129
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 129

Leu Asp Ser
1

<210> SEQ ID NO 130

```
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 130

Leu Glu Ser
1

<210> SEQ ID NO 131
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 131

Leu Arg Ser
1

<210> SEQ ID NO 132
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 132

Leu Arg Thr
1

<210> SEQ ID NO 133
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 133

Glu Asp Tyr
1

<210> SEQ ID NO 134
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 134

Lys Arg Ser
1

<210> SEQ ID NO 135
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 135
```

```
Trp Arg Ile
1

<210> SEQ ID NO 136
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 136

Trp Arg Leu
1

<210> SEQ ID NO 137
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 137

Phe Arg Ile
1

<210> SEQ ID NO 138
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 138

Phe Arg Leu
1

<210> SEQ ID NO 139
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 139

Trp Arg Phe
1

<210> SEQ ID NO 140
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 140

Trp Arg Tyr
1

<210> SEQ ID NO 141
<211> LENGTH: 3
<212> TYPE: PRT
<213> ORGANISM: Artificial Sequence
<220> FEATURE:
```

```
<223> OTHER INFORMATION: Chemically synthesized peptide.
      Amino acids can be protected or unprotected D or L form.

<400> SEQUENCE: 141

Trp Arg Phe
1

<210> SEQ ID NO 142
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 142

Trp Arg Tyr
1

<210> SEQ ID NO 143
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine

<400> SEQUENCE: 143

Xaa Arg Ser
1

<210> SEQ ID NO 144
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 144

Lys Arg Ser
1

<210> SEQ ID NO 145
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 145

Lys Arg Thr
1

<210> SEQ ID NO 146
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 146
```

Leu Asp Thr
1

<210> SEQ ID NO 147
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 147

Leu Glu Thr
1

<210> SEQ ID NO 148
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 148

Leu Arg Thr
1

<210> SEQ ID NO 149
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 149

Xaa Arg Ser
1

<210> SEQ ID NO 150
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 150

Xaa Asp Ser
1

<210> SEQ ID NO 151
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithiine

<400> SEQUENCE: 151

Xaa Glu Ser
1

<210> SEQ ID NO 152
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 152

Lys Arg Ser
1

<210> SEQ ID NO 153
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 153

Lys Arg Thr
1

<210> SEQ ID NO 154
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 154

Lys Glu Ser
1

<210> SEQ ID NO 155
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 155

Lys Glu Thr
1

<210> SEQ ID NO 156
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 156

Lys Asp Ser
1

-continued

```
<210> SEQ ID NO 157
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 157

Lys Asp Thr
1

<210> SEQ ID NO 158
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 158

Lys Glu Leu
1

<210> SEQ ID NO 159
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 159

Lys Arg Leu
1

<210> SEQ ID NO 160
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 160

Lys Arg Thr
1

<210> SEQ ID NO 161
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 161

Lys Glu Ser
1

<210> SEQ ID NO 162
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
```

```
<400> SEQUENCE: 162

Lys Glu Thr
1

<210> SEQ ID NO 163
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 163

Lys Asp Ser
1

<210> SEQ ID NO 164
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 164

Lys Asp Thr
1

<210> SEQ ID NO 165
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 165

Lys Arg Ser
1

<210> SEQ ID NO 166
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 166

Lys Glu Leu
1

<210> SEQ ID NO 167
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 167

Lys Asp Ser
1

<210> SEQ ID NO 168
<211> LENGTH: 3
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 168

Lys Asp Thr
1

<210> SEQ ID NO 169
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 169

Lys Arg Thr
1

<210> SEQ ID NO 170
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 170

Lys Glu Leu
1

<210> SEQ ID NO 171
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 171

Xaa Glu Ser
1

<210> SEQ ID NO 172
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 172

Xaa Asp Ser
1

<210> SEQ ID NO 173
<211> LENGTH: 3
<212> TYPE: PRT
```

```
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 173

Xaa Asp Thr
1

<210> SEQ ID NO 174
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 174

Xaa Arg Thr
1

<210> SEQ ID NO 175
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 175

Xaa Glu Thr
1

<210> SEQ ID NO 176
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 176

Trp Asp Ile
1

<210> SEQ ID NO 177
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 177

Trp Arg Ile
1
```

<210> SEQ ID NO 178
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 178

Trp Glu Ile
1

<210> SEQ ID NO 179
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 179

Trp Asp Leu
1

<210> SEQ ID NO 180
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 180

Trp Glu Leu
1

<210> SEQ ID NO 181
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 181

Phe Asp Ile
1

<210> SEQ ID NO 182
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 182

Phe Asp Leu
1

<210> SEQ ID NO 183
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 183

Phe Glu Leu
1

<210> SEQ ID NO 184
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 184

Trp Arg Phe
1

<210> SEQ ID NO 185
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 185

Trp Glu Phe
1

<210> SEQ ID NO 186
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 186

Trp Asp Phe
1

<210> SEQ ID NO 187
<211> LENGTH: 3
<212> TYPE: PRT
<213> ORGANISM: Artificial Sequen Sequencece
<220> FEATURE:
<223> OTHER INFORMATION: Chemically synthesized peptide.
      Amino acids can be protected or unprotected D or L form.

<400> SEQUENCE: 187

Trp Asp Tyr
1

<210> SEQ ID NO 188
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 188

Trp Arg Tyr
1

<210> SEQ ID NO 189
<211> LENGTH: 3
<212> TYPE: PRT
<213> ORGANISM: Artificial Sequence

```
<220> FEATURE:
<223> OTHER INFORMATION: Chemically synthesized peptide.
      Amino acids can be protected or unprotected D or L form.

<400> SEQUENCE: 189

Trp Glu Tyr
1

<210> SEQ ID NO 190
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 190

Trp Arg Thr
1

<210> SEQ ID NO 191
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 191

Trp Asp Thr
1

<210> SEQ ID NO 192
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 192

Trp Glu Thr
1

<210> SEQ ID NO 193
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (3)..(3)
<223> OTHER INFORMATION: Xaa is norleucine.

<400> SEQUENCE: 193

Phe Arg Xaa
1

<210> SEQ ID NO 194
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
```

```
<222> LOCATION: (3)..(3)
<223> OTHER INFORMATION: Xaa is norleucine.

<400> SEQUENCE: 194

Phe Glu Xaa
1

<210> SEQ ID NO 195
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (3)..(3)
<223> OTHER INFORMATION: Xaa is norleucine.

<400> SEQUENCE: 195

Phe Asp Xaa
1

<210> SEQ ID NO 196
<211> LENGTH: 3
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 196

Glu His Tyr
1

<210> SEQ ID NO 197
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 197

Leu His Ser
1

<210> SEQ ID NO 198
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 198

Leu His Thr
1

<210> SEQ ID NO 199
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 199
```

Lys His Ser
1

<210> SEQ ID NO 200
<211> LENGTH: 3
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 200

Lys His Thr
1

<210> SEQ ID NO 201
<211> LENGTH: 3
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 201

Lys His Leu
1

<210> SEQ ID NO 202
<211> LENGTH: 3
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 202

Lys His Ser
1

<210> SEQ ID NO 203
<211> LENGTH: 3
<212> TYPE: PRT
<213> ORGANISM: Artificial
<220> FEATURE:
<223> OTHER INFORMATION: Chemically synthesized peptide.
    Amino acids can be protected or unprotected D or L form.

<400> SEQUENCE: 203

Lys His Thr
1

<210> SEQ ID NO 204
<211> LENGTH: 3
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 204

Lys His Leu
1

<210> SEQ ID NO 205
<211> LENGTH: 3
<212> TYPE: PRT
<213> ORGANISM: Artificial Sequence
<220> FEATURE:

```
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is orniithine.

<400> SEQUENCE: 205

Xaa His Ser
1

<210> SEQ ID NO 206
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is orniithine.

<400> SEQUENCE: 206

Xaa His Thr
1

<210> SEQ ID NO 207
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 207

Phe His Ile
1

<210> SEQ ID NO 208
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 208

Phe His Leu
1

<210> SEQ ID NO 209
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (3)..(3)
<223> OTHER INFORMATION: Xaa is norleucine.

<400> SEQUENCE: 209

Phe His Xaa
1

<210> SEQ ID NO 210
<211> LENGTH: 3
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 210

Phe Lys Leu
1

<210> SEQ ID NO 211
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 211

Trp His Ile
1

<210> SEQ ID NO 212
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 212

Trp His Leu
1

<210> SEQ ID NO 213
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 213

Trp His Phe
1

<210> SEQ ID NO 214
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 214

Trp His Tyr
1

<210> SEQ ID NO 215
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 215

Phe Lys Leu
```

```
<210> SEQ ID NO 216
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 216

Lys His Ser
1

<210> SEQ ID NO 217
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 217

Lys His Thr
1

<210> SEQ ID NO 218
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 218

Lys His Leu
1

<210> SEQ ID NO 219
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 219

Leu His Ser
1

<210> SEQ ID NO 220
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 220

Leu His Thr
1

<210> SEQ ID NO 221
<211> LENGTH: 3
<212> TYPE: PRT
<213> ORGANISM: Artificial Sequence
<220> FEATURE:
<223> OTHER INFORMATION: Chemically synthesized peptide.
```

```
      Amino acids can be protected or unprotected D or L form.

<400> SEQUENCE: 221

Lys His Ser
1

<210> SEQ ID NO 222
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 222

Lys His Thr
1

<210> SEQ ID NO 223
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 223

Lys His Leu
1

<210> SEQ ID NO 224
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 224

Lys His Ser
1

<210> SEQ ID NO 225
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 225

Lys His Thr
1

<210> SEQ ID NO 226
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is norleucine.

<400> SEQUENCE: 226

Xaa His Ser
```

```
<210> SEQ ID NO 227
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 227

Phe His Ile
1

<210> SEQ ID NO 228
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 228

Phe His Leu
1

<210> SEQ ID NO 229
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (3)..(3)
<223> OTHER INFORMATION: Xaa is norleucine.

<400> SEQUENCE: 229

Phe His Xaa
1

<210> SEQ ID NO 230
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 230

Trp His Ser
1

<210> SEQ ID NO 231
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 231

Trp His Ile
1

<210> SEQ ID NO 232
<211> LENGTH: 3
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 232

Trp His Leu
1

<210> SEQ ID NO 233
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 233

Trp His Phe
1

<210> SEQ ID NO 234
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 234

Trp His Tyr
1

<210> SEQ ID NO 235
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 235

Trp His Thr
1

<210> SEQ ID NO 236
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 236

Lys His Ser
1

<210> SEQ ID NO 237
<211> LENGTH: 3
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 237

Lys His Thr
```

```
<210> SEQ ID NO 238
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 238

Lys Arg Asp Ser
1

<210> SEQ ID NO 239
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 239

Lys Arg Asp Thr
1

<210> SEQ ID NO 240
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 240

Trp Arg Asp Ile
1

<210> SEQ ID NO 241
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 241

Trp Arg Asp Leu
1

<210> SEQ ID NO 242
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 242

Phe Arg Asp Leu
1

<210> SEQ ID NO 243
<211> LENGTH: 4
<212> TYPE: PRT
<213> ORGANISM: Artificial Sequence
<220> FEATURE:
<223> OTHER INFORMATION: Chemically synthesized peptide.
```

Amino acids can be protected or unprotected D or L form.

<400> SEQUENCE: 243

Phe Arg Asp Ile
1

<210> SEQ ID NO 244
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 244

Phe Arg Asp Xaa
1

<210> SEQ ID NO 245
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 245

Phe Arg Glu Xaa
1

<210> SEQ ID NO 246
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 246

Phe Arg Glu Ile
1

<210> SEQ ID NO 247
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 247

Phe Asp Arg Ile
1

<210> SEQ ID NO 248
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

```
<400> SEQUENCE: 248

Phe Glu Arg Ile
1

<210> SEQ ID NO 249
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 249

Phe Asp Arg Leu
1

<210> SEQ ID NO 250
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 250

Phe Arg Glu Leu
1

<210> SEQ ID NO 251
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 251

Phe Glu Arg Leu
1

<210> SEQ ID NO 252
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 252

Phe Asp Arg Xaa
1

<210> SEQ ID NO 253
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.
```

```
<400> SEQUENCE: 253

Phe Glu Arg Xaa
1

<210> SEQ ID NO 254
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 254

Lys Glu Arg Ser
1

<210> SEQ ID NO 255
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 255

Lys Glu Arg Thr
1

<210> SEQ ID NO 256
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 256

Lys Asp Arg Ser
1

<210> SEQ ID NO 257
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 257

Lys Asp Arg Thr
1

<210> SEQ ID NO 258
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 258

Lys Arg Glu Ser
1

<210> SEQ ID NO 259
<211> LENGTH: 4
<212> TYPE: PRT
```

```
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 259

Lys Arg Glu Thr
1

<210> SEQ ID NO 260
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 260

Leu Glu Arg Ser
1

<210> SEQ ID NO 261
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 261

Leu Glu Arg Thr
1

<210> SEQ ID NO 262
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 262

Trp Arg Asp Ser
1

<210> SEQ ID NO 263
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 263

Trp Asp Arg Ser
1

<210> SEQ ID NO 264
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 264

Trp Glu Arg Ser
1
```

```
<210> SEQ ID NO 265
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 265

Trp Arg Glu Ser
1

<210> SEQ ID NO 266
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 266

Lys Glu Arg Leu
1

<210> SEQ ID NO 267
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 267

Leu Arg Asp Ser
1

<210> SEQ ID NO 268
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 268

Leu Asp Arg Ser
1

<210> SEQ ID NO 269
<211> LENGTH: 4
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 269

Leu Glu Arg Ser
1

<210> SEQ ID NO 270
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
```

```
<400> SEQUENCE: 270

Leu Arg Glu Ser
1

<210> SEQ ID NO 271
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 271

Leu Arg Asp Thr
1

<210> SEQ ID NO 272
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 272

Glu Asp Arg Tyr
1

<210> SEQ ID NO 273
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 273

Lys Arg Asp Ser
1

<210> SEQ ID NO 274
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 274

Trp Arg Asp Ile
1

<210> SEQ ID NO 275
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 275

Trp Arg Asp Leu
1

<210> SEQ ID NO 276
<211> LENGTH: 4
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 276

Phe Arg Asp Ile
1

<210> SEQ ID NO 277
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 277

Phe Arg Asp Leu
1

<210> SEQ ID NO 278
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 278

Trp Arg Asp Phe
1

<210> SEQ ID NO 279
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 279

Trp Arg Asp Tyr
1

<210> SEQ ID NO 280
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 280

Trp Arg Asp Phe
1

<210> SEQ ID NO 281
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 281

Trp Arg Asp Tyr
```

```
<210> SEQ ID NO 282
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(2)
<223> OTHER INFORMATION: Xaa is ornithine.

<400> SEQUENCE: 282

Xaa Arg Glu Ser
1

<210> SEQ ID NO 283
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 283

Lys Arg Asp Ser
1

<210> SEQ ID NO 284
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 284

Lys Arg Asp Thr
1

<210> SEQ ID NO 285
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 285

Leu Asp Arg Thr
1

<210> SEQ ID NO 286
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 286

Leu Glu Arg Thr
1

<210> SEQ ID NO 287
<211> LENGTH: 4
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 287

Leu Arg Glu Thr
1

<210> SEQ ID NO 288
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is norleucine.

<400> SEQUENCE: 288

Xaa Arg Asp Ser
1

<210> SEQ ID NO 289
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is norleucine.

<400> SEQUENCE: 289

Xaa Asp Arg Ser
1

<210> SEQ ID NO 290
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is norleucine.

<400> SEQUENCE: 290

Xaa Glu Arg Ser
1

<210> SEQ ID NO 291
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is norleucine.

<400> SEQUENCE: 291
```

```
Xaa Arg Glu Ser
1

<210> SEQ ID NO 292
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 292

Lys Arg Asp Ser
1

<210> SEQ ID NO 293
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 293

Lys Arg Asp Thr
1

<210> SEQ ID NO 294
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 294

Lys Glu Arg Ser
1

<210> SEQ ID NO 295
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 295

Lys Glu Arg Thr
1

<210> SEQ ID NO 296
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 296

Lys Asp Arg Ser
1

<210> SEQ ID NO 297
<211> LENGTH: 4
<212> TYPE: PRT
<213> ORGANISM: Artificial Sequence
```

```
<220> FEATURE:
<223> OTHER INFORMATION: Chemically synthesized peptide.
      Amino acids can be protected or unprotected D or L form.

<400> SEQUENCE: 297

Lys Asp Arg Thr
1

<210> SEQ ID NO 298
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 298

Lys Arg Glu Ser
1

<210> SEQ ID NO 299
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 299

Lys Arg Glu Thr
1

<210> SEQ ID NO 300
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 300

Lys Glu Arg Leu
1

<210> SEQ ID NO 301
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 301

Lys Arg Glu Leu
1

<210> SEQ ID NO 302
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 302

Lys Arg Asp Thr
1
```

<210> SEQ ID NO 303
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 303

Lys Glu Arg Ser
1

<210> SEQ ID NO 304
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 304

Lys Glu Arg Thr
1

<210> SEQ ID NO 305
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 305

Lys Asp Arg Ser
1

<210> SEQ ID NO 306
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 306

Lys Asp Arg Thr
1

<210> SEQ ID NO 307
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 307

Lys Arg Glu Ser
1

<210> SEQ ID NO 308
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

```
<400> SEQUENCE: 308

Lys Arg Glu Thr
1

<210> SEQ ID NO 309
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 309

Lys Glu Arg Leu
1

<210> SEQ ID NO 310
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 310

Lys Arg Asp Ser
1

<210> SEQ ID NO 311
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 311

Lys Arg Asp Thr
1

<210> SEQ ID NO 312
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 312

Lys Glu Arg Ser
1

<210> SEQ ID NO 313
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 313

Lys Glu Arg Thr
1

<210> SEQ ID NO 314
<211> LENGTH: 4
<212> TYPE: PRT
```

```
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 314

Lys Asp Arg Ser
1

<210> SEQ ID NO 315
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 315

Lys Asp Arg Thr
1

<210> SEQ ID NO 316
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 316

Lys Arg Glu Ser
1

<210> SEQ ID NO 317
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 317

Lys Arg Glu Thr
1

<210> SEQ ID NO 318
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 318

Lys Glu Arg Leu
1

<210> SEQ ID NO 319
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.
```

-continued

```
<400> SEQUENCE: 319

Xaa Arg Glu Ser
1

<210> SEQ ID NO 320
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine

<400> SEQUENCE: 320

Xaa Glu Arg Ser
1

<210> SEQ ID NO 321
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 321

Xaa Arg Asp Ser
1

<210> SEQ ID NO 322
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 322

Xaa Asp Arg Ser
1

<210> SEQ ID NO 323
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 323

Xaa Asp Arg Thr
1

<210> SEQ ID NO 324
```

```
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 324

Xaa Arg Asp Thr
1

<210> SEQ ID NO 325
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 325

Xaa Glu Arg Thr
1

<210> SEQ ID NO 326
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (1)..(1)
<223> OTHER INFORMATION: Xaa is ornithine.

<400> SEQUENCE: 326

Xaa Arg Glu Thr
1

<210> SEQ ID NO 327
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 327

Trp Asp Arg Ile
1

<210> SEQ ID NO 328
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 328

Trp Arg Glu Ile
1
```

<210> SEQ ID NO 329
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 329

Trp Glu Arg Ile
1

<210> SEQ ID NO 330
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 330

Trp Asp Arg Leu
1

<210> SEQ ID NO 331
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 331

Trp Arg Glu Leu
1

<210> SEQ ID NO 332
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 332

Trp Glu Arg Leu
1

<210> SEQ ID NO 333
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 333

Phe Asp Arg Ile
1

<210> SEQ ID NO 334
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

```
<400> SEQUENCE: 334

Phe Arg Glu Ile
1

<210> SEQ ID NO 335
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 335

Phe Glu Arg Ile
1

<210> SEQ ID NO 336
<211> LENGTH: 4
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 336

Phe Asp Arg Leu
1

<210> SEQ ID NO 337
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 337

Phe Arg Glu Leu
1

<210> SEQ ID NO 338
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 338

Phe Glu Arg Leu
1

<210> SEQ ID NO 339
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 339

Trp Arg Asp Phe
1

<210> SEQ ID NO 340
<211> LENGTH: 4
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 340

Trp Arg Glu Phe
1

<210> SEQ ID NO 341
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 341

Trp Glu Arg Phe
1

<210> SEQ ID NO 342
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 342

Trp Asp Arg Tyr
1

<210> SEQ ID NO 343
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 343

Trp Arg Glu Tyr
1

<210> SEQ ID NO 344
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 344

Trp Glu Arg Tyr
1

<210> SEQ ID NO 345
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 345

Trp Arg Asp Thr
```

<210> SEQ ID NO 346
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 346

Trp Asp Arg Thr
1

<210> SEQ ID NO 347
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 347

Trp Arg Glu Thr
1

<210> SEQ ID NO 348
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 348

Trp Glu Arg Thr
1

<210> SEQ ID NO 349
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 349

Phe Arg Asp Xaa
1

<210> SEQ ID NO 350
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 350

Phe Arg Glu Xaa
1

<210> SEQ ID NO 351
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 351

Phe Lys Asp Leu
1

<210> SEQ ID NO 352
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 352

Phe Asp Lys Leu
1

<210> SEQ ID NO 353
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 353

Phe Lys Glu Leu
1

<210> SEQ ID NO 354
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 354

Phe Glu Lys Leu
1

<210> SEQ ID NO 355
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 355

Phe Lys Asp Ile
1

<210> SEQ ID NO 356
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

```
<400> SEQUENCE: 356

Phe Asp Lys Ile
 1

<210> SEQ ID NO 357
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 357

Phe Lys Glu Ile
 1

<210> SEQ ID NO 358
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 358

Phe Glu Lys Ile
 1

<210> SEQ ID NO 359
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 359

Phe Lys Asp Xaa
 1

<210> SEQ ID NO 360
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 360

Phe Asp Lys Xaa
 1

<210> SEQ ID NO 361
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
```

```
<221> NAME/KEY: misc_feature
<222> LOCATION: (4)..(4)
<223> OTHER INFORMATION: Xaa is norleucine.

<400> SEQUENCE: 361

Phe Lys Glu Xaa
1

<210> SEQ ID NO 362
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 362

Phe Glu Lys Xaa
1

<210> SEQ ID NO 363
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 363

Phe His Asp Leu
1

<210> SEQ ID NO 364
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 364

Phe Asp His Leu
1

<210> SEQ ID NO 365
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 365

Phe His Glu Leu
1

<210> SEQ ID NO 366
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 366
```

Phe Glu His Leu
1

<210> SEQ ID NO 367
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 367

Phe His Asp Ile
1

<210> SEQ ID NO 368
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 368

Phe Asp His Ile
1

<210> SEQ ID NO 369
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 369

Phe His Glu Ile
1

<210> SEQ ID NO 370
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 370

Phe Glu His Ile
1

<210> SEQ ID NO 371
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 371

Phe His Asp Xaa
1

```
<210> SEQ ID NO 372
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 372

Phe Asp His Xaa
1

<210> SEQ ID NO 373
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 373

Phe His Glu Xaa
1

<210> SEQ ID NO 374
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
<220> FEATURE:
<221> NAME/KEY: misc_feature
<222> LOCATION: (4)..(4)
<223> OTHER INFORMATION: Xaa is norleucine.

<400> SEQUENCE: 374

Phe Glu His Xaa
1

<210> SEQ ID NO 375
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 375

Lys Lys Asp Ser
1

<210> SEQ ID NO 376
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 376

Lys Asp Lys Ser
```

<210> SEQ ID NO 377
<211> LENGTH: 4
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 377

Lys Lys Glu Ser
1

<210> SEQ ID NO 378
<211> LENGTH: 4
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 378

Lys Glu Lys Ser
1

<210> SEQ ID NO 379
<211> LENGTH: 4
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 379

Lys His Asp Ser
1

<210> SEQ ID NO 380
<211> LENGTH: 4
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 380

Lys Asp His Ser
1

<210> SEQ ID NO 381
<211> LENGTH: 4
<212> TYPE: PRT
<213> ORGANISM: Artificial Sequence
<220> FEATURE:
<223> OTHER INFORMATION: Chemically synthesized peptide.
    Amino acids can be protected or unprotected D or L form.

<400> SEQUENCE: 381

Lys His Glu Ser
1

<210> SEQ ID NO 382
<211> LENGTH: 4
<212> TYPE: PRT
<213> ORGANISM: Artificial Sequence
<220> FEATURE:
<223> OTHER INFORMATION: Chemically synthesized peptide.

Amino acids can be protected or unprotected D or L form.

<400> SEQUENCE: 382

Lys Glu His Ser
1

<210> SEQ ID NO 383
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 383

Lys Leu Arg Ser
1

<210> SEQ ID NO 384
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 384

Lys Arg Leu Ser
1

<210> SEQ ID NO 385
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 385

Lys Leu Arg Thr
1

<210> SEQ ID NO 386
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 386

Lys Arg Leu Thr
1

<210> SEQ ID NO 387
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 387

Lys Glu Leu Ser
1

<210> SEQ ID NO 388

```
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 388

Lys Leu Glu Ser
1

<210> SEQ ID NO 389
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 389

Lys Glu Leu Thr
1

<210> SEQ ID NO 390
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 390

Lys Leu Arg Ser
1

<210> SEQ ID NO 391
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 391

Lys Leu Arg Thr
1

<210> SEQ ID NO 392
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 392

Lys Glu Leu Ser
1

<210> SEQ ID NO 393
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 393
```

Lys Glu Leu Thr
1

<210> SEQ ID NO 394
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 394

Lys Glu Ile Thr
1

<210> SEQ ID NO 395
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 395

Lys Leu Arg Ser
1

<210> SEQ ID NO 396
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 396

Lys Leu Arg Thr
1

<210> SEQ ID NO 397
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 397

Lys Glu Leu Ser
1

<210> SEQ ID NO 398
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 398

Lys Glu Leu Thr
1

<210> SEQ ID NO 399
<211> LENGTH: 4
<212> TYPE: PRT
<213> ORGANISM: Artificial Sequence
<220> FEATURE:

```
<223> OTHER INFORMATION: Chemically synthesized peptide.
      Amino acids can be protected or unprotected D or L form.

<400> SEQUENCE: 399

Lys Leu Arg Ser
 1

<210> SEQ ID NO 400
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 400

Lys Arg Phe Thr
 1

<210> SEQ ID NO 401
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 401

Lys Leu Arg Thr
 1

<210> SEQ ID NO 402
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 402

Lys Glu Ile Thr
 1

<210> SEQ ID NO 403
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 403

Lys Glu Val Thr
 1

<210> SEQ ID NO 404
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 404

Lys Glu Ala Thr
 1
```

-continued

<210> SEQ ID NO 405
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 405

Lys Glu Gly Thr
1

<210> SEQ ID NO 406
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 406

Lys Glu Leu Ser
1

<210> SEQ ID NO 407
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 407

Lys Glu Leu Thr
1

<210> SEQ ID NO 408
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 408

Lys Arg Trp Tyr
1

<210> SEQ ID NO 409
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 409

Lys Trp Arg Tyr
1

<210> SEQ ID NO 410
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 410

Lys Arg Tyr Trp
1

<210> SEQ ID NO 411
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 411

Lys Tyr Arg Trp
1

<210> SEQ ID NO 412
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 412

Lys Arg Tyr Trp Thr
1               5

<210> SEQ ID NO 413
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 413

Lys Arg Tyr Thr
1

<210> SEQ ID NO 414
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 414

Lys Arg Trp Thr
1

<210> SEQ ID NO 415
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 415

Lys Arg Trp Tyr
1

<210> SEQ ID NO 416
<211> LENGTH: 4
<212> TYPE: PRT
<213> ORGANISM: Artificial Sequence

```
<220> FEATURE:
<223> OTHER INFORMATION: Chemically synthesized peptide.
      Amino acids can be protected or unprotected D or L form.

<400> SEQUENCE: 416

Lys Arg Tyr Trp
1

<210> SEQ ID NO 417
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 417

Lys Arg Tyr Trp Thr
1               5

<210> SEQ ID NO 418
<211> LENGTH: 4
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 418

Lys Arg Tyr Thr
1

<210> SEQ ID NO 419
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 419

Lys Arg Trp Thr
1

<210> SEQ ID NO 420
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 420

Lys Arg Trp Tyr
1

<210> SEQ ID NO 421
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 421

Lys Arg Tyr Trp
1
```

```
<210> SEQ ID NO 422
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 422

Lys Arg Tyr Trp Thr
1               5

<210> SEQ ID NO 423
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 423

Lys Arg Tyr Thr
1

<210> SEQ ID NO 424
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 424

Lys Arg Trp Thr
1

<210> SEQ ID NO 425
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 425

Glu Lys Arg Tyr
1

<210> SEQ ID NO 426
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 426

Lys Arg Trp Tyr
1

<210> SEQ ID NO 427
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.
```

```
<400> SEQUENCE: 427

Lys Arg Tyr Trp
1

<210> SEQ ID NO 428
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 428

Lys Arg Tyr Trp Thr
1               5

<210> SEQ ID NO 429
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 429

Lys Arg Tyr Thr
1

<210> SEQ ID NO 430
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 430

Lys Arg Phe Thr
1

<210> SEQ ID NO 431
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 431

Lys Arg Trp Thr
1

<210> SEQ ID NO 432
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 432

Lys Phe Trp Phe Ser
1               5

<210> SEQ ID NO 433
<211> LENGTH: 5
<212> TYPE: PRT
```

```
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 433

Lys Phe Trp Phe Thr
1               5

<210> SEQ ID NO 434
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 434

Lys Phe Tyr Phe Ser
1               5

<210> SEQ ID NO 435
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 435

Lys Phe Tyr Phe Thr
1               5

<210> SEQ ID NO 436
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 436

Lys Phe His Phe Ser
1               5

<210> SEQ ID NO 437
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 437

Lys Phe His Phe Thr
1               5

<210> SEQ ID NO 438
<211> LENGTH: 6
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 438

Lys Val Phe Phe Tyr Ser
1               5
```

<210> SEQ ID NO 439
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 439

Lys Phe Trp Phe Ser
1               5

<210> SEQ ID NO 440
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 440

Lys Phe Trp Phe Thr
1               5

<210> SEQ ID NO 441
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 441

Lys Phe Tyr Phe Ser
1               5

<210> SEQ ID NO 442
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 442

Lys Phe Tyr Phe Thr
1               5

<210> SEQ ID NO 443
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 443

Lys Phe His Phe Ser
1               5

<210> SEQ ID NO 444
<211> LENGTH: 5
<212> TYPE: PRT
<213> ORGANISM: Artificial
<220> FEATURE:
<223> OTHER INFORMATION: Chemically synthesized peptide.
      Amino acids can be protected or unprotected D or L form.

```
<400> SEQUENCE: 444

Lys Phe His Phe Thr
1               5

<210> SEQ ID NO 445
<211> LENGTH: 5
<212> TYPE: PRT
<213> ORGANISM: Artificial
<220> FEATURE:
<223> OTHER INFORMATION: Chemically synthesized peptide.
      Amino acids can be protected or unprotected D or L form.

<400> SEQUENCE: 445

Leu Phe Trp Phe Thr
1               5

<210> SEQ ID NO 446
<211> LENGTH: 5
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 446

Leu Phe Trp Phe Ser
1               5

<210> SEQ ID NO 447
<211> LENGTH: 7
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 447

Gly Gly Gly Gly Ser Ser Ser
1               5

<210> SEQ ID NO 448
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 448

Lys Arg Asp Ser
1

<210> SEQ ID NO 449
<211> LENGTH: 4
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 449

Lys Arg Asp Ser
1

<210> SEQ ID NO 450
<211> LENGTH: 18
```

```
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 450

Asp Trp Phe Lys Ala Phe Tyr Asp Lys Val Ala Glu Lys Phe Lys Glu
1               5                   10                  15

Ala Phe

<210> SEQ ID NO 451
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 451

Asp Trp Phe Lys Ala Phe Tyr Asp Lys Val Ala Glu Lys Phe Lys Glu
1               5                   10                  15

Ala Phe

<210> SEQ ID NO 452
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 452

Asp Trp Phe Lys Ala Phe Tyr Asp Lys Val Ala Glu Lys Phe Lys Glu
1               5                   10                  15

Ala Phe

<210> SEQ ID NO 453
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 453

Asp Trp Phe Lys Ala Phe Tyr Asp Lys Val Ala Glu Lys Phe Lys Glu
1               5                   10                  15

Ala Phe

<210> SEQ ID NO 454
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 454

Asp Trp Phe Lys Ala Phe Tyr Asp Lys Val Ala Glu Lys Phe Lys Glu
1               5                   10                  15

Ala Phe

<210> SEQ ID NO 455
```

```
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 455

Asp Trp Phe Lys Ala Phe Tyr Asp Lys Val Ala Glu Lys Phe Lys Glu
1               5                   10                  15

Ala Phe

<210> SEQ ID NO 456
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 456

Asp Trp Phe Lys Ala Phe Tyr Asp Lys Val Ala Glu Lys Phe Lys Glu
1               5                   10                  15

Ala Phe

<210> SEQ ID NO 457
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 457

Asp Trp Phe Lys Ala Phe Tyr Asp Lys Val Ala Glu Lys Phe Lys Glu
1               5                   10                  15

Ala Phe

<210> SEQ ID NO 458
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 458

Asp Trp Phe Lys Ala Phe Tyr Asp Lys Val Ala Glu Lys Phe Lys Glu
1               5                   10                  15

Ala Phe

<210> SEQ ID NO 459
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 459

Asp Trp Phe Lys Ala Phe Tyr Asp Lys Val Ala Glu Lys Phe Lys Glu
1               5                   10                  15

Ala Phe
```

-continued

```
<210> SEQ ID NO 460
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 460

Asp Trp Phe Lys Ala Phe Tyr Asp Lys Val Ala Glu Lys Phe Lys Glu
1               5                   10                  15

Ala Phe

<210> SEQ ID NO 461
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 461

Asp Trp Phe Lys Ala Phe Tyr Asp Lys Val Ala Glu Lys Phe Lys Glu
1               5                   10                  15

Ala Phe

<210> SEQ ID NO 462
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 462

Asp Trp Phe Lys Ala Phe Tyr Asp Lys Val Ala Glu Lys Phe Lys Glu
1               5                   10                  15

Ala Phe

<210> SEQ ID NO 463
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 463

Asp Trp Phe Lys Ala Phe Tyr Asp Lys Val Ala Glu Lys Phe Lys Glu
1               5                   10                  15

Ala Phe

<210> SEQ ID NO 464
<211> LENGTH: 18
<212> TYPE: PRT
<213> ORGANISM: Artificial Sequence
<220> FEATURE:
<223> OTHER INFORMATION: Chemically synthesized peptide.
      Amino acids can be protected or unprotected D or L form.

<400> SEQUENCE: 464

Asp Trp Phe Lys Ala Phe Tyr Asp Lys Val Ala Glu Lys Phe Lys Glu
1               5                   10                  15

Ala Phe
```